(12) United States Patent
Almansa-Rosales et al.

(10) Patent No.: US 10,407,428 B2
(45) Date of Patent: Sep. 10, 2019

(54) SPIRO-ISOQUINOLINE-1,4'-PIPERIDINE COMPOUNDS HAVING MULTIMODAL ACTIVITY AGAINST PAIN

(71) Applicant: ESTEVE PHARMACEUTICALS, S.A., Barcelona (ES)

(72) Inventors: Carmen Almansa-Rosales, Barcelona (ES); Monica Garcia Lopez, Barcelona (ES); Ana-Maria Caamano-Moure, Santiago de Compostela (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/527,909

(22) PCT Filed: Nov. 20, 2015

(86) PCT No.: PCT/EP2015/002332
§ 371 (c)(1),
(2) Date: May 18, 2017

(87) PCT Pub. No.: WO2016/078770
PCT Pub. Date: May 26, 2016

(65) Prior Publication Data
US 2018/0111935 A1    Apr. 26, 2018

(30) Foreign Application Priority Data
Nov. 21, 2014 (EP) .................................. 14382465

(51) Int. Cl.
C07D 471/10    (2006.01)
A61K 31/423    (2006.01)
C07D 471/20    (2006.01)
A61P 25/04     (2006.01)

(52) U.S. Cl.
CPC ............ *C07D 471/10* (2013.01); *A61P 25/04* (2018.01); *C07D 471/20* (2013.01)

(58) Field of Classification Search
CPC ............................ C07D 471/10; A61K 31/423
See application file for complete search history.

(56) References Cited

U.S. PATENT DOCUMENTS

| | | | |
|---|---|---|---|
| 3,301,857 A * | 1/1967 | Berger et al. ........ | C07D 471/10 |
| 6,013,652 A | 1/2000 | Maccoss | |
| 2004/0024002 A1 * | 2/2004 | Burnett ................ | C07D 471/10 514/278 |
| 2011/0092529 A1 * | 4/2011 | Brown ................. | C07D 405/14 514/278 |

FOREIGN PATENT DOCUMENTS

| WO | WO 94/29309  | 12/1994 |
|----|--------------|---------|
| WO | WO 95/28389  | 10/1995 |
| WO | WO2005016913 | 2/2005  |
| WO | WO 2007/028638 | 3/2007 |
| WO | WO2007121976 | 11/2007 |
| WO | WO2008125349 | 10/2008 |

OTHER PUBLICATIONS

International Search Report for PCT/EP2015/002332 dated Jan. 21, 2016.
Bornot et al., J. Med. Chem, 2013, 56, 1197-1210.
Chien, et al., Neuroscience Letters, 1995, 190, pp. 137-139.
Dickenson, et al., Eur J Pain 9, 113-116 (2005).
Goldberg, et al., BMC Public Health. 11, 770 (2011).
Mao, et al., J. Pain 12, 157-166 (2011).
Turk, et al., Lancet 377, 2226-2235 (2011).
Zamanillo, et al., Eur. J. Pharmacol, 716, 78-93 (2013).
Gabriel, et al., Assay Drug Dev. Technol., 2003, 1, 291-303.

* cited by examiner

*Primary Examiner* — Karen Cheng
(74) *Attorney, Agent, or Firm* — Hueschen and Sage

(57) ABSTRACT

The present invention relates to spiro-isoquinoline-1,4'-piperidine compounds having dual pharmacological activity towards both the sigma (σ) receptor and the μ-opiod receptor, to processes of preparation of such compounds, to pharmaceutical compositions comprising them, and to their use in therapy, in particular for the treatment of pain.

17 Claims, No Drawings

SPIRO-ISOQUINOLINE-1,4'-PIPERIDINE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or μ-opioid receptor) and more particularly to spiro-isoquinoline-1,4'-piperidine derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. *Eur J Pain* 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the σ1 receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the σ₁ receptor.

SUMMARY OF THE INVENTION

In this invention a family of structurally distinct spiro-isoquinoline-1,4'-piperidine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the sigma1 receptor and the μ-opioid receptor for use in the treatment of pain.

As this invention is aimed at providing a compound or a chemically related series of compounds which act as dual ligands of the σ₁ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general formula (I),

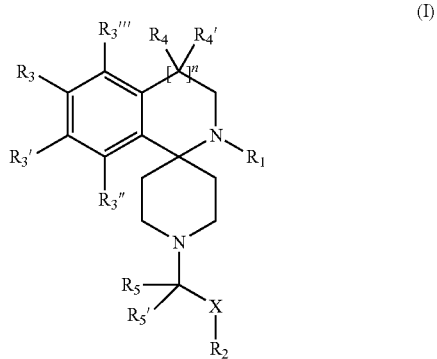

wherein $R_1$, $R_2$, $R_3$, $R_{3'}$, $R_{3''}$, $R_{3'''}$, $R_4$, $R_{4'}$, $R_5$, $R_{5'}$, X and n are as defined below in the detailed description.

DETAILED DESCRIPTION OF THE INVENTION

The invention is directed to a family of structurally distinct spiro-isoquinoline-1,4'-piperidine derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the σ₁ receptor and the μ-opioid receptor for use in the treatment of pain.

As this invention is aimed at providing a compound or a chemically related series of compounds which act as dual ligands of the σ₁ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to σ₁ receptor), thereby enhancing the opioid analgesia through the σ₁ activation without increasing the undesirable side effects. This supports the therapeutic value of a dual MOR/σ₁ receptor compound whereby the σ₁ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opiod receptor and to the σ₁ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: σ₁ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while σ₁ receptor antagonists show outstanding effects in preclinical neuropathic pain models. Thus, the σ₁ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem,* 56, 1197-1210 (2013)].

In a particular aspect, the present invention is directed to compounds of general formula (I):

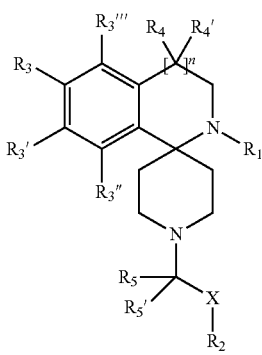

(I)

wherein n is 0 or 1

$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, —C(O)$R_6$, —C(O)CH$_2$OR$_6$, —C(O)CH$_2$OC(O)R$_6$, —C(O)OR$_6$, —C(O)NR$_6$R$_{6'}$ or —S(O)$_2$R$_6$;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl or substituted and unsubstituted alkyheterocylcyl;

$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

X is selected from —CR$_x$R$_{x'}$—, —CR$_x$OR$_{14'}$, —CR$_x$R$_x$NR$_7$—, —CR$_x$R$_x$O—, —CR$_x$R$_x$NR$_7$C(O)—, —C(O)—, —CR$_x$R$_x$C(O)—, —C(O)O—, —C(O)NR$_7$—, —CR$_x$R$_x$C(O)NR$_7$— and —C(O)NR$_7$CR$_x$R$_{x'}$—;

wherein $R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc;

$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{14}$, —C(O)NR$_{14}$R$_{14'}$, —NR$_{14}$C(O)R$_{14'}$, and —NR$_{14}$R$_{14''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively if X is —CR$_x$R$_{x'}$—, R$_x$ and R$_{x'}$ may form, together with the carbon atom to which they are attached, a substituted or unsubstituted heterocyclyl, or a substituted or unsubstituted cycloalkyl;

$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl and unsubstituted acetyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is selected from hydrogen, halogen, —R$_9$, —OR$_9$, —NO$_2$, —NR$_9$R$_{9'''}$, —NR$_9$C(O)R$_{9''}$, —NC(O)OR$_9$, —NR$_9$S(O)$_2$R$_{9'}$, —S(O)$_2$NR$_9$R$_{9''}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

$R_{3'}$, $R_{3''}$ and $R_{3'''}$ are independently selected from hydrogen, halogen, —R$_9$, —OR$_9$, —NO$_2$, —NR$_9$R$_{9'''}$, —NR$_9$C(O)R$_{9''}$, —NC(O)OR$_9$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

wherein $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl and unsubstituted acetyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ is selected from hydrogen, —OR$_{13}$, substituted or unsubstituted $C_{1-6}$ alkyl, substituted or unsubstituted $C_{2-6}$ alkenyl, substituted or unsubstituted $C_{2-6}$ alkynyl, —C(O)OR$_{13}$, —C(O)NR$_{13}$R$_{13'}$, —NR$_{13}$C(O)R$_{13'}$, —NR$_{13}$R$_{13'''}$, —NC(O)OR$_{13}$, and substituted or unsubstituted heterocyclyl;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following proviso is applying:

when X is CR$_x$R$_{x'}$ then R$_2$ may not be substituted or unsubstituted alkylaryl, substituted or unsubstituted alkylcycloalkyl or substituted or unsubstituted alkylheterocyclyl.

In another embodiment the following proviso is applying:

If n is 0, then R$_1$ may not be substituted or unsubstituted methyl.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C≡$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamanty. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl, alkenyl, alkynyl and O-alkyl—unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-4}$alkyl being unsubstituted or substituted with one or more of —$OR_c$ or halogen (F, Cl, I, Br), being $R_c$ one of $R_{10}$, $R_{11}$ or $R_{12}$, (being $R_{c'}$ one of $R_{11'}$, $R_{12'}$ or $R_{10'}$; being $R_{c''}$ one of $R_{11''}$ or $R_{12'''}$), wherein $R_1$ to $R_{14'''}$ are as defined in the description, and wherein when different radicals $R_1$ to $R_{14'''}$ are present simultaneously in Formula I they may be identical or different.

In connection with alkyl, alkenyl, alkynyl and O-alkyl—unless defined otherwise—the term substituted in the context of this invention is understood as meaning replacement of at least one hydrogen radical on a carbon atom by halogen (F, Cl, Br, I), —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-4}$alkyl being unsubstituted or substituted with one or more of —$OR_c$ or halogen (F, Cl, I, Br), being $R_c$ one of $R_{10}$, $R_{11}$ or $R_{12}$, (being $R_{c'}$ one of $R_{11'}$, $R_{12'}$ or $R_{10'}$; being $R_{c''}$ one of $R_{11''}$, $R_{12''}$ or $R_{10''}$; being $R_{c'''}$ one of $R_{11'''}$ or $R_{12'''}$), wherein $R_1$ to $R_{14'''}$ are as defined in the description, and wherein when different radicals $R_1$ to $R_{14'\infty 1}$ are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alky, alkenyl, alkynyl or O-alkyl, substituted is understood in the context of this invention that any alky, alkenyl, alkynyl or O-alkyl which is substituted is substituted with one or more of halogen (F, Cl, Br, I), —$OR_c$, —CN, haloalkyl, haloalkoxy or —$OC_{1-4}$alkyl being unsubstituted or substituted with one or more of —$OR_c$ or halogen (F, Cl, I, Br), being $R_c$ one of $R_{11}$, $R_{12}$ or $R_{10}$, (being $R_{c'}$ one of $R_{11'}$, $R_{12'}$ or $R_{10'}$; being $R_{c''}$ one of $R_{11''}$, $R_{12''}$ or $R_{10''}$; being $R_{c'''}$ one of $R_{11'''}$ or $R_{12'''}$), wherein $R_1$ to $R_{10'}$ are as defined in the description, and wherein when different radicals $R_1$ to $R_{14'''}$ are present simultaneously in Formula I they may be identical or different.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—CH$_2$—) groups. Most preferably alkylaryl is benzyl.

In the context of this invention alkylheterocyclyl is understood as meaning an heterocyclyl group being connected to another atom through a C$_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—CH$_2$—) groups. Most preferably alkylheterocyclyl is —CH$_2$-pyridine.

In the context of this invention alkylcycloalkyl is understood as meaning an cycloalkyl group being connected to another atom through a C$_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—CH$_2$—) groups. Most preferably alkylcycloalkyl is —CH$_2$-cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, benzothiazole, indole, benzotriazole, carbazole and quinazoline. Subgroups inside the heterocyclyls as understood herein include heteroaryls and non-aromatic heterocyclyls.

- the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, imidazole, pyrazole, oxazole, thiophene and benzimidazole;
- the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b] pyridine, benzoxazole, oxopyrrolidine, pyrimidine, oxazepane and pyrrolidine. It may also be thiomorpholine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.
Preferably, the heteroaryl is a monocyclic heteroaryl.
Preferably, the non-aromatic heterocyclyl is a monocyclic non-aromatic heterocyclyl.
Preferably, the cycloalkyl is a monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning one or more substitution(s) of the ring-system of the aryl or alkyl-aryl, cycloalkyl or alkyl-cycloalkyl; heterocyclyl or alkyl-heterocyclyl by halogen (F, Cl, Br, I), —R$_c$, —OR$_c$, —CN, —NO$_2$, —NR$_c$R$_{c'''}$, —C(O)OR$_c$, NR$_c$C(O)R$_{c'}$, —C(O)NR$_c$R$_{c'}$, —NR$_c$S(O)$_2$R$_{c'}$, =O, —OCH$_2$CH$_2$OH, —NR$_c$C(O)NR$_c$R$_{c''}$, —S(O)$_2$NR$_c$R$_{c'}$, —NR$_c$S(O)$_2$NR$_c$R$_{c''}$, haloalkyl, haloalkoxy, —SR$_c$, —S(O)R$_c$, —S(O)$_2$R$_c$ or C(CH$_3$)OR$_c$; NR$_c$R$_{c'''}$, with R$_c$ and R$_{c'''}$ independently being either H or a saturated or unsaturated, linear or branched, substituted or unsubstituted C$_{1-6}$-alkyl; a saturated or unsaturated, linear or branched, substituted or unsubstituted C$_{1-6}$-alkyl; a saturated or unsaturated, linear or branched, substituted or unsubstituted —O—C$_{1-6}$-alkyl (alkoxy); a saturated or unsaturated, linear or branched, substituted or unsubstituted —S—C$_{1-6}$-alkyl; a saturated or unsaturated, linear or branched, substituted or unsubstituted —C(O)—C$_{1-6}$-alkyl-group; a saturated or unsaturated, linear or branched, substituted or unsubstituted —C(O)—O—C$_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being R$_c$ one of R$_{11}$, R$_{12}$ or $R_8$, (being $R_c'$ one of $R_{11'}$, $R_{12'}$ or $R_{8'}$; being $R_{c''}$ one of $R_{11''}$, $R_{12''}$ or $R_{8''}$; being $R_{c'''}$ one of $R_{11'''}$, $R_{12'''}$ or $R_{8'''}$), wherein $R_1$ to $R_{14'''}$ are as defined in the description, and wherein when different radicals $R_1$ to $R_{14'''}$ are present simultaneously in Formula I they may be identical or different.

Most preferably in connection with aryl (including alkylaryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) by one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$, $R_{12}$ or $R_8$, (being $R_{c'}$ one of $R_{11'}$, $R_{12'}$ or $R_{8'}$; being $R_{c''}$ one of $R_{11''}$, $R_{12''}$ or $R_{8''}$; being $R_{c'''}$ one of $R_{11'''}$, $R_{12'''}$ or $R_{8'''}$), wherein $R_1$ to $R_{14'''}$ are as defined in the description, and wherein when different radicals $R_1$ to $R_{14'''}$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl by

or =O;

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated —especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general formula I is a compound wherein n is 0 or 1;

$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, —C(O)$R_6$, —C(O)CH$_2$OR$_6$, —C(O)CH$_2$OC(O)R$_6$, —C(O)OR$_6$, —C(O)NR$_6$R$_{6'}$ or —S(O)$_2$R$_6$;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl and substituted or unsubstituted alkyheterocylcyl;

wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —OCH$_2$CH$_2$OH, NR$_{11}$S(O)$_2$NR$_{11'}$R$_{11''}$, and C(CH$_3$)$_2$OR$_{11}$;

additionally, cycloalkyl or non-aromatic heterocyclyl in $R_1$ or $R_6$, also in alkylcycloalkyl and alkylheterocyclyl, if substituted, may also be substituted with

or =O;

wherein the alkyl, alkylene or alkynyl in $R_1$ or $R_6$, if substituted, is substituted with one or more substituent/s selected from —OR$_{11}$, halogen, —CN, haloalkyl, haloalkoxy, —SR$_{11}$, —S(O)R$_{11}$, and —S(O)$_2$R$_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

wherein said cycloalkyl, aryl or heterocyclyl in $R_2$, also in alkylaryl, alkylcycloalkyl and alkylheterocyclyl, if substituted, is substituted with one or more substituent/s selected from halogen, —$R_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, —OCH$_2$CH$_2$OH, —NR$_{12}$S(O)$_2$NR$_{12'}$R$_{12''}$, and C(CH$_3$)$_2$OR$_{12}$;

additionally, cycloalkyl or non-aromatic heterocyclyl in $R_2$, also in alkylcycloalkyl and alkylheterocyclyl, if substituted, may also be substituted with

or =O;

wherein the alkyl, alkylene or alkynyl in $R_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;

wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

X is selected from —CR$_x$R$_{x'}$—, —CR$_x$OR$_{14'}$, —CR$_x$R$_{x'}$NR$_7$—, —CR$_x$R$_{x'}$O—, —CR$_x$R$_{x'}$NR$_7$C(O)—, —C(O)—, —CR$_x$R$_{x'}$C(O)—, —C(O)O—, —C(O)NR$_7$—, —CR$_x$R$_{x'}$C(O)NR$_7$— and —C(O)NR$_7$CR$_x$R$_{x'}$—;

wherein $R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc;

$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{14}$, —C(O)NR$_{14}$R$_{14'}$, —NR$_{14}$C(O)R$_{14'}$, and —NR$_{14}$R$_{14''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively if X is —CR$_x$R$_{x'}$—, $R_x$ and $R_{x'}$ may form, together with the carbon atom to which they are attached, a substituted or unsubstituted heterocyclyl, or a substituted or unsubstituted cycloalkyl;

$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is selected from hydrogen, halogen, —$R_9$, —OR$_9$, —NO$_2$, —NR$_9$R$_{9''''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_{9'}$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_{9'}$R$_{9''}$, —OCOR$_9$, and C(CH$_3$)$_2$OR$_9$;

$R_{3'}$, $R_{3''}$ and $R_{3'''}$ are independently selected from hydrogen, halogen, —$R_9$, —OR$_9$, —NO$_2$, —NR$_9$R$_{9''''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_{9'}$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_{9'}$R$_{9''}$, —OCOR$_9$, and C(CH$_3$)$_2$OR$_9$;

wherein $R_9$, $R_{9'}$, and $R_{9''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ is selected from hydrogen, $-OR_{13}$, substituted or unsubstituted $C_{1-6}$ alkyl, substituted or unsubstituted $C_{2-6}$ alkenyl, substituted or unsubstituted $C_{2-6}$ alkynyl, $-C(O)OR_{13}$, $-C(O)NR_{13}R_{13'}$, $-NR_{13}C(O)R_{13'}$, $-NR_{13}R_{13'''}$, $-NC(O)OR_{13}$, and substituted or unsubstituted heterocyclyl;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein the alkyl, alkylene or alkynyl, other than those defined in $R_1$, $R_2$ or $R_6$, if substituted, is substituted with one or more substituent/s selected from $-OR_{10}$, halogen, $-CN$, haloalkyl, haloalkoxy, $-SR_{10}$, $-S(O)R_{10}$, and $-S(O)_2R_{10}$;

wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

wherein the aryl, heterocyclyl or cycloalkyl, also in alkylaryl, alkylcycloalkyl and alkylheterocyclyl, other than those defined in $R_1$, $R_2$ or $R_6$, if substituted, is substituted with one or more substituent/s selected from halogen, $-R_8$, $-OR_8$, $-NO_2$, $-NR_8R_{8'''}$, $NR_8C(O)R_{8'}$, $-NR_8S(O)_2R_{8'}$, $-S(O)_2NR_8R_{8'}$, $-NR_8C(O)NR_8R_{8''}$, $-SR_8$, $-S(O)R_8$, $S(O)_2R_8$, $-CN$, haloalkyl, haloalkoxy, $-C(O)OR_8$, $-C(O)NR_8R_{8'}$, $-OCH_2CH_2OH$, $-NR_8S(O)_2NR_{8'}R_{8''}$ and $C(CH_3)_2OR_8$;

additionally, wherein cycloalkyl or non-aromatic heterocyclyl, other than those defined in $R_1$, $R_2$ or $R_6$, also in alkylcycloalkyl and alkylheterocyclyl, if substituted, may also be substituted with

or =O;

wherein $R_8$, $R_{8'}$, and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein the alkylaryl is an aryl group connected to another atom through 1 to 4 $-CH_2-$ groups.

In a further embodiment the compound according to the invention of general formula I is a compound wherein the alkylheterocyclyl is an heterocyclyl group connected to another atom through 1 to 4 $-CH_2-$ groups.

In a further embodiment the compound according to the invention of general formula I is a compound wherein the alkylcycloalkyl is a cycloalkyl group connected to another atom through 1 to 4 $-CH_2-$ groups.

In a further embodiment the compound according to the invention of general formula I is a compound wherein
n is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, $-C(O)R_6$, $-C(O)CH_2OR_6$, $-C(O)CH_2OC(O)R_6$, $-C(O)OR_6$, $-C(O)NR_6R_{6'}$ or $-S(O)_2R_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted $C_{1-6}$ alkyl, substituted or unsubstituted alkylaryl, substituted or unsubstituted alkylheterocyclyl, $-C(O)NR_6R_{6'}$, $-C(O)R_6$ or $-S(O)_2R_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, or substituted or unsubstituted alkylcycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein $R_1$ is —C(O)$R_6$, —C(O)O$R_6$, —C(O)CH$_2$O$R_6$, —C(O)CH$_2$OC(O)$R_6$, —C(O)N$R_6R_6'$, or —S(O)$_2R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is —C(O)$R_6$ or —S(O)$_2R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted $C_{1-6}$ alkyl, substituted or unsubstituted $C_{2-6}$ alkenyl, or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted $C_{1-6}$ alkyl.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted cycloalkyl, substituted or unsubstituted aryl or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted alkylaryl, substituted or unsubstituted alkylheterocyclyl or substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is hydrogen, substituted or unsubstituted $C_{1-6}$ alkyl, substituted or unsubstituted cycloalkyl, substituted or unsubstituted aryl, substituted or unsubstituted heterocyclyl, substituted or unsubstituted alkylcycloalkyl or substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is hydrogen, substituted or unsubstituted $C_{1-6}$ alkyl, substituted or unsubstituted $C_{2-6}$ alkenyl, or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is substituted or unsubstituted cycloalkyl, substituted or unsubstituted aryl, or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is substituted or unsubstituted alkylcycloalkyl, substituted or unsubstituted alkylaryl, or substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is selected from —$CR_xR_{x'}$—, —$CR_xOR_{14'}$—, —$CR_xR_xNR_7$—, —$CR_xR_xO$—, —$CR_xR_xNR_7C(O)$—, —$C(O)$—, —$CR_xR_xC(O)$—, —$C(O)O$—, —$C(O)NR_7$—, —$CR_xR_xC(O)NR_7$— and —$C(O)NR_7CR_xR_{x'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is selected from —$CR_xR_{x'}$;— —$CR_xOR_{14'}$—, —$CR_xR_xNR_7$—, —$NR_7CR_xR_{x'}$—, —$CR_xR_xO$—, —$OCR_xR_{x'}$—, —$CR_xR_xNR_7C(O)$—, —$NR_7C(O)CR_xR_{x'}$—, —$C(O)$—, —$CR_xR_xC(O)$—, —$C(O)O$—, —$OC(O)$—, —$C(O)NR_7$—, —$NR_7C(O)$—, —$CR_xR_xC(O)NR_7$— and —$C(O)NR_7CR_xR_x$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is selected from —$CR_xR_{x'}$—, —$CR_xOR_{14'}$—, —$CR_xR_xNR_7$—, —$CR_xR_xO$—, —$CR_xR_xNR_7C(O)$—, —$C(O)$—, —$C(O)NR_7$— and —$CR_xR_xC(O)NR_7$— optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$CR_xR_xNR_7$—, or $CR_xR_xO$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$CR_xR_{x'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$CR_xOR_{14'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$C(O)$—, —$CR_xR_xC(O)$— or —$C(O)O$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In another preferred embodiment of the compound according to the invention of general formula I is a compound wherein X is selected from —$CR_xR_xNR_7C(O)$—, —$C(O)NR_7$—, —$CR_xR_xC(O)NR_7$— and —$C(O)NR_7CRxR_x$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_{14}$, —$C(O)NR_{14}R_{14'}$—$NR_{14}C(O)R_{14'}$, and —$NR_{14}R_{14'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively if X is —$CR_xR_{x'}$—, $R_x$ and $R_{x'}$ may form, together with the carbon atom to which they are attached, a substituted or unsubstituted heterocyclyl, or a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is $CR_xOR_{14'}$ and $R_{14'}$ is selected from hydrogen, unsubstituted $C_{1-6}$ alkyl, unsubstituted $C_{2-6}$ alkenyl, substituted or unsubstituted $C_{2-6}$ alkynyl, or unsubstituted acetyl;

$R_x$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_{14}$, —$C(O)NR_{14}R_{14'}$—$NR_{14}C(O)R_{14'}$, and —$NR_{14}R_{14'''}$, preferably $R_x$ is selected from hydrogen, substituted or unsubstituted $C_{1-6}$ alkyl, —C(O)OR$_{14}$, —C(O)NR$_{14}$R$_{14'}$, —NR$_{14}$C(O)R$_{14'}$, and —NR$_{14}$R$_{14'''}$; more preferably $R_x$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl, preferably $R_{x'}$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein alternatively if X is —CR$_x$R$_{x'}$—, R$_x$ and R$_{x'}$ may form, together with the carbon atom to which they are attached, a substituted or unsubstituted heterocyclyl, or a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{14}$, —C(O)NR$_{14}$R$_{14'}$—NR$_{14}$C(O)R$_{14'}$, and —NR$_{14}$R$_{14'''}$, preferably $R_x$ is selected from hydrogen, substituted or unsubstituted $C_{1-6}$ alkyl, —C(O)OR$_{14}$, —C(O)NR$_{14}$R$_{14'}$, —NR$_{14}$C(O)R$_{14'}$, and —NR$_{14}$R$_{14'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_x$ is selected from —C(O)OR$_{14}$, —C(O)NR$_{14}$R$_{14'}$ and —NR$_{14}$C(O)R$_{14'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9''}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is selected from hydrogen, halogen and —OR$_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{3''}$, $R_{3'''}$ and $R_{3''''}$ are independently selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is selected from hydrogen, halogen, —R$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9''}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_4$ is selected from hydrogen, —OR$_{13}$, substituted or unsubstituted $C_{1-6}$ alkyl, substituted or unsubstituted $C_{2-6}$ alkenyl, substituted or unsubstituted $C_{2-6}$ alkynyl, —C(O)OR$_{13}$, —C(O)NR$_{13}$R$_{13'}$, —NR$_{13}$C(O)R$_{13'}$, —NR$_{13}$R$_{13'''}$, —NC(O)OR$_{13}$, and substituted or unsubstituted heterocyclyl;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;
wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;
and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_4$ is selected from hydrogen, —$OR_{13}$, substituted or unsubstituted $C_{1-6}$ alkyl, substituted or unsubstituted $C_{2-6}$ alkenyl, substituted or unsubstituted $C_{2-6}$ alkynyl, —$C(O)OR_{13}$, —$C(O)NR_{13}R_{13'}$, —$NR_{13}C(O)R_{13'}$, —$NR_{13}R_{13'''}$, —$NC(O)OR_{13}$, and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_4$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{4'}$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_5$ and $R_{5'}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl and substituted or unsubstituted alkyheterocylcyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_6$ and $R_{6'}$ are independently selected from hydrogen, substituted or unsubstituted $C_{1-6}$ alkyl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_7$ is selected from hydrogen, substituted or unsubstituted $C_{1-6}$ alkyl and Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl, preferably $R_8$, $R_{8'}$ and $R_{8''}$ are independently selected from hydrogen, unsubstituted $C_{1-6}$ alkyl, unsubstituted aryl, unsubstituted alkylaryl, unsubstituted cycloalkyl and unsubstituted alkylcycloalkyl, unsubstituted heterocyclyl and unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{8'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen, unsubstituted $C_{1-6}$ alkyl and unsubstituted acetyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl and unsubstituted acetyl, preferably $R_9$, $R_{9'}$ and $R_{9''}$ are independently selected from hydrogen, unsubstituted $C_{1-6}$ alkyl and unsubstituted acetyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{9'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, and $R_{10'}$ are independently selected from hydrogen, and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{11'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12}$, $R_{12'}$ and $R_{12''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{12'''}$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl, preferably $R_{13}$, $R_{13'}$ and $R_{13''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{13'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{13'''}$ is selected from hydrogen, unsubstituted $C_{1-6}$ alkyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl, preferably $R_{14}$, $R_{14'}$ and $R_{14''}$ are independently selected from hydrogen, unsubstituted $C_{1-6}$ alkyl and unsubstituted acetyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_{14'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{14'''}$ is selected from hydrogen and unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
X is, —$CR_xR_{x'}$, —$CR_xOR_{14'}$, —$CR_xR_xNR_7$—, or $CR_xR_xO$—, and
$R_1$ is —$C(O)R_6$ or —$S(O)_2R_6$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
X is, —$CR_xR_{x'}$, —$CR_xOR_{14'}$; —$CR_xR_xNR_7$—, or $CR_xR_xO$—, and
$R_1$ is substituted or unsubstituted $C_{1-6}$ alkyl, substituted or unsubstituted $C_{2-6}$ alkenyl, substituted or unsubstituted $C_{2-6}$ alkynyl, preferably $R_1$ is substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
X is, —$CR_xR_{x'}$, —$CR_xOR_{14'}$; —$CR_xR_xNR_7$—, or $CR_xR_xO$—, and
$R_1$ is substituted or unsubstituted alkylaryl, substituted or unsubstituted alkylheterocyclyl, substituted or unsubstituted alkylcycloalkyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
X is —$C(O)NR_7$—, and
$R_1$ is substituted or unsubstituted $C_{1-6}$ alkyl, substituted or unsubstituted $C_{2-6}$ alkenyl, substituted or unsubstituted $C_{2-6}$alkynyl, preferably $R_1$ is substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
X is —$C(O)$—,
$R_1$ is substituted or unsubstituted $C_{1-6}$ alkyl, substituted or unsubstituted $C_{2-6}$ alkenyl, substituted or unsubstituted $C_{2-6}$alkynyl, preferably $R_1$ is substituted or unsubstituted $C_{1-6}$ alkyl, and
$R_2$ is substituted or unsubstituted heterocyclyl, wherein the heterocyclyl contains, at least, one nitrogen attached to the carbonyle group in X;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —CR$_x$R$_{x'}$— or —CR$_x$OR$_{14}$; and
R$_2$ is hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, or substituted or unsubstituted heterocyclyl, preferably R$_2$ is hydrogen, substituted or unsubstituted C$_{1-6}$ alkyl, substituted or unsubstituted cycloalkyl, substituted or unsubstituted aryl, or substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —CR$_x$R$_{x'}$— or —CR$_x$OR$_{14}$;
R$_2$ is hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, or substituted or unsubstituted heterocyclyl, preferably R$_2$ is hydrogen, substituted or unsubstituted C$_{1-6}$ alkyl, substituted or unsubstituted cycloalkyl, substituted or unsubstituted aryl, or substituted or unsubstituted heterocyclyl; and
R$_1$ is —C(O)R$_6$ or —S(O)$_2$R$_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein R$_1$ is substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, —C(O)R$_6$, —C(O)CH$_2$OR$_6$, —C(O)CH$_2$OC(O)R$_6$, —C(O)OR$_6$, —C(O)NR$_6$R$_{6'}$ or —S(O)$_2$R$_6$;
wherein
the alkyl is C$_{1-6}$ alkyl like methyl, ethyl, propyl, butyl, pentyl or hexyl;
and/or
the C$_{1-6}$ alkyl is preferably selected from methyl, ethyl, propyl, butyl, pentyl, hexyl, isopropyl, or 2-methylpropyl, more preferably the C$_{1-6}$ alkyl is methyl or ethyl;
and/or
the C$_{2-6}$-alkenyl, is preferably selected from ethylene, propylene, butylene, pentylene or hexylene;
and/or
the C$_{2-6}$-alkynyl is preferably selected from ethyne, propyne, butyne, pentyne or hexyne;
and/or
the aryl is selected from phenyl, naphtyl, or anthracene; preferably is napthyl and phenyl; more preferably is phenyl;

and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is thiazole;
and/or
the cycloalkyl is C$_{3-8}$ cycloalkyl like cyclopropyl, cyclobutyl, cyclopentyl, cyclohexyl, cycloheptyl, or cyclooctyl; preferably is C$_{3-7}$ cycloalkyl like cyclopropyl, cyclobutyl, cyclopentyl, cyclohexyl, or cycloheptyl; more preferably from C$_{3-6}$ cycloalkyl like cyclopropyl, cyclobutyl, cyclopentyl or cyclohexyl;
and/or
R$_2$ is hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
wherein
the alkyl is C$_{1-6}$ alkyl like methyl, ethyl, propyl, butyl, pentyl or hexyl;
and/or
the C$_{1-6}$ alkyl is preferably selected from methyl, ethyl, propyl, butyl, pentyl, hexyl, isopropyl, 2-methylpropyl, isopentyl or 3-pentanyl, more preferably the C$_{1-6}$ alkyl is methyl, ethyl, propyl, isopropyl, isobutyl, isopentyl or 3-pentanyl;
and/or
the C$_{2-6}$-alkenyl, is preferably selected from ethylene, propylene, butylene, pentylene or hexylene;
and/or
the C$_{2-6}$-alkynyl is preferably selected from ethyne, propyne, butyne, pentyne or hexyne;
and/or
the aryl is selected from phenyl, naphtyl, or anthracene; preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine, morpholine, tetrahydropyrane, oxazepan or pyrrolidine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{14}$, —C(O)NR$_{14}$R$_{14'}$, —NR$_{14}$C(O)R$_{14'}$, and —NR$_{14}$R$_{14'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively if X is —CR$_x$R$_{x'}$, R$_x$ and R$_{x'}$ may form, together with the carbon atom to which they are attached, a substituted or unsubstituted heterocyclyl, or a substituted or unsubstituted cycloalkyl;

wherein the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine or tetrahydropyrane, and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl or cyclohexyl;

and/or $R_3$ is selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

and/or $R_{3'}$, $R_{3''}$ and $R_{3'''}$ are independently selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9''}$, —OCOR$_9$, and C(CH$_3$)$_2$OR$_9$;

wherein the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_4$ is selected from hydrogen, —OR$_{13}$, substituted or unsubstituted $C_{1-6}$ alkyl, substituted or unsubstituted $C_{2-6}$ alkenyl, substituted or unsubstituted $C_{2-6}$ alkynyl, —C(O)OR$_{13}$, —C(O)NR$_{13}$R$_{13'}$, —NR$_{13}$C(O)R$_{13'}$, —NR$_{13}$R$_{13'''}$, —NC(O)OR$_{13}$, and substituted or unsubstituted heterocyclyl;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;
wherein
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl and substituted or unsubstituted alkyheterocylcyl; wherein
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl, ethyl or isopropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene, preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is furane;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc; wherein
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl, ethyl, propyl, isopropyl, isobutyl or 3-pentanyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
$R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkheterocylcyl;
$R_{8'''}$ is selected from hydrogen, unsubstituted $C_{1-6}$ alkyl, unsubstituted $C_{2-6}$ alkenyl, unsubstituted $C_{2-6}$ alkynyl and -Boc; wherein
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

$R_{11'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

$R_{12'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl, is preferably selected from ethylene, propylene, butylene, pentylene or hexylene;

and/or the $C_{2-6}$-alkynyl is preferably selected from like ethyne, propyne, butyne, pentyne or hexyne;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl, is preferably selected from like ethylene, propylene, butylene, pentylene or hexylene;

and/or the $C_{2-6}$-alkynyl is preferably selected from ethyne, propyne, butyne, pentyne or hexyne;

and/or n is 0 or 1, preferably n is 1 and/or

X is —$CR_xR_x$,—; —$CR_xOR_{14'}$, —$CR_xR_xNR_7$—, —$CR_xR_xO$—, —$CR_xR_xNR_7C(O)$—, —$C(O)$—, —$C(O)O$—, —$C(O)NR_7$—, —$CR_xR_xC(O)NR_7$— or —$C(O)NR_7CR_xR_x$; preferably X is —$CR_xR_x$,—; —$CR_xOR_{14'}$, —$CR_xR_xNR_7$—, —$CR_xR_xO$—, —$CR_xR_xNR_7C(O)$—, —$C(O)$—, —$C(O)NR_7$—, or —$CR_xR_xC(O)NR_7$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_1$ as defined in any of the embodiments, the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or ethyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is thiazole;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_2$ as defined in any of the embodiments,
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl, ethyl, propyl, isopropyl, isobutyl, isopentyl or 3-pentanyl;
and/or
the $C_{2-6}$-alkenyl is preferably selected from like ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene; preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine, morpholine, tetrahydropyrane, oxazepan or pyrrolidine;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_x$ or $R_{x'}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine or tetrahydropyrane,
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_3$, $R_{3''}$, $R_{3'''}$, or $R_{3''''}$ as defined in any of the embodiments,
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl;
and/or
the $C_{2-6}$-alkenyl is preferably selected from like ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_4$ or $R_{4'}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_5$ or $R_{5''}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
in $R_6$ as defined in any of the embodiments,
the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl, ethyl or isopropyl;
and/or
the $C_{2-6}$-alkenyl is preferably selected from like ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene, preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazinebenzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is furane;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_7$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl, ethyl, propyl, isopropyl, isobutyl or 3-pentanyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_8$, $R_{8'}$, $R_{8''}$ or $R_{8'''}$ as defined in any of the embodiments, the alkyl is $C_{1-6}$ alkyl like methyl, ethyl, propyl, butyl, pentyl or hexyl;
and/or
the $C_{1-6}$ alkyl is preferably selected from methyl, ethyl, propyl, butyl, pentyl, hexyl, isopropyl, 2-methylpropyl, isopentyl or 3-pentanyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_9$, $R_{9'}$, $R_{9''}$ or $R_{9'''}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{10}$ or $R_{10'}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl;
and/or
the $C_{2-6}$-alkenyl is preferably selected from ethylene, propylene, butylene, pentylene or hexylene;
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{11}$, $R_{11'}$, $R_{11''}$ or $R_{11'''}$ as defined in any of the embodiments,
the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{12}$, $R_{12'}$, $R_{12''}$, or $R_{12'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl, more preferably the $C_{1-6}$ alkyl is methyl;

and/or the $C_{2-6}$-alkenyl is preferably selected from like ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{13}$, $R_{13'}$, $R_{13''}$ or $R_{13'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{14}$, $R_{14'}$, $R_{14''}$ or $R_{14'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein n is 0 or 1, preferably n is 1 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein X is $-CR_xR_{x'}$; $-CR_xOR_{14'}$, $-CR_xR_{x'}NR_7-$, $-CR_xR_{x'}O-$, $-CR_xR_{x'}NR_7C(O)-$, $-C(O)-$, $-C(O)O-$, $-C(O)NR_7-$, $-CR_xR_{x'}C(O)NR_7-$ or $-C(O)NR_7CR_xR_{x'}$; preferably X is $-CR_xR_{x'}$; $-CR_xOR_{14'}$, $-CR_xR_{x'}NR_7-$, $-CR_xR_{x'}O-$, $-CR_xR_{x'}NR_7C(O)-$, $-C(O)-$, $-C(O)NR_7-$, or $-CR_xR_{x'}C(O)NR_7-$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment $R_1$ is a substituted or unsubstituted group selected from methyl, ethyl, benzyl, —CH2-thiazole, —S(O)$_2$-methyl, —C(O)CF$_3$, —C(O)CH$_2$OC(O)CH$_3$, acetyl, —C(O)-furane, —C(O)— isopropyl, —C(O)-ethyl, —C(O)CH$_2$OCH$_3$, —C(O)CH$_2$O-benzyl, —C(O)CH$_2$OH, —CH$_2$CH$_2$OCH$_3$, —CH$_2$CH$_2$OH, —C(O)NH-ethyl and —CH$_2$CF$_3$.

In another preferred embodiment $R_1$ is substituted or unsubstituted methyl, substituted or unsubstituted acetyl, substituted or unsubstituted —CH$_2$CH$_2$OH or substituted or unsubstituted CH$_2$CF$_3$.

In a most preferred embodiment $R_1$ is substituted or unsubstituted methyl or substituted or unsubstituted acetyl.

In a preferred embodiment $R_2$ is a substituted or unsubstituted group selected from hydrogen, methyl, ethyl, propyl, isopropyl, isobutyl, isopentyl, 3-pentanyl, cyclopropyl, —CH$_2$-cyclopropyl, phenyl, benzyl, pyridine, pyrimidine, piperidine, morpholine, thiomorpholine, tetrahydropyrane, oxazepan and pyrrolidine.

In a preferred embodiment $R_2$ is hydrogen, substituted or unsubstituted methyl, substituted or unsubstituted ethyl, substituted or unsubstituted isopropyl, substituted or unsubstituted isobutyl, substituted or unsubstituted phenyl, substituted or unsubstituted pyridine, substituted or unsubstituted pyrimidine, substituted or unsubstituted piperidine, substituted or unsubstituted morpholine, substituted or unsubstituted thiomorpholine or substituted or unsubstituted pyrrolidine.

In another preferred embodiment $R_2$ is hydrogen, substituted or unsubstituted methyl, substituted or unsubstituted ethyl, substituted or unsubstituted isopropyl, substituted or unsubstituted phenyl, substituted or unsubstituted pyridine, substituted or unsubstituted piperidine, or substituted or unsubstituted morpholine.

In a preferred embodiment $R_3$ is hydrogen, chlorine, hydroxyl, substituted or unsubstituted methoxy or substituted or unsubstituted —O-acetyl.

In another preferred embodiment $R_3$ is hydrogen or hydroxyl.

In particular preferred embodiment
$R_3$ is hydrogen.
In particular preferred embodiment
$R_{3'}$, $R_{3''}$ and $R_{3'''}$ are all hydrogen.
In another particular preferred embodiment
$R_3$ is hydrogen or hydroxyl while $R_{3'}$, $R_{3''}$ and $R_{3'''}$ are hydrogen.
In another particular preferred embodiment
$R_3$ $R_{3'}$, $R_{3''}$ and $R_{3'''}$ are all hydrogen.
In a preferred embodiment
$R_4$ is hydrogen or substituted or unsubstituted methyl.
In another preferred embodiment
$R_4$ is hydrogen.
In a preferred embodiment
$R_{4'}$ is hydrogen or substituted or unsubstituted methyl.
In another preferred embodiment
$R_{4'}$ is hydrogen.
In another particular preferred embodiment
$R_4$ and $R_{4'}$ are both hydrogen.
In a preferred embodiment
$R_5$ is hydrogen or substituted or unsubstituted methyl.
In another preferred embodiment
$R_5$ is hydrogen.
In a preferred embodiment
$R_{5'}$ is hydrogen.
In another particular preferred embodiment
$R_5$ and $R_{5'}$ are both hydrogen.
In a preferred embodiment
$R_6$ and $R_{6'}$ are independently selected from hydrogen, substituted or unsubstituted methyl, substituted or unsubstituted ethyl, substituted or unsubstituted isopropyl, —$CF_3$, substituted or unsubstituted-$CH_2OCH_3$, substituted or unsubstituted —$CH_2OH$, and substituted or unsubstituted furane.
In another preferred embodiment
$R_6$ is hydrogen, substituted or unsubstituted methyl, substituted or unsubstituted ethyl, substituted or unsubstituted isopropyl, —$CF_3$, substituted or unsubstituted-$CH_2OCH_3$, substituted or unsubstituted —$CH_2OH$ or substituted or unsubstituted furane.
In another preferred embodiment
$R_6$ is substituted or unsubstituted methyl.
In another preferred embodiment
$R_{6'}$ is hydrogen or substituted or unsubstituted ethyl.
In another preferred embodiment
$R_{6'}$ is substituted or unsubstituted ethyl.
In another preferred embodiment
$R_6$ is hydrogen while $R_{6'}$ is substituted or unsubstituted ethyl.
In a preferred embodiment
$R_7$ is hydrogen, substituted or unsubstituted methyl, substituted or unsubstituted ethyl, substituted or unsubstituted propyl, substituted or unsubstituted isopropyl, substituted or unsubstituted isobutyl, 3-pentanyl or -Boc.
In a preferred embodiment
$R_7$ is substituted or unsubstituted methyl, substituted or unsubstituted ethyl, or substituted or unsubstituted isopropyl.
In a preferred embodiment
$R_7$ is substituted or unsubstituted methyl.
In another preferred embodiment
$R_9$ is hydrogen, substituted or unsubstituted methyl or unsubstituted acetyl.
In another preferred embodiment
$R_{11}$ is hydrogen or substituted or unsubstituted methyl.
In another preferred embodiment
$R_{12}$ is hydrogen or substituted or unsubstituted methyl.

In another preferred embodiment
$R_{12'}$, $R_{12''}$ or $R_{12'''}$ are all hydrogen.
In another preferred embodiment
$R_{12'}$ is hydrogen.
In another preferred embodiment
$R_{12'''}$ is hydrogen.
In another preferred embodiment
$R_{12}$ and $R_{12'''}$ are both hydrogen.
In another preferred embodiment
$R_{12}$ is substituted or unsubstituted methyl and $R_{12'}$ is hydrogen.
In another preferred embodiment
$R_{14}$ is hydrogen or unsubstituted acetyl.
In another preferred embodiment
$R_{14}$ is hydrogen.
In another preferred embodiment
$R_{14'}$ is hydrogen or unsubstituted acetyl.
In another preferred embodiment
$R_{14'}$ is hydrogen.
In a preferred embodiment
$R_x$ is hydrogen or a substituted or unsubstituted methyl.
In a preferred embodiment
$R_{x'}$ is hydrogen;
In a preferred embodiment
$R_x$ is hydrogen or a substituted or unsubstituted methyl while $R_{x'}$ is hydrogen.
In a preferred embodiment
$R_x$ and $R_{x'}$ are both hydrogen;
In a preferred embodiment
$R_x$ and $R_{x'}$ form together with the carbon atom to which they are attached, a substituted or unsubstituted group selected from tetrahydropyrane, pyridine, cyclopropyl or cyclohexyl;
In a preferred embodiment
X is —$CR_xOR_{14'}$ and
$R_x$ is hydrogen, or a substituted or unsubstituted methyl, preferably hydrogen, while $R_{14'}$ is hydrogen or acetyl, preferably hydrogen.
In another preferred embodiment
n is 1.
In another preferred embodiment
X is substituted or unsubstituted —$CH_2NR_7$—, substituted or unsubstituted —$CH_2O$—, —C(O)—, —$C(O)NR_7$—, substituted or unsubstituted —$CH_2CH_2C(O)NR_7$—, substituted or unsubstituted —CH(OH)—, substituted or unsubstituted —CH(O-acetyl)-, substituted or unsubstituted —$CH_2$—, substituted or unsubstituted —CH(methyl)-, substituted or unsubstituted —$CH_2C(O)NR_7$— or substituted or unsubstituted —$CH_2NR_7C(O)$—;
wherein
$R_7$ is hydrogen, substituted or unsubstituted methyl, substituted or unsubstituted ethyl, substituted or unsubstituted propyl, substituted or unsubstituted isopropyl, substituted or unsubstituted isobutyl, substituted or unsubstituted 3-pentanyl or -Boc.
In another preferred embodiment
X is substituted or unsubstituted —$CH2O$—, —C(O)—, —$C(O)NR_7$— or substituted or unsubstituted —$CH_2$—;
wherein
$R_7$ is hydrogen, substituted or unsubstituted methyl, substituted or unsubstituted ethyl, substituted or unsubstituted propyl, substituted or unsubstituted isopropyl, substituted or unsubstituted isobutyl or substituted or unsubstituted 3-pentanyl.
In an particular embodiment
the halogen is fluorine, chlorine, iodine or bromine.
In an particular embodiment
the halogen is fluorine or chlorine.
In a preferred further embodiment, the compounds of the general formula I are selected from

| EX | Chemical name |
|---|---|
| 1 | 1-(1'-phenethyl-3,4-dihydro-2H-spiro[isoquinoline-1,4'-piperidine]-2-yl)ethanone |
| 2 | 2-methyl-1-(1'-phenethyl-3,4-dihydro-2H-spiro[isoquinoline-1,4'-piperidine]-2-yl)propan-1-one |
| 3 | furan-2-yl(1'-phenethyl-3,4-dihydro-2H-spiro[isoquinoline-1,4'-piperidine]-2-yl)methanone |
| 4 | 1-(1'-phenethyl-3,4-dihydro-2H-spiro[isoquinoline-1,4'-piperidine]-2-yl)propan-1-one |
| 5 | 2-methoxy-1-(1'-phenethyl-3,4-dihydro-2H-spiro[isoquinoline-1,4'-piperidine]-2-yl)ethanone |
| 6 | 2-(benzyloxy)-1-(1'-phenethyl-3,4-dihydro-2H-spiro[isoquinoline-1,4'-piperidine]-2-yl)ethanone |
| 7 | 1-(6-methoxy-1'-phenethyl-3,4-dihydro-2H-spiro[isoquinoline-1,4'-piperidine]-2-yl)ethanone |
| 8 | 1-(1'-(2-morpholinoethyl)-3,4-dihydro-2H-spiro[isoquinoline-1,4'-piperidine]-2-yl)ethanone |
| 9 | 1-(1'-((tetrahydro-2H-pyran-4-yl)methyl)-3,4-dihydro-2H-spiro[isoquinoline-1,4'-piperidine]-2-yl)ethanone |
| 10 | 1-(1'-(2-(methyl(phenyl)amino)ethyl)-3,4-dihydro-2H-spiro[isoquinoline-1,4'-piperidine]-2-yl)ethanone |
| 11 | 1-(1'-(2-isopropoxyethyl)-3,4-dihydro-2H-spiro[isoquinoline-1,4'-piperidine]-2-yl)ethanone |
| 12 | 1-(1'-isobutyl-3,4-dihydro-2H-spiro[isoquinoline-1,4'-piperidine]-2-yl)ethanone |
| 13 | 1-(1'-(cyclohexylmethyl)-3,4-dihydro-2H-spiro[isoquinoline-1,4'-piperidine]-2-yl)ethanone |
| 14 | 1-(1'-(2-(piperidin-1-yl)ethyl)-3,4-dihydro-2H-spiro[isoquinoline-1,4'-piperidine]-2-yl)ethanone |
| 15 | 1-(1'-isopentyl-3,4-dihydro-2H-spiro[isoquinoline-1,4'-piperidine]-2-yl)ethanone |
| 16 | 1-(1'-(2-(benzyl(methyl)amino)ethyl)-3,4-dihydro-2H-spiro[isoquinoline-1,4'-piperidine]-2-yl)ethanone |
| 17 | 1-(1'-(pyridin-2-ylmethyl)-3,4-dihydro-2H-spiro[isoquinoline-1,4'-piperidine]-2-yl)ethanone |
| 18 | 1-(1'-(2-(pyridin-2-yl)ethyl)-3,4-dihydro-2H-spiro[isoquinoline-1,4'-piperidine]-2-yl)ethanone |
| 19 | 1-(1'-(2-(pyridin-3-yl)ethyl)-3,4-dihydro-2H-spiro[isoquinoline-1,4'-piperidine]-2-yl)ethanone |
| 20 | 1-(1'-(2-phenoxyethyl)-3,4-dihydro-2H-spiro[isoquinoline-1,4'-piperidine]-2-yl)ethanone |
| 21 | 1-(1'-(2-(pyridin-4-yl)ethyl)-3,4-dihydro-2H-spiro[isoquinoline-1,4'-piperidine]-2-yl)ethanone |
| 22 | 3-(2-acetyl-3,4-dihydro-2H-spiro[isoquinoline-1,4'-piperidine]-1'-yl)-N,N-dimethylpropanamide |
| 23 | 1-(1'-(2-(6-(trifluoromethyl)pyridin-3-yl)ethyl)-3,4-dihydro-2H-spiro[isoquinoline-1,4'-piperidine]-2-yl)ethanone |
| 24 | 1-(1'-(2-ethoxyethyl)-3,4-dihydro-2H-spiro[isoquinoline-1,4'-piperidine]-2-yl)ethanone |
| 25 | 1-(1'-(2-(2-(trifluoromethyl)pyridin-4-yl)ethyl)-3,4-dihydro-2H-spiro[isoquinoline-1,4'-piperidine]-2-yl)ethanone |
| 26 | 1-(1'-(2-(3-fluoropyridin-4-yl)ethyl)-3,4-dihydro-2H-spiro[isoquinoline-1,4'-piperidine]-2-yl)ethanone |
| 27 | 1-(1'-(2-(5-chloropyridin-3-yl)ethyl)-3,4-dihydro-2H-spiro[isoquinoline-1,4'-piperidine]-2-yl)ethanone |
| 28 | 4-(2-(2-acetyl-3,4-dihydro-2H-spiro[isoquinoline-1,4'-piperidine]-1'-yl)ethyl)picolinonitrile |
| 29 | 1-(1'-(2-(5-fluoropyridin-3-yl)ethyl)-3,4-dihydro-2H-spiro[isoquinoline-1,4'-piperidine]-2-yl)ethanone |
| 30 | 1-(1'-(2-(cyclopropylmethoxy)ethyl)-3,4-dihydro-2H-spiro[isoquinoline-1,4'-piperidine]-2-yl)ethanone |
| 31 | 1-(1'-(2-isobutoxyethyl)-3,4-dihydro-2H-spiro[isoquinoline-1,4'-piperidine]-2-yl)ethanone |
| 32 | 1-(1'-(2-(benzyloxy)ethyl)-3,4-dihydro-2H-spiro[isoquinoline-1,4'-piperidine]-2-yl)ethanone |
| 33 | 1-(1'-(cyclopropylmethyl)-3,4-dihydro-2H-spiro[isoquinoline-1,4'-piperidine]-2-yl)ethanone |
| 34 | 2-(2-acetyl-3,4-dihydro-2H-spiro[isoquinoline-1,4'-piperidine]-1'-yl)-1-morpholinoethanone |
| 35 | 3-(2-acetyl-3,4-dihydro-2H-spiro[isoquinoline-1,4'-piperidine]-1'-yl)-N-methyl-N-phenylpropanamide |
| 36 | 1-(1'-(3-(trifluoromethoxy)phenethyl)-3,4-dihydro-2H-spiro[isoquinoline-1,4'-piperidine]-2-yl)ethanone |
| 37 | tert-butyl 2-(2-acetyl-3,4-dihydro-2H-spiro[isoquinoline-1,4'-piperidine]-1'-yl)ethylcarbamate |
| 38 | N-(3-(2-(2-acetyl-3,4-dihydro-2H-spiro[isoquinoline-1,4'-piperidine]-1'-yl)ethyl)phenyl)acetamide |
| 39 | 2-(2-acetyl-3,4-dihydro-2H-spiro[isoquinoline-1,4'-piperidine]-1'-yl)-1-phenylethyl acetate |
| 40 | 1-(1'-(2-hydroxy-2-phenylethyl)-3,4-dihydro-2H-spiro[isoquinoline-1,4'-piperidine]-2-yl)ethanone |
| 41 | 1-(1'-(2-hydroxyethyl)-3,4-dihydro-2H-spiro[isoquinoline-1,4'-piperidine]-2-yl)ethanone |

| EX | Chemical name |
|---|---|
| 42 | 1-(1'-(2-(pyridin-2-yloxy)ethyl)-3,4-dihydro-2H-spiro[isoquinoline-1,4'-piperidine]-2-yl)ethanone |
| 43 | 1-(1'-(2-(pyridin-3-yloxy)ethyl)-3,4-dihydro-2H-spiro[isoquinoline-1,4'-piperidine]-2-yl)ethanone |
| 44 | 1-(1'-(2-(pyridin-4-yloxy)ethyl)-3,4-dihydro-2H-spiro[isoquinoline-1,4'-piperidine]-2-yl)ethanone |
| 45 | N-(4-(2-(2-acetyl-3,4-dihydro-2H-spiro[isoquinoline-1,4'-piperidine]-1'-yl)ethyl)pyridin-2-yl)acetamide |
| 46 | tert-butyl 2-(2-acetyl-3,4-dihydro-2H-spiro[isoquinoline-1,4'-piperidine]-1'-yl)ethyl(methyl)carbamate |
| 47 | 1-(1'-(2-(methylamino)ethyl)-3,4-dihydro-2H-spiro[isoquinoline-1,4'-piperidine]-2-yl)ethanone |
| 48 | N-(2-(2-acetyl-3,4-dihydro-2H-spiro[isoquinoline-1,4'-piperidine]-1'-yl)ethyl)-N-methylbenzamide |
| 49 | 2-acetyl-1'-phenethyl-3,4-dihydro-2H-spiro[isoquinoline-1,4'-piperidine]-6-yl acetate. |
| 50 | 1-(6-hydroxy-1'-phenethyl-3,4-dihydro-2H-spiro[isoquinoline-1,4'-piperidine]-2-yl)ethanone |
| 51 | 1-(6-chloro-1'-phenethyl-3,4-dihydro-2H-spiro[isoquinoline-1,4'-piperidine]-2-yl)ethanone |
| 52 | 2-hydroxy-1-(1'-phenethyl-3,4-dihydro-2H-spiro[isoquinoline-1,4'-piperidine]-2-yl)ethanone |
| 53 | 2-(methylsulfonyl)-1'-phenethyl-3,4-dihydro-2H-spiro[isoquinoline-1,4'-piperidine] |
| 54 | 2-methyl-1'-phenethyl-3,4-dihydro-2H-spiro[isoquinoline-1,4'-piperidine] |
| 55 | 6-methoxy-2-methyl-1'-phenethyl-3,4-dihydro-2H-spiro[isoquinoline-1,4'-piperidine] |
| 56 | N,N-diethyl-2-(2-methyl-3,4-dihydro-2H-spiro[isoquinoline-1,4'-piperidine]-1'-yl)acetamide |
| 57 | 2-(2-methyl-3,4-dihydro-2H-spiro[isoquinoline-1,4'-piperidine]-1'-yl)-1-(1,4-oxazepan-4-yl)ethanone |
| 58 | 1-(4-fluoropiperidin-1-yl)-2-(2-methyl-3,4-dihydro-2H-spiro[isoquinoline-1,4'-piperidine]-1'-yl)ethanone |
| 59 | 1-(4-(2-hydroxypropan-2-yl)piperidin-1-yl)-2-(2-methyl-3,4-dihydro-2H-spiro[isoquinoline-1,4'-piperidine]-1'-yl)ethanone |
| 60 | 1-(4-methoxypiperidin-1-yl)-2-(2-methyl-3,4-dihydro-2H-spiro[isoquinoline-1,4'-piperidine]-1'-yl)ethanone |
| 61 | 1-(4,4-difluoropiperidin-1-yl)-2-(2-methyl-3,4-dihydro-2H-spiro[isoquinoline-1,4'-piperidine]-1'-yl)ethanone |
| 62 | 2-(2-methyl-3,4-dihydro-2H-spiro[isoquinoline-1,4'-piperidine]-1'-yl)-1-(6-azaspiro[2.5]octan-6-yl)ethanone |
| 63 | 2-ethyl-1'-phenethyl-3,4-dihydro-2H-spiro[isoquinoline-1,4'-piperidine] |
| 64 | 2-((1'-phenethyl-3,4-dihydro-2H-spiro[isoquinoline-1,4'-piperidine]-2-yl)methyl)thiazole |
| 65 | 4-(2-(2-methyl-3,4-dihydro-2H-spiro[isoquinoline-1,4'-piperidine]-1'-yl)ethyl)morpholine |
| 66 | 1'-(cyclohexylmethyl)-2-methyl-3,4-dihydro-2H-spiro[isoquinoline-1,4'-piperidine] |
| 67 | 2-methyl-1'-((tetrahydro-2H-pyran-4-yl)methyl)-3,4-dihydro-2H-spiro[isoquinoline-1,4'-piperidine] |
| 68 | N,N-dimethyl-3-(2-methyl-3,4-dihydro-2H-spiro[isoquinoline-1,4'-piperidine]-1'-yl)propanamide |
| 69 | 2-(2-methyl-3,4-dihydro-2H-spiro[isoquinoline-1,4'-piperidine]-1'-yl)-1-phenylethanone |
| 70 | 2-(2-methyl-3,4-dihydro-2H-spiro[isoquinoline-1,4'-piperidine]-1'-yl)-1-morpholinoethanone |
| 71 | 2-(2-methyl-3,4-dihydro-2H-spiro[isoquinoline-1,4'-piperidine]-1'-yl)-1-(piperidin-1-yl)ethanone |
| 72 | N-methyl-2-(2-methyl-3,4-dihydro-2H-spiro[isoquinoline-1,4'-piperidine]-1'-yl)-N-phenylacetamide |
| 73 | N,N-dimethyl-2-(2-methyl-3,4-dihydro-2H-spiro[isoquinoline-1,4'-piperidine]-1'-yl)acetamide |
| 74 | 2-methyl-1'-(2-(tetrahydro-2H-pyran-4-yl)ethyl)-3,4-dihydro-2H-spiro[isoquinoline-1,4'-piperidine] |
| 75 | 2-methyl-1'-(2-(pyridin-2-yl)ethyl)-3,4-dihydro-2H-spiro[isoquinoline-1,4'-piperidine] |
| 76 | 2-methyl-1'-(2-(pyridin-3-yl)ethyl)-3,4-dihydro-2H-spiro[isoquinoline-1,4'-piperidine] |
| 77 | 1'-(2-methoxyethyl)-2-methyl-3,4-dihydro-2H-spiro[isoquinoline-1,4'-piperidine] |
| 78 | 1'-(2-isopropoxyethyl)-2-methyl-3,4-dihydro-2H-spiro[isoquinoline-1,4'-piperidine] |
| 79 | 2-methyl-1'-(2-(piperidin-1-yl)ethyl)-3,4-dihydro-2H-spiro[isoquinoline-1,4'-piperidine] |
| 80 | 4-(2-(2-methyl-3,4-dihydro-2H-spiro[isoquinoline-1,4'-piperidine]-1'-yl)ethyl)morpholin-3-one |
| 81 | N-methyl-3-(2-methyl-3,4-dihydro-2H-spiro[isoquinoline-1,4'-piperidine]-1'-yl)-N-phenylpropanamide |

-continued

| EX | Chemical name |
|---|---|
| 82 | 2-methyl-1'-(pyridin-2-ylmethyl)-3,4-dihydro-2H-spiro[isoquinoline-1,4'-piperidine] |
| 83 | 2-methyl-1'-(pyridin-4-ylmethyl)-3,4-dihydro-2H-spiro[isoquinoline-1,4'-piperidine] |
| 84 | 2-methyl-1'-(pyridin-3-ylmethyl)-3,4-dihydro-2H-spiro[isoquinoline-1,4'-piperidine] |
| 85 | 2-methyl-1'-(3-nitrophenethyl)-3,4-dihydro-2H-spiro[isoquinoline-1,4'-piperidine] |
| 86 | 1-(4-fluoropiperidin-1-yl)-2-(2-methyl-3,4-dihydro-2H-spiro[isoquinoline-1,4'-piperidine]-1'-yl)propan-1-one |
| 87 | N-isobutyl-N-methyl-2-(2-methyl-3,4-dihydro-2H-spiro[isoquinoline-1,4'-piperidine]-1'-yl)acetamide |
| 88 | 1-(3,3-difluoropiperidin-1-yl)-2-(2-methyl-3,4-dihydro-2H-spiro[isoquinoline-1,4'-piperidine]-1'-yl)ethanone |
| 89 | N-ethyl-N-isopropyl-2-(2-methyl-3,4-dihydro-2H-spiro[isoquinoline-1,4'-piperidine]-1'-yl)acetamide, |
| 90 | 2-(2-methyl-3,4-dihydro-2H-spiro[isoquinoline-1,4'-piperidine]-1'-yl)-1-(pyrrolidin-1-yl)ethanone |
| 91 | 2-(2-methyl-3,4-dihydro-2H-spiro[isoquinoline-1,4'-piperidine]-1'-yl)-1-(4-(trifluoromethyl)piperidin-1-yl)ethanone |
| 92 | 1-(3,3-difluoropyrrolidin-1-yl)-2-(2-methyl-3,4-dihydro-2H-spiro[isoquinoline-1,4'-piperidine]-1'-yl)ethanone |
| 93 | N-benzyl-N-methyl-2-(2-methyl-3,4-dihydro-2H-spiro[isoquinoline-1,4'-piperidine]-1'-yl)acetamide |
| 94 | (S)-1-(3-fluoropyrrolidin-1-yl)-2-(2-methyl-3,4-dihydro-2H-spiro[isoquinoline-1,4'-piperidine]-1'-yl)ethanone |
| 95 | (R)-1-(3-fluoropyrrolidin-1-yl)-2-(2-methyl-3,4-dihydro-2H-spiro[isoquinoline-1,4'-piperidine]-1'-yl)ethanone |
| 96 | 2-(2-methyl-3,4-dihydro-2H-spiro[isoquinoline-1,4'-piperidine]-1'-yl)-1-(pyridin-3-yl)etanol |
| 97 | 2-(2-methyl-3,4-dihydro-2H-spiro[isoquinoline-1,4'-piperidine]-1'-yl)-1-(pyridin-2-yl)ethanol |
| 98 | 2-(2-methyl-3,4-dihydro-2H-spiro[isoquinoline-1,4'-piperidine]-1'-yl)-1-(pyridin-4-yl)ethanol |
| 99 | (R)-2-(2-methyl-3,4-dihydro-2H-spiro[isoquinoline-1,4'-piperidine]-1'-yl)-1-(pyridin-4-yl)ethanol |
| 100 | (S)-2-(2-methyl-3,4-dihydro-2H-spiro[isoquinoline-1,4'-piperidine]-1'-yl)-1-(pyridin-4-yl)ethanol |
| 101 | N-(cyclopropylmethyl)-N-ethyl-2-(2-methyl-3,4-dihydro-2H-spiro[isoquinoline-1,4'-piperidine]-1'-yl)acetamide |
| 102 | N,N-diisopropyl-2-(2-methyl-3,4-dihydro-2H-spiro[isoquinoline-1,4'-piperidine]-1'-yl)acetamide |
| 103 | N-isopropyl-N-methyl-2-(2-methyl-3,4-dihydro-2H-spiro[isoquinoline-1,4'-piperidine]-1'-yl)acetamide |
| 104 | N-ethyl-N-isobutyl-2-(2-methyl-3,4-dihydro-2H-spiro[isoquinoline-1,4'-piperidine]-1'-yl)acetamide |
| 105 | N-ethyl-2-(2-methyl-3,4-dihydro-2H-spiro[isoquinoline-1,4'-piperidine]-1'-yl)-N-propylacetamide |
| 106 | N-cyclopropyl-N-ethyl-2-(2-methyl-3,4-dihydro-2H-spiro[isoquinoline-1,4'-piperidine]-1'-yl)acetamide |
| 107 | N-isopropyl-2-(2-methyl-3,4-dihydro-2H-spiro[isoquinoline-1,4'-piperidine]-1'-yl)-N-propylacetamide |
| 108 | N-isopropyl-N-(2-methoxyethyl)-2-(2-methyl-3,4-dihydro-2H-spiro[isoquinoline-1,4'-piperidine]-1'-yl)acetamide |
| 109 | N-ethyl-2-(2-methyl-3,4-dihydro-2H-spiro[isoquinoline-1,4'-piperidine]-1'-yl)-N-(pentan-3-yl)acetamide |
| 110 | N-isobutyl-N-isopropyl-2-(2-methyl-3,4-dihydro-2H-spiro[isoquinoline-1,4'-piperidine]-1'-yl)acetamide |
| 111 | N-methyl-2-(2-methyl-3,4-dihydro-2H-spiro[isoquinoline-1,4'-piperidine]-1'-yl)-N-(pentan-3-yl)acetamide |
| 112 | N-(cyclopropylmethyl)-N-methyl-2-(2-methyl-3,4-dihydro-2H-spiro[isoquinoline-1,4'-piperidine]-1'-yl)acetamide |
| 113 | 1-(3-fluoropyridin-4-yl)-2-(2-methyl-3,4-dihydro-2H-spiro[isoquinoline-1,4'-piperidine]-1'-yl)ethanol |
| 114 | 2-(2-methyl-3,4-dihydro-2H-spiro[isoquinoline-1,4'-piperidine]-1'-yl)-1-(4-methylpiperidin-1-yl)ethanone |
| 115 | 1-((2S,6R)-2,6-dimethylmorpholino)-2-(2-methyl-3,4-dihydro-2H-spiro[isoquinoline-1,4'-piperidine]-1'-yl)ethanone |
| 116 | N-methyl-2-(2-methyl-3,4-dihydro-2H-spiro[isoquinoline-1,4'-piperidine]-1'-yl)-N-(pyridin-2-ylmethyl)acetamide |
| 117 | 3-(2-(2-methyl-3,4-dihydro-2H-spiro[isoquinoline-1,4'-piperidine]-1'-yl)ethyl)aniline |
| 118 | N-(3-(2-(2-methyl-3,4-dihydro-2H-spiro[isoquinoline-1,4'-piperidine]-1'-yl)ethyl)phenyl)methanesulfonamide |
| 119 | N-(3-(2-(2-methyl-3,4-dihydro-2H-spiro[isoquinoline-1,4'-piperidine]-1'-yl)ethyl)phenyl)acetamide |
| 120 | 2-(2-methyl-3,4-dihydro-2H-spiro[isoquinoline-1,4'-piperidine]-1'-yl)-1-phenylethanol |

| EX | Chemical name |
|---|---|
| 121 | 2-methyl-1'-(2-(pyridin-4-yl)ethyl)-3,4-dihydro-2H-spiro[isoquinoline-1,4'-piperidine] |
| 122 | 2-(2-methoxyethyl)-1'-phenethyl-3,4-dihydro-2H-spiro[isoquinoline-1,4'-piperidine] |
| 123 | 2-(1'-phenethyl-3,4-dihydro-2H-spiro[isoquinoline-1,4'-piperidine]-2-yl)ethanol |
| 124 | 2-(2-methoxyethyl)-1'-(2-(pyridin-3-yl)ethyl)-3,4-dihydro-2H-spiro[isoquinoline-1,4'-piperidine] |
| 125 | 2-(1'-(2-(pyridin-3-yl)ethyl)-3,4-dihydro-2H-spiro[isoquinoline-1,4'-piperidine]-2-yl)etanol |
| 126 | 2-(2-(2-hydroxyethyl)-3,4-dihydro-2H-spiro[isoquinoline-1,4'-piperidine]-1'-yl)-1-(piperidin-1-yl)ethanone |
| 127 | 2-(1'-(2-(5-fluoropyridin-3-yl)ethyl)-3,4-dihydro-2H-spiro[isoquinoline-1,4'-piperidine]-2-yl)etanol |
| 128 | 2-(1'-(2-(5-(trifluoromethyl)pyridin-3-yl)ethyl)-3,4-dihydro-2H-spiro[isoquinoline-1,4'-piperidine]-2-yl)ethanol |
| 129 | 2-(1'-(2-(pyridin-4-yl)ethyl)-3,4-dihydro-2H-spiro[isoquinoline-1,4'-piperidine]-2-yl)ethanol |
| 130 | 2-(1'-(2-(3-fluoropyridin-4-yl)ethyl)-3,4-dihydro-2H-spiro[isoquinoline-1,4'-piperidine]-2-yl)ethanol |
| 131 | 2-methyl-1'-phenethyl-3,4-dihydro-2H-spiro[isoquinoline-1,4'-piperidin]-6-ol |
| 132 | 2,2,2-trifluoro-1-(1'-phenethyl-3,4-dihydro-2H-spiro[isoquinoline-1,4'-piperidine]-2-yl)ethanone |
| 133 | 1'-phenethyl-2-(2,2,2-trifluoroethyl)-3,4-dihydro-2H-spiro[isoquinoline-1,4'-piperidine] |
| 134 | 1-morpholino-2-(2-(2,2,2-trifluoroethyl)-3,4-dihydro-2H-spiro[isoquinoline-1,4'-piperidine]-1'-yl)ethanone |
| 135 | 1-(piperidin-1-yl)-2-(2-(2,2,2-trifluoroethyl)-3,4-dihydro-2H-spiro[isoquinoline-1,4'-piperidine]-1'-yl)ethanone |
| 136 | 1'-(2-(pyridin-4-yl)ethyl)-2-(2,2,2-trifluoroethyl)-3,4-dihydro-2H-spiro[isoquinoline-1,4'-piperidine] |
| 137 | 1'-(2-(pyridin-3-yl)ethyl)-2-(2,2,2-trifluoroethyl)-3,4-dihydro-2H-spiro[isoquinoline-1,4'-piperidine] |
| 138 | 1-(piperidin-1-yl)-2-(2,4,4-trimethyl-3,4-dihydro-2H-spiro[isoquinoline-1,4'-piperidine]-1'-yl)ethanone |
| 139 | 1-(1'-phenethylspiro[isoindoline-1,4'-piperidine]-2-yl)ethanone |
| 140 | 2-methyl-1'-phenethylspiro[isoindoline-1,4'-piperidine] |
| 141 | 2-methyl-1'-((tetrahydro-2H-pyran-4-yl)methyl)spiro[isoindoline-1,4'-piperidine] | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a very preferred further embodiment the compounds of the general formula I are also selected from (and may also be added to the above list from which compounds of the general formula I are selected)

| | |
|---|---|
| 142 | (R)-1-(3-fluoropyridin-4-yl)-2-(2-methyl-3,4-dihydro-2H-spiro[isoquinoline-1,4'-piperidine]-1'-yl)ethanol |
| 143 | (S)-1-(3-fluoropyridin-4-yl)-2-(2-methyl-3,4-dihydro-2H-spiro[isoquinoline-1,4'-piperidine]-1'-yl)ethanol |
| 144 | N-ethyl-2-(2-ethyl-3,4-dihydro-2H-spiro[isoquinoline-1,4'-piperidine]-1'-yl)-N-isopropylacetamide |
| 145 | 1-(4,4-difluoropiperidin-1-yl)-2-(2-ethyl-3,4-dihydro-2H-spiro[isoquinoline-1,4'-piperidine]-1'-yl)ethanone |
| 146 | 2-(2-ethyl-3,4-dihydro-2H-spiro[isoquinoline-1,4'-piperidine]-1'-yl)-1-(pyridin-4-yl)ethanol |
| 147 | 2-(2-ethyl-3,4-dihydro-2H-spiro[isoquinoline-1,4'-piperidine]-1'-yl)-1-morpholinoethanone |
| 148 | 4-(2-(2-ethyl-3,4-dihydro-2H-spiro[isoquinoline-1,4'-piperidine]-1'-yl)ethyl)morpholine |
| 149 | 2-(2-ethyl-3,4-dihydro-2H-spiro[isoquinoline-1,4'-piperidine]-1'-yl)-1-(1,1-dioxo-thiomorpholin-4-yl)ethanone |
| 150 | 2-(2-ethyl-3,4-dihydro-2H-spiro[isoquinoline-1,4'-piperidine]-1'-yl)-1-(4-fluoropiperidin-1-yl)ethanone |
| 151 | 1-(3,3-difluoropiperidin-1-yl)-2-(2-ethyl-3,4-dihydro-2H-spiro[isoquinoline-1,4'-piperidine]-1'-yl)ethanone |
| 152 | 2-(2-ethyl-3,4-dihydro-2H-spiro[isoquinoline-1,4'-piperidine]-1'-yl)-N-methyl-N-(pentan-3-yl)acetamide |
| 153 | 2-(2-ethyl-3,4-dihydro-2H-spiro[isoquinoline-1,4'-piperidine]-1'-yl)-N,N-dimethylacetamide |

| | |
|---|---|
| 154 | N-cyclopropyl-N-ethyl-2-(2-ethyl-3,4-dihydro-2H-spiro[isoquinoline-1,4'-piperidine]-1'-yl)acetamide |
| 155 | N,N-diethyl-2-(2-ethyl-3,4-dihydro-2H-spiro[isoquinoline-1,4'-piperidine]-1'-yl)acetamide |
| 156 | 1-(4,4-difluoropiperidin-1-yl)-2-(2-methylspiro[isoindoline-1,4'-piperidine]-1'-yl)ethanone |
| 157 | N-ethyl-N-isopropyl-2-(2-methylspiro[isoindoline-1,4'-piperidine]-1'-yl)acetamide |
| 158 | N-ethyl-1'-(2-(pyridin-4-yl)ethyl)-3,4-dihydro-2H-spiro[isoquinoline-1,4'-piperidine]-2-carboxamide |
| 159 | 1'-(2-(Pyrimidin-5-yl)ethyl)-2-(2,2,2-trifluoroethyl)-3,4-dihydro-2H-spiro[isoquinoline-1,4'-piperidine] |
| 160 | 2-(2-(2-Methyl-3,4-dihydro-2H-spiro[isoquinoline-1,4'-piperidine]-1'-yl)ethylamino)ethanol | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein
X is, —$CR_xR_{x'}$—, —$CR_xR_xNR_7$—, or $CR_xR_xO$—, and
$R_1$ is —$C(O)R_6$ or —$S(O)_2R_6$,
the compound being exemplified in examples 1-53, 132 and 139;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein
X is, —$CR_xR_{x'}$—, —$CR_xOR_{14'}$—, —$CR_xR_xNR_7$—, or $CR_xR_xO$—, and
$R_1$ is substituted or unsubstituted $C_{1-6}$ alkyl, substituted or unsubstituted $C_{2-6}$ alkenyl, substituted or unsubstituted $C_{2-6}$ alkynyl;
the compound being exemplified in examples 54, 55, 63, 65-67, 74-80, 82-85, 96-100, 113, 117-125, 127-131, 133, 136, 137, 140 and 141;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein
X is, —$CR_xR_{x'}$—, —$CR_xOR_{14'}$—, —$CR_xR_xNR_7$—, or $CR_xR_xO$—, and
$R_1$ is substituted or unsubstituted alkylaryl, substituted or unsubstituted alkylheterocyclyl, or unsubstituted alkylcycloalkyl,
the compound being exemplified in example 64;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein
X is —$C(O)NR_7$—, and
$R_1$ is substituted or unsubstituted $C_{1-6}$ alkyl, substituted or unsubstituted $C_{2-6}$ alkenyl, substituted or unsubstituted $C_{2-6}$ alkynyl,
the compound being exemplified in examples 56, 68, 72, 73, 81, 87, 89, 93, 101-112 and 116;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein
X is —C(O)—,
$R_1$ is substituted or unsubstituted $C_{1-6}$ alkyl, substituted or unsubstituted $C_{2-6}$ alkenyl, substituted or unsubstituted $C_{2-6}$ alkynyl, and
$R_2$ is substituted or unsubstituted heterocyclyl, wherein the heterocyclyl contains, at least, one nitrogen attached to the carbonyle group in X;
the compound being exemplified in examples 57-62, 70, 71, 86, 88, 90-92, 94, 95, 114, 115, 126, 134, 135, 138;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I,
$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, —$C(O)R_6$, —$C(O)CH_2OR_6$, —$C(O)CH_2OC(O)R_6$, —$C(O)OR_6$, —$C(O)NR_6R_{6'}$ or —$S(O)_2R_6$;
wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl and substituted or unsubstituted alkyheterocylcyl;
wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, $NR_{11}S(O)_2NR_{11'}R_{11''}$ and $C(CH_3)_2OR_{11}$;
additionally, cycloalkyl or non-aromatic heterocyclyl in $R_1$ or $R_6$, also in alkylcycloalkyl and alkylheterocyclyl, if substituted, may also be substituted with

or =O;
wherein the alkyl, alkylene or alkynyl in $R_1$ or $R_6$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general formula I,
$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
wherein said cycloalkyl, aryl or heterocyclyl in $R_2$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
additionally, cycloalkyl or non-aromatic heterocyclyl in $R_2$, also in alkylcycloalkyl and alkylheterocyclyl, if substituted, may also be substituted with

or =O;
wherein the alkyl, alkylene or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general formula I,
the alkyl, alkylene or alkynyl, other than those defined in $R_1$, $R_2$ or $R_6$, if substituted, is substituted with one or more substituent/s selected from —$OR_{10}$, halogen, —CN, haloalkyl, haloalkoxy, —$SR_{10}$, —$S(O)R_{10}$, and —$S(O)_2R_{10}$;
wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention of general formula I,
the aryl, heterocyclyl or cycloalkyl, also in alkylaryl, alkylcycloalkyl and alkylheterocyclyl, other than those defined in $R_1$, $R_2$ or $R_6$, if substituted, is substituted with one or more substituent/s selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8R_{8'}$, —$NR_8C(O)NR_{8'}R_{8''}$, —$SR_8$, —$S(O)R_8$, $S(O)_2R_8$, —CN, haloalkyl, haloalkoxy, —$C(O)OR_8$, —$C(O)NR_8R_{8'}$, —$OCH_2CH_2OH$, —$NR_8S(O)_2NR_{8'}R_{8''}$, and $C(CH_3)_2OR_8$;
additionally, wherein cycloalkyl or non-aromatic heterocyclyl, other than those defined in $R_1$, $R_2$ or $R_6$, also in alkylcycloalkyl and alkylheterocyclyl, if substituted, may also be substituted with

or =O;
wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;
and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ or $R_6$ of any of the previous embodiments, the cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ or $R_6$ of any of the previous embodiments, the cycloalkyl or non-aromatic heterocyclyl in $R_1$ or $R_6$, also in alkylcycloalkyl and alkylheterocyclyl, if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ or $R_6$ of any of the previous embodiments, the alkyl, alkylene or alkynyl in $R_1$ or $R_6$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments, the cycloalkyl, aryl or heterocyclyl in $R_2$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments, the cycloalkyl or non-aromatic heterocyclyl in $R_2$, also in alkylcycloalkyl and alkylheterocyclyl, if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments, the alkyl, alkylene or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to alkyls other than those defined in $R_1$, $R_2$ or $R_6$ of any of the previous embodiments, the alkyl, alkylene or alkynyl, other than those defined in $R_1$, $R_2$ or $R_6$, if substituted, is substituted with one or more substituent/s selected from —$OR_{10}$, halogen, —CN, haloalkyl, haloalkoxy, —$SR_{10}$, —$S(O)R_{10}$, and —$S(O)_2R_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to aryl, heterocycly and cycloalkyl other than those defined in $R_1$, $R_2$ or $R_6$ of any of the previous embodiments, the aryl, heterocyclyl or cycloalkyl, also in alkylaryl, alkylcycloalkyl and alkylheterocyclyl, other than those defined in $R_1$, $R_2$ or $R_6$, if substituted, is substituted with one or more substituent/s selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8R_{8'}$, —$NR_8C(O)NR_8R_{8'''}$, —$SR_8$, —$S(O)R_8$, $S(O)_2R_8$, —CN, haloalkyl, haloalkoxy, —$C(O)OR_8$, —$C(O)NR_8R_{8'}$, —$OCH_2CH_2OH$, —$NR_8S(O)_2NR_{8'}R_{8''}$ and $C(CH_3)_2OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to heterocycly and cycloalkyl other than those defined in $R_1$, $R_2$ or $R_6$ of any of the previous embodiments, the cycloalkyl or non-aromatic heterocyclyl, other than those defined in $R_1$, $R_2$ or $R_6$, also in alkylcycloalkyl and alkylheterocyclyl, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the invention of general formula I, the halogen is fluorine, chlorine, iodine or bromine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the invention of general formula I,
the halogen is fluorine or chlorine
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the invention of general formula I, the haloalkyl is —CF3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention of general formula I,
the haloalkoxy is —OCF3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as $K_i$ which is preferably <1000 nM for both receptors, more preferably <500 nM, even more preferably <100 nM.

A further embodiment of the invention concerns compounds of general Formula (XV) and general formula (Va). This embodiment is herewith called EMBODIMENT A.

A first embodiment of EMBODIMENT A is a compound of general formula (XV) or (Va):

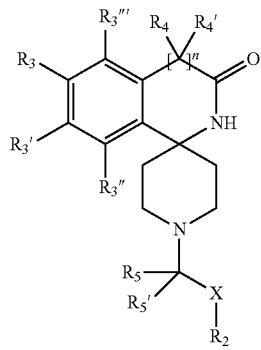

(XV)

or

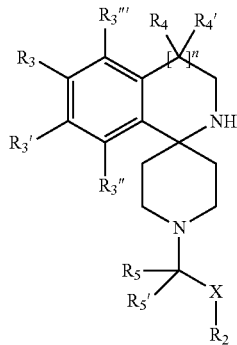

(Va)

wherein
n is 0 or 1
$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
wherein said cycloalkyl, aryl or heterocyclyl in $R_2$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
additionally, cycloalkyl or non-aromatic heterocyclyl in $R_2$, also in alkylcycloalkyl and alkylheterocyclyl, if substituted, may also be substituted with

or =O;
wherein the alkyl, alkylene or alkynyl in $R_2$, if substituted, is substituted with one or more substituent/s selected from —$OR_{12}$, halogen, —CN, haloalkyl, haloalkoxy, —$NR_{12}R_{12'}$, —$SR_{12}$, —$S(O)R_{12}$, and —$S(O)_2R_{12}$;

wherein $R_{12}$, $R_{12'}$ and $R_{12''}$ are independently selected from hydrogen, halogen, unsubstituted acetyl, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

X is selected from a bond, $-CR_xR_{x'}$ $-CR_xOR_{14'}$, $-CR_xR_{x'}NR_7-$, $-O-$, $-CR_xR_{x'}O-$, $-CR_xR_{x'}NR_7C(O)-$, $-C(O)-$, $-CR_xR_{x'}C(O)-$, $-C(O)O-$, $-C(O)NR_7-$, $-CR_xR_{x'}C(O)NR_7-$ and $-C(O)NR_7CR_xR_{x'}-$;

wherein $R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc;

$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, $-C(O)OR_{14}$, $-C(O)NR_{14}R_{14'}$, $-NR_{14}C(O)R_{14'}$, and $-NR_{14}R_{14'''}$, $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is selected from hydrogen, halogen, $-R_9$, $-OR_9$, $-NO_2$, $-NR_9R_{9'''}$, $-NR_9C(O)R_{9'}$, $-NC(O)OR_9$, $-NR_9S(O)_2R_{9'}$, $-S(O)_2NR_9R_{9'}$, $-NR_9C(O)NR_9R_{9''}$, $-SR_9$, $-S(O)R_9$, $-S(O)_2R_9$, $-CN$, haloalkyl, haloalkoxy, $-C(O)OR_9$, $-C(O)NR_9R_{9'}$, $-OCH_2CH_2OH$, $-NR_9S(O)_2NR_9R_{9''}$, $-OCOR_9$, and $C(CH_3)_2OR_9$;

$R_{3'}$, $R_{3''}$ and $R_{3'''}$ are independently selected from hydrogen, halogen, $-R_9$, $-OR_9$, $-NO_2$, $-NR_9R_{9'''}$, $-NR_9C(O)R_{9'}$, $-NC(O)OR_9$, $-NR_9S(O)_2R_{9'}$, $-S(O)_2NR_9R_{9'}$, $-NR_9C(O)NR_9R_{9''}$, $-SR_9$, $-S(O)R_9$, $-S(O)_2R_9$, $-CN$, haloalkyl, haloalkoxy, $-C(O)OR_9$, $-C(O)NR_9R_{9'}$, $-OCH_2CH_2OH$, $-NR_9S(O)_2NR_9R_{9''}$, $-OCOR_9$, and $C(CH_3)_2OR_9$;

wherein $R_9$, $R_{9'}$, and $R_{9''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ is selected from hydrogen, $-OR_{13}$, substituted or unsubstituted $C_{1-6}$ alkyl, substituted or unsubstituted $C_{2-6}$ alkenyl, substituted or unsubstituted $C_{2-6}$ alkynyl, $-C(O)OR_{13}$, $-C(O)NR_{13}R_{13'}$, $-NR_{13}C(O)R_{13'}$, $-NR_{13}R_{13'''}$, $-NC(O)OR_{13}$, and substituted or unsubstituted heterocyclyl;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl; and wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein the alkyl, alkylene or alkynyl, other than those defined in $R_2$, if substituted, is substituted with one or more substituent/s selected from $-OR_{10}$, halogen, $-CN$, haloalkyl, haloalkoxy, $-NR_{10}R_{10'}$, $-SR_{10}$, $-S(O)R_{10}$, and $-S(O)_2R_{10}$;

wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

wherein the aryl, heterocyclyl or cycloalkyl, also in alkylaryl, alkylcycloalkyl and alkylheterocyclyl, other than those defined in $R_2$, if substituted, is substituted with one or more substituent/s selected from halogen, $-R_8$, $-OR_8$, $-NO_2$, $-NR_8R_{8'''}$, $NR_8C(O)R_{8'}$, $-NR_8S(O)_2R_{8'}$, $-S(O)_2NR_8R_{8'}$, $-NR_8C(O)NR_8R_{8''}$, $-SR_8$, $-S(O)R_8$, $S(O)_2R_8$, $-CN$, haloalkyl, haloalkoxy, $-C(O)OR_8$, $-C(O)NR_8R_{8'}$, $-OCH_2CH_2OH$, $-NR_8S(O)_2NR_8R_{8''}$, and $C(CH_3)_2OR_8$;

additionally, wherein cycloalkyl or non-aromatic heterocyclyl, other than those defined in $R_1$, $R_2$ or $R_6$, also in alkylcycloalkyl and alkylheterocyclyl, if substituted, may also be substituted with

or $=O$;

wherein $R_8$, $R_{8'}$, and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

The general definitions of alkyl, alkenyl, alkinyl, aryl, alkylaryl, cycloalkyl, alkylcycloalkyl, heterocyclyl and alkylheterocyclyl as well as the general definitions on their substitution pattern set out above apply also to EMBODIMENT A if not defined otherwise below.

In a second embodiment of EMBODIMENT A the compound according to the first embodiment of EMBODIMENT A is a compound according to any one of general formulas XV or Va

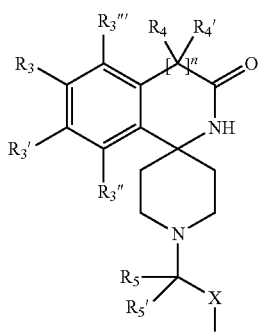

(XV)

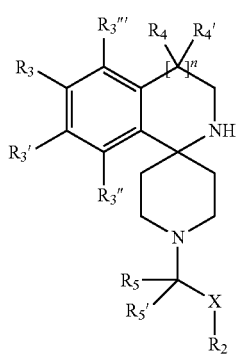

(Va)

wherein n is 1

R$_2$ is hydrogen, substituted or unsubstituted C$_{1-6}$ alkyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

wherein said cycloalkyl, aryl or heterocyclyl in R$_2$, also in alkylaryl, alkylcycloalkyl and alkylheterocyclyl, if substituted, is substituted with one or more substituent/s selected from halogen, —R$_{12}$, —OR$_{12}$, haloalkyl, and haloalkoxy; wherein the alkyl, alkylene or alkynyl in R$_2$, if substituted, is substituted with one or more substituent/s selected from —OR$_{12}$, and halogen;

X is selected from a bond, —CR$_x$R$_{x'}$—, —CR$_x$R$_x$NR$_7$—, —O—, —CR$_x$R$_x$O—, — and —C(O)—;

wherein R$_7$ is selected from hydrogen, substituted or unsubstituted C$_{1-4}$ alkyl;

R$_x$ is selected from hydrogen, substituted or unsubstituted C$_{1-4}$ alkyl;

R$_{x'}$ is selected from hydrogen, substituted or unsubstituted C$_{1-6}$ alkyl;

R$_3$ is hydrogen;

R$_{3'}$, R$_{3''}$ and R$_{3'''}$ are hydrogen;

R$_4$ is selected from hydrogen, substituted or unsubstituted C$_{1-4}$ alkyll;

R$_{4'}$ is selected from hydrogen, or substituted or unsubstituted C$_{1-4}$ alkyl;

R$_5$ and R$_{5'}$ are hydrogen;

wherein the alkyl, alkylene or alkynyl, other than those defined in R$_2$, if substituted, is substituted with one or more substituent/s selected from —OR$_{10}$, and halogen; wherein R$_{10}$, is selected from hydrogen, and unsubstituted C$_{1-6}$ alkyl;

wherein the aryl, heterocyclyl or cycloalkyl, also in alkylaryl, alkylcycloalkyl and alkylheterocyclyl, other than those defined in R$_2$, if substituted, is substituted with one or more substituent/s selected from halogen, —R$_8$, —OR$_8$, haloalkyl, and haloalkoxy;

wherein R$_8$ is selected from hydrogen, unsubstituted C$_{1-6}$ alkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a third embodiment of the EMBODIMENT A the compound according to first or second embodiment of EMBODIMENT A is a compound according to general formula XV

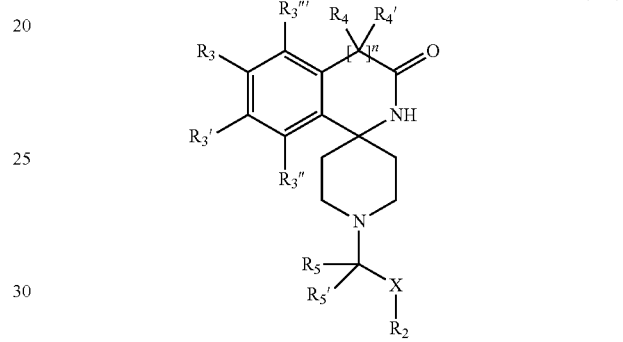

(XV)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a fourth embodiment of the EMBODIMENT A the compound according to first or second embodiment of EMBODIMENT A is a compound according to general formula Va

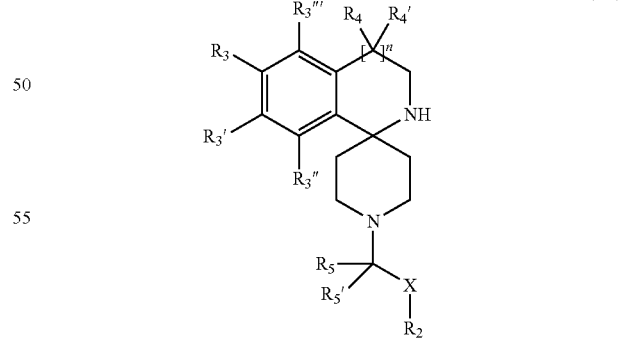

(Va)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the following the phrase "compound of the invention" is used. This is to be understood as any compound according to the invention as described above according to general formula I.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention. This also applies to the compounds of EMBODIMENT A.

In general the processes are described below in the experimental part. The starting materials are commercially available or can be prepared by conventional methods.

A preferred aspect of the invention is also a process for the production of a compound according to formula I. In this process there is also the disclosure for the process of production of the compounds of EMBODIMENT A which—most often—act as intermediates in the process for the production of a compound according to formula I.

In a particular embodiment there is a process for the production of a compound according to formula I,

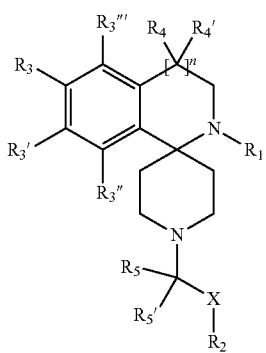
(I)

wherein n, X, $R_1$, $R_2$, $R_3$, $R_{3'}$, $R_{3''}$, $R_{3'''}$, $R_4$, $R_{4'}$, $R_5$ and $R_{5'}$ are as defined in the preceeding claims, said process comprises reacting a compound of formula IX with a suitable reagent of formula Xa-d, using different conditions depending on the reagent nature,

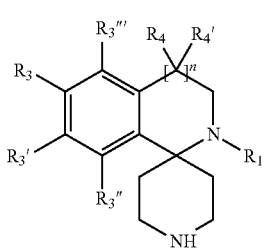
IX wherein,
n, $R_1$, $R_2$, $R_3$, $R_{3'}$, $R_{3''}$, $R_{3'''}$, $R_4$ and $R_{4'}$ are as defined above in the description,
Xa is $WCR_5R_{5'}XR_2$,
Xb is $O=CR_5R_{5'}XR_2$,
Xc is $CR_5R_{5'}=CR_xR_2$,
Xd is $CR_5R_{5'}OCR_xR_2$; and
W is a leaving group.

In another embodiment there is a process for the production of a compound according to formula I,

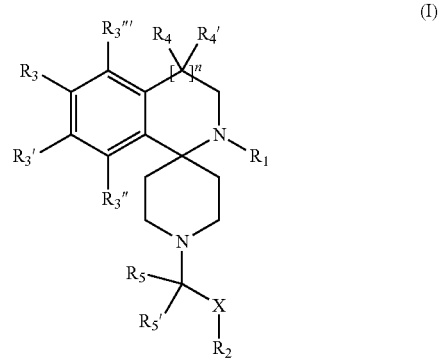
(I)

wherein n, X, $R_1$, $R_2$, $R_3$, $R_{3'}$, $R_{3''}$, $R_{3'''}$, $R_4$, $R_{4'}$, $R_5$ and $R_{5'}$ are as defined above in the description, said process comprises
reacting of a compound of formula XII with a reducing agent, in a suitable solvent, at a suitable temperature comprised between room temperature and the reflux temperature,

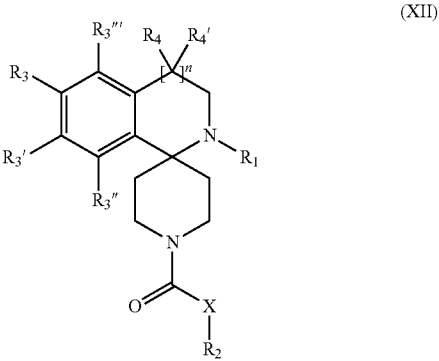
(XII)

wherein n, X, $R_1$, $R_2$, $R_3$, $R_{3'}$, $R_{3''}$, $R_{3'''}$, $R_4$ and $R_{4'}$ are as defined above in the description, In another embodiment there is a process for the production of a compound according to formula I,

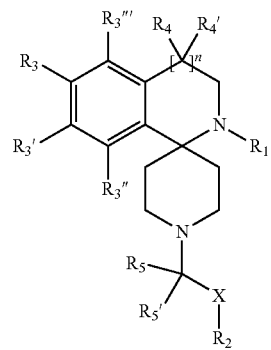
(I)

wherein n, X, $R_1$, $R_2$, $R_3$, $R_{3'}$, $R_{3''}$, $R_{3'''}$, $R_4$, $R_{4'}$, $R_5$ and $R_{5'}$ are as defined above in the description, said process comprises
reacting intermediate XIV with Xa-d, followed by reaction with VIIa-h,

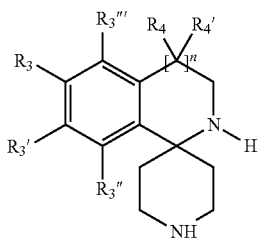

(XIV)

wherein, n, $R_1$, $R_2$, $R_3$, $R_{3'}$, $R_{3''}$, $R_{3'''}$, $R_4$ and $R_{4'}$ are as defined in the previous claims, Xa is $WCR_5R_{5'}XR_2$, Xb is $O=CR_5R_{5'}XR_2$, Xc is $CR_5R_5=CR_xR_2$, Xd is $CR_5R_{5'}OCR_xR_2$;

VIIa is $R_1=O$,

VIIb is $R_1W$,

VIIc is $R_6COW$,

VIId is $(R_6CO)_2$,

VIIe is $R_6SO_2W$,

VIIf is $R_6NCO$,

VIIg is $R_6NSO$,

VIIh is $R_6COOW$, and

W is a leaving group.

In another embodiment there is a process for the production of a compound according to formula I,

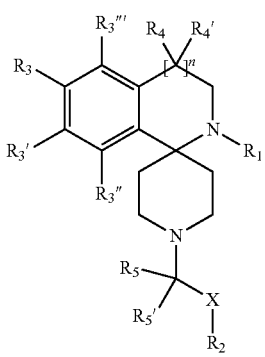

(I)

wherein n, X, $R_1$, $R_2$, $R_3$, $R_{3'}$, $R_{3''}$, $R_{3'''}$, $R_4$, $R_{4'}$, $R_5$ and $R_{5'}$ are as defined above in the description, said process comprises transforming intermediate XV by reduction with a reducing agent, in a suitable solvent, at a suitable temperature comprised between room temperature and the reflux temperature, followed by reaction with VIIa-h under the suitable conditions, or in the case where $R_1$ is alkyl, the step order can be inverted and compound I can be obtained by reaction of intermediate XV with VIIb under the suitable conditions, followed by reaction with a reducing agent, in a suitable solvent, at a suitable temperature comprised between room temperature and the reflux temperature, (XV)

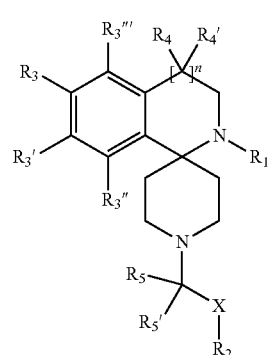

wherein, n, X, $R_1$, $R_2$, $R_3$, $R_{3'}$, $R_{3''}$, $R_{3'''}$, $R_4$, $R_{4'}$, $R_5$ and $R_{5'}$ are as defined above in the description, VIIa is $R_1=O$, VIIb is $R_1W$, VIIc is $R_6COW$, VIId is $(R_6CO)_2$, VIIe is $R_6SO_2W$, VIIf is $R_6NCO$, VIIg is $R_6NSO$, VIIh is $R_6COOW$, and W is a leaving group.

In another embodiment there is a process for the production of a compound according to formula I, (I)

wherein n, X, $R_1$, $R_2$, $R_3$, $R_{3'}$, $R_{3''}$, $R_{3'''}$, $R_4$, $R_{4'}$, $R_5$ and $R_{5'}$ are as defined above in the description, said process comprises in the case where $R_3$, $R_{3'}$, $R_{3''}$ or $R_{3'''}$ is an electron donating group, compound I can also be prepared by reaction of a compound of formula VI with a compound of formula XVI in a suitable solvent, at a suitable temperature, preferably comprised between 80 and 120° C., followed by reaction of with VIIa-h.

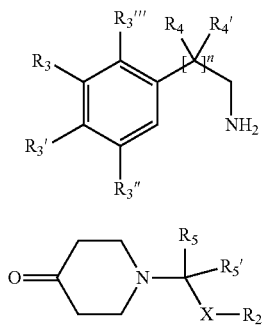

(VI)

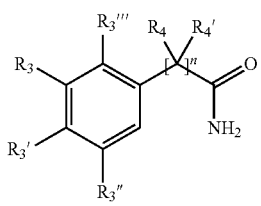

(XVI)

wherein, n, $R_1$, $R_2$, $R_3$, $R_{3'}$, $R_{3''}$, $R_{3'''}$, $R_4$, $R_{4'}$, $R_5$ and $R_{5'}$ are as defined above in the description, VIIa is $R_1$=O,
VIIb is $R_1W$,
VIIc is $R_6COW$,
VIId is $(R_6CO)_2$,
VIIe is $R_6SO_2W$,
VIIf is $R_6NCO$,
VIIg is $R_6NSO$,
VIIh is $R_6COOW$, and
W is a leaving group.

In a particular embodiment a compound of Formula (II),

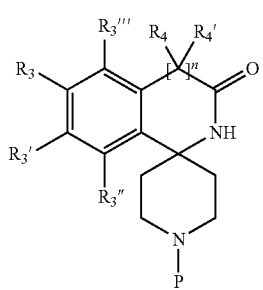

(II)

is used for the preparation of compounds of Formula (I), wherein n, $R_3$, $R_{3'}$, $R_{3''}$, $R_{3'''}$, $R_4$ and $R_{4'}$ are as defined above in the description.

In another particular embodiment a compound of Formula (IV),

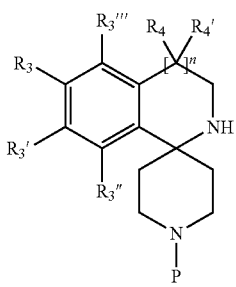

(IV)

is used for the preparation of compounds of Formula (I), wherein n $R_3$, $R_{3'}$, $R_{3''}$, $R_{3'''}$, $R_4$ and $R_{4'}$ are as defined above in the description and P is a protecting group.

In a particular embodiment a compound of Formula (V)

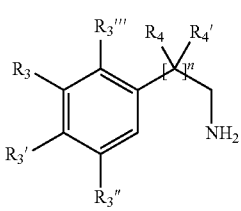

(V)

is used for the preparation of compounds of Formula (I), wherein n, $R_3$, $R_{3'}$, $R_{3''}$, $R_{3'''}$, $R_4$ and $R_{4'}$ are as defined above in the description and P is a protecting group.

In a particular embodiment a compound of Formula (VI)

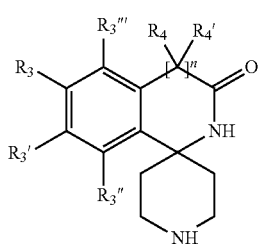

(VI)

is used for the preparation of compounds of Formula (I), wherein n, $R_3$, $R_{3'}$, $R_{3''}$, $R_{3'''}$, $R_4$ and $R_{4'}$ are as defined above in the description.

In a particular embodiment a compound of Formula (XIII)

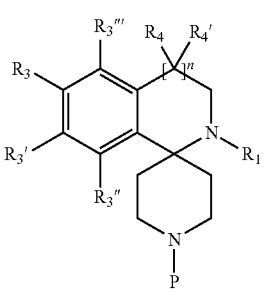

(XIII)

is used for the preparation of compounds of Formula (I), wherein n, $R_3$, $R_{3'}$, $R_{3''}$, $R_{3'''}$, $R_4$ and $R_{4'}$ are as defined above in the description.

In a particular embodiment a compound of Formula (VIII)

(VIII)

is used for the preparation of compounds of Formula (I), wherein n, $R_3$, $R_{3'}$, $R_{3''}$, $R_{3'''}$, $R_4$ and $R_{4'}$ are as defined above in the description and P is a protecting group.

In a particular embodiment a compound of Formula (XIV)

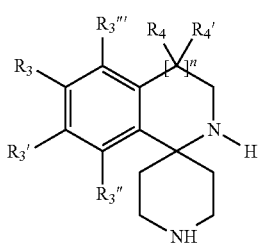

is used for the preparation of compounds of Formula (I), wherein n, $R_3$, $R_{3'}$, $R_{3''}$, $R_{3'''}$, $R_4$ and $R_{4'}$ are as defined above in the description.

In a particular embodiment a compound of Formula (XV)

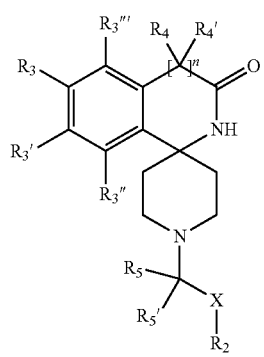

is used for the preparation of compounds of Formula (I), wherein n, $R_3$, $R_{3'}$, $R_{3''}$, $R_{3'''}$, $R_4$, $R_{4'}$, $R_5$ and $R_{5'}$ are as defined above in the description.

In a particular embodiment a compound of Formula (XII)

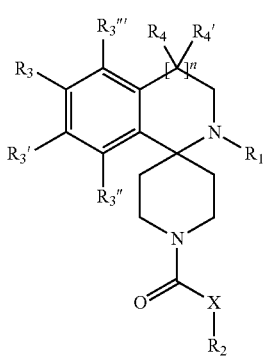

is used for the preparation of compounds of Formula (I), wherein n, $R_1$, $R_2$, $R_3$, $R_{3'}$, $R_{3''}$, $R_{3'''}$, $R_4$ and $R_{4'}$ are as defined above in the description.

In a particular embodiment a compound of Formula (IX)

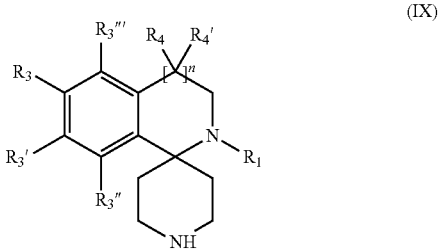

is used for the preparation of compounds of Formula (I), wherein n, $R_1$, $R_3$, $R_{3'}$, $R_{3''}$, $R_{3'''}$, $R_4$, and $R_{4'}$ are as defined above in the description.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient. All of this also applies to the compounds of EMBODIMENT A which could also be formulated into a pharmaceutical composition.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art.

The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia. All of this also applies to the compounds of EMBODIMENT A and thus applies for their use as a medicament for the treatment of pain.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A 5-step process is described for the preparation of compounds of general formula (I) starting from an amide of formula II, as shown in Scheme 1, wherein $R_1$, $R_2$, $R_3$, $R_{3'}$, $R_{3''}$, $R_{3'''}$, $R_4$, $R_{4'}$, $R_5$, $R_{5'}$, $R_6$ and X have the meanings as defined above for a compound of formula (I), W represents a leaving group such as chloro or bromo and P represents a suitable protecting group, such as benzyl.

Scheme 1:

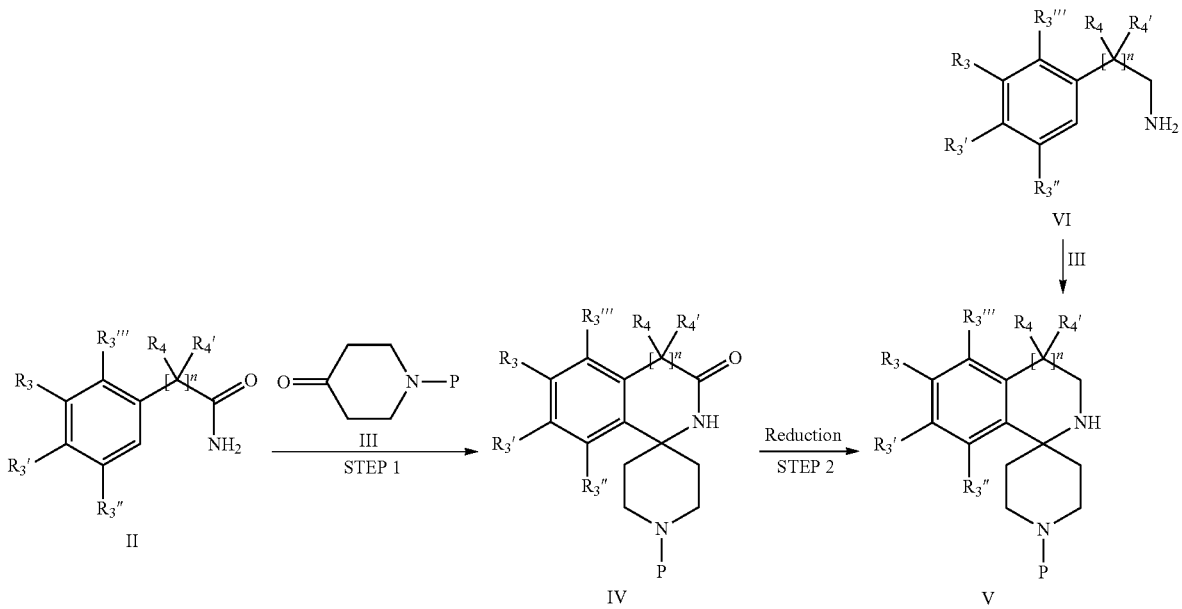

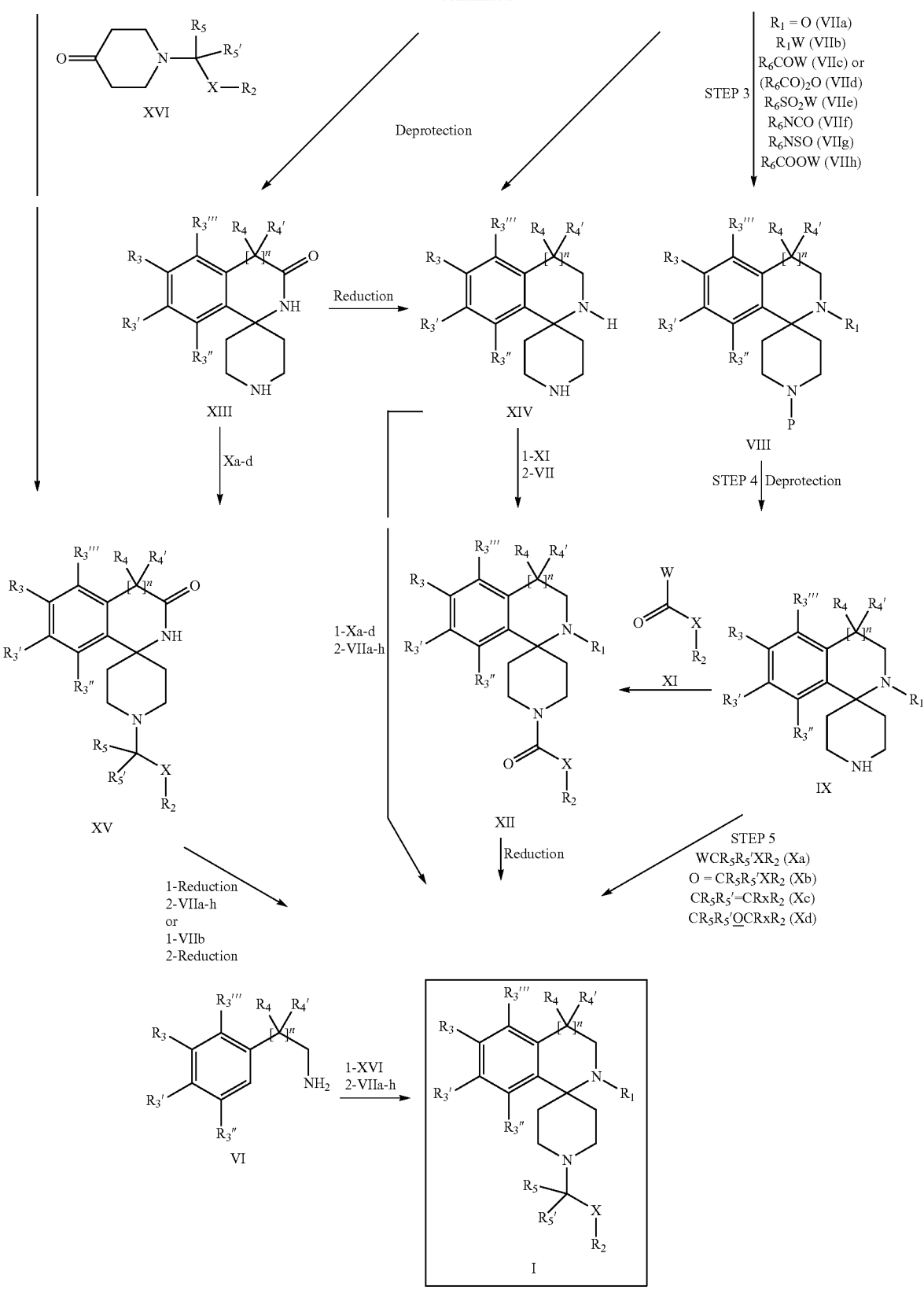

The 5-step process is carried out as described below:

Step 1: A compound of formula IV is prepared by treating a compound of formula II with a ketone of formula III, in a suitable solvent such as polyphosphoric acid, at a suitable temperature, preferably comprised between 80 and 120° C.

Step 2: A compound of formula V is prepared by reaction of a compound of formula IV with a reducing agent such as borane, in a suitable solvent such as toluene, at a suitable temperature comprised between room temperature and the reflux temperature, preferably at reflux temperature.

Other alternative reducing agents can be used, such as lithium aluminium hydride in a suitable solvent such as THF, at a suitable temperature comprised between room temperature and the reflux temperature, preferably at room temperature.

The compounds of formula V, in which some of $R_3$-$R_{3'''}$ is an electron donating group can also be prepared by reaction of a compound of formula VI with a compound of formula III under the conditions described in Step 1.

Step 3: A compound of formula VIII is prepared by reaction of a compound of formula V with any of the reagents VIIa to VIIh in order to introduce any of the groups present as $R_1$. Thus:

The reductive amination reaction between a compound of formula V and a compound of formula VIIa is carried out in the presence of a reductive reagent, preferably sodium triacetoxyborohydride, in a protic solvent, preferably methanol at a suitable temperature, preferably room temperature. Alternatively the reaction can be carried out in an aprotic solvent, preferably tetrahydrofuran or dichloroethane, in the presence of an acid, preferably acetic acid.

The alkylation reaction between a compound of formula V (or a suitable salt such as trifluoroacetate or hydrochloride) and a compound of formula VIIb is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The acylation reaction between a compound of formula V (or a suitable salt such as trifluoroacetate or hydrochloride) and a compound of formula VIIc is carried out in a suitable solvent, such as acetonitrile, dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.

Alternatively, the acylation reaction can be carried out by reaction with and anhydride of formula VIId, in a suitable solvent, such as dichloromethane; in the presence of an organic base such as pyridine at a suitable temperature, preferably reflux temperature.

The sulfonylation reaction between a compound of formula V (or a suitable salt such as trifluoroacetate or hydrochloride) and a compound of formula VIIe can be carried out in a suitable solvent, such as dichloroethane or dichoromethane; in the presence of an organic base such as pyridine and a catalytic amount of DMAP at a suitable temperature, preferably reflux temperature.

The formation of a urea or thiurea derivative by reaction between a compound of formula V (or a suitable salt such as trifluoroacetate or hydrochloride) and a compound of formula VIIf or VIIg, respectively, in a suitable solvent such as toluene, at a suitable temperature comprised between room temperature and the reflux temperature, preferably at reflux temperature.

The carbamoylation reaction between a compound of formula V (or a suitable salt such as trifluoroacetate or hydrochloride) and a compound of formula VIIh is carried out in a suitable solvent, such as acetonitrile, dichloromethane or ethyl acetate-water mixtures; in the presence of an organic base such as triethylamine or diisopropylethylamine or an inorganic base such as $K_2CO_3$, at a suitable temperature, preferably comprised between −78° C. and room temperature.

Step 4: A compound of formula IX is prepared by deprotection of a compound of formula VIII. If the protecting group is benzyl the deprotection is carried out with hydrogen at a pressure comprised between 1 and 10 bar, in a suitable solvent such as methanol or ethanol, optionally in the presence of an acid such as acetic or hydrochloric acid at a suitable temperature comprised between room temperature and the reflux temperature, preferably at room temperature.

Step 5: The compounds of formula I are prepared by reacting a compound of formula IX with a suitable reagent of formula Xa-d, using different conditions depending on the reagent nature. Thus: The alkylation reaction between a compound of formula IX (or a suitable salt such as trifluoroacetate or hydrochloride) and a compound of formula Xa is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The reductive amination reaction between a compound of formula IX and a compound of formula Xb is carried out in the presence of a reductive reagent, preferably sodium triacetoxyborohydride, in a protic solvent, preferably methanol at a suitable temperature, preferably room temperature. Alternatively the reaction can be carried out in an aprotic solvent, preferably tetrahydrofuran or dichloroethane, in the presence of an acid, preferably acetic acid.

The reaction between a compound of formula IX and a vinyl derivative of formula Xc is carried out in the presence of a protic solvent, preferably ethanol at a suitable temperature, preferably reflux temperature.

The reaction between a compound of formula IX and an epoxide derivative of formula Xd is carried out in a suitable solvent such as toluene, at a suitable temperature comprised between room temperature and the reflux temperature, preferably at reflux temperature.

Alternatively, the transformation of a compound of formula IX to a compound of formula I can be effected in a two step procedure, involving acylation of IX with a compound of formula XI to give a compound of formula XII, which is then reduced. The acylation reaction can be carried out using amide coupling conditions, such as, EDC/HOBT/DIPEA in a suitable solvent, such as DMF at a suitable temperature, preferably room temperature. The reduction reaction can be carried out as described in Step 2.

The process described by Steps 1 to 5 represents the most general route for the preparation of compounds of formula I. Alternatively the order of the different steps can be interchanged, as described in Scheme 1. Compound IV can be deprotected to give XIII, under the conditions described in Step 4, and then reduced to afford XIV, under the conditions described in Step 2. In its turn, XIV can be obtained on deprotection of V under the conditions described in Step 4. Intermediate XIV can be transformed to the final compound I, by reaction with Xa-d, under the conditions described in Step 5, followed by reaction with VIIa-h under the conditions described in Step 3. Alternatively, compound XIII can be reacted under the conditions described in Step 5, with reagents Xa-d, to afford intermediate XV, which in its turn can be obtained by direct reaction of II with conveniently functionalized ketones XVI. Intermediate XV can be transformed to the final compound I, by reduction, under the conditions described in Step 2, followed by reaction with VIIa-h under the conditions described in Step 3. In the case where $R_1$ is alkyl, the step order can be inverted and compound I can be obtained by reaction of intermediate XV with VIIb under the conditions described in Step 3, followed by reduction under the conditions described in Step 2.

Additionally, in the case where some of $R_3$-$R_3'''$ is an electron donating group, compound I can also be prepared The cyclization of a compound of formula XIX to give a compound of formula XX is carried out under palladium catalyzed conditions, such as using palladium acetate in the presence of triphenylphosphine and a base, such as potassium carbonate and tetrabutylammoium chloride in a suitable polar solvent such as acetonitrile, at a suitable temperature such as that of the solvent reflux.

The deprotection of a compound of formula XX to give a compound of formula XXI is carried out in trifluoroacetic acid at reflux temperature.

The reduction of a compound of formula XXI to give a compound of formula XXII is carried out using a suitable reducing agent such as sodiumtriacetoxyborohydride in the presence of an organic acid, such as acetic acid, in a suitable solvent, such as acetonitrile, at room temperature.

The protection of a compound of formula XXII to give a compound of formula IVa is carried out under suitable conditions depending on the protecting group used. As a matter of example, when P is a benzyl group, the protection is carried out under reductive amination conditions using benzaldehyde in the presence of a reductive reagent, preferably sodium triacetoxyborohydride, in a protic solvent, preferably methanol at a suitable temperature, preferably room temperature.

Scheme 2:

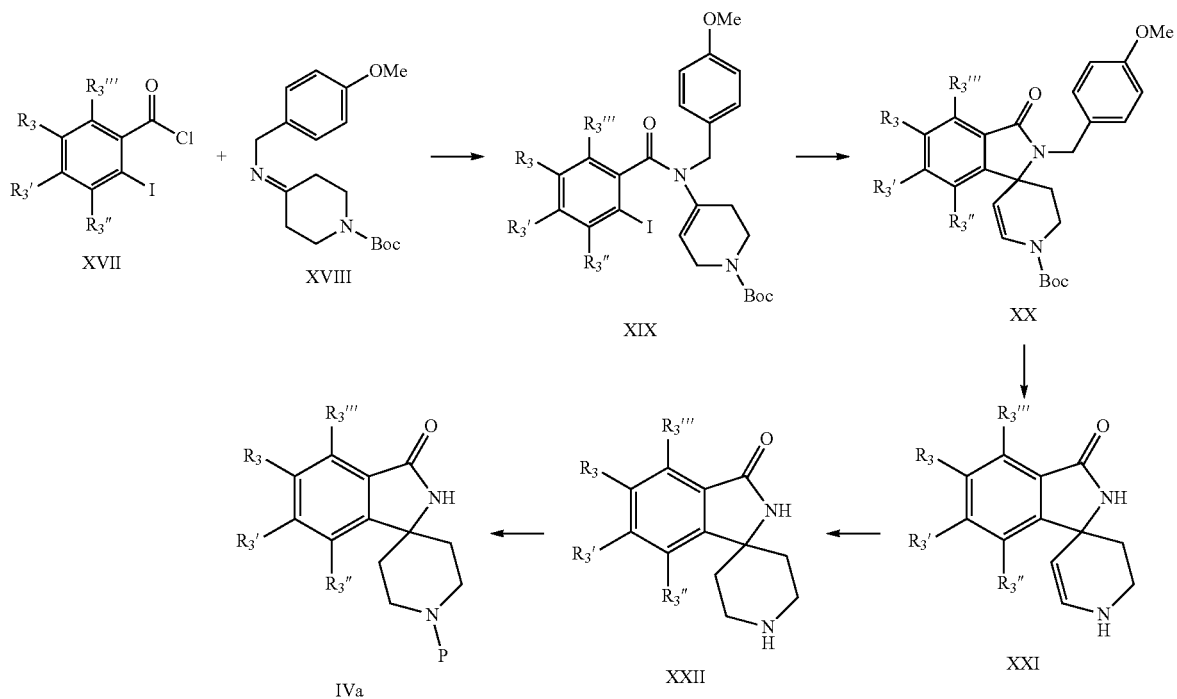

by reaction of a compound of formula VI with a compound of formula XVI under the conditions described in Step 1, followed by reaction with VIIa-h under the conditions described in Step 3.

Additionally, in the case where n=0, the compounds of formula IV can be obtained by the route outlined in Scheme 2.

The reaction of an imine derivative XVIII with a iodo derivative XVII is carried out in the presence of a base, such as triethylamine in an apolar solvent, such as toluene to give the iodo derivatives XIX.

Additionally, the functional groups present in any of the positions can be interconverted using reactions known to those skilled in the art. Examples of such transformations are reduction of the carbonyl group of the amides in $R_1$ to give alkyl derivatives in $R_1$, transformation of a methoxy group to a hydroxyl group, acylation of amino or alcohol to acylamino or acyloxy derivatives, reduction of a nitro group to an amino, etc. . . .

Compounds of formula II, III, VI, VII, X, XVI, XVII or XVIII where $R_1$, $R_2$, $R_3$, $R_3'$, $R_3''$, $R_3'''$, $R_4$, $R_4'$, $R_5$, $R_5'$, $R_6$, X and P have the meanings as defined above, are commercially available or can be prepared by conventional methods described in the bibliography.

EXAMPLES

The following abbreviations are used in the examples:
ACN: acetonitrile
AcOH: acetic acid
Boc: tert-butoxycarbonyl
DCM: dichloromethane
DEA: diethylamine
DIPEA: diisopropylethylamine
DMAP: Dimethylaminopyrimidine
DMF: dimethylformamide
DMSO: dimethylsulfoxide
EDC: N-(3-Dimethylaminopropyl)-N'-ethylcarbodiimide
Eq: equivalent
EtOH: ethanol
EX: example
h: hour/s
HPLC: high performance liquid chromatography
IPA: isopropanol
LDA: lithium diisopropylamide
MeOH: methanol
MS: mass spectrometry
Min.: minutes
Quant: quantitative
Ret.: retention time
r.t.: room temperature
Sat: saturated
s.m.: starting material
TEA: triethylamine
TFA: trifluoroacetic acid
THF: tetrahydrofuran The following methods were used to determine the HPLC-MS spectra:
A: Column XBridge C18 3.5 μm, 2.1×50 mm; flow rate: 0.3 mL/min; A: ACN:MeOH (1:1); B: Water; C: 100 mM Ammonium acetate pH 7; gradient A:B:C: 2 min in 10:85:5+from 10:85:5 to 95:0:5 in 6 min+7 min in 95:0:5
B: Column SunFire C18 3.5 μm, 2.1×100 mm; flow rate: 0.3 mL/min; A: ACN:MeOH (1:1); B: Water; C: 100 mM Ammonium acetate pH 7; gradient A:B:C: 3 min in 10:85:5+from 10:85:5 to 95:0:5 in 17 min+10 min in 95:0:5.
B1: column SunFire C18 5 μm, 2.1×50 mm; flow rate: 0.3 mL/min; A: ACN:MeOH (1:1); B: Water; C: 100 mM Ammonium acetate pH 7; gradient A:B:C: 2 min in 10:85:5+from 10:85:5 to 95:0:5 in 6 min+7 min in 95:0:5.
C: Column Symmetry C18 3.5 μm, 2.1×100 mm; flow rate: 0.3 mL/min; A: ACN:MeOH (1:1); B: Water; C: 100 mM Ammonium acetate pH 7; gradient A:B:C: 3 min in 10:85:5+from 10:85:5 to 95:0:5 in 17 min+10 min in 95:0:5
D: Column XTerra MS C18 3.5 μm, 2.1×100 mm; flow rate: 0.3 mL/min; A: ACN:MeOH (1:1); B: Water; C: 100 mM Ammonium acetate pH 9 (NH$_4$OH); gradient A:B:C: 3 min in 10:85:5+from 10:85:5 to 95:0:5 in 17 min+10 min in 95:0:5.
E: Column Kinetex C18 5 μm, 2.1×150 mm; flow rate: 0.35 mL/min; A: ACN:MeOH (1:1); B: Water; C: 100 mM Ammonium acetate pH 7; gradient A:B:C: 5 min in 5:90:5+from 5:90:5 to 95:0:5 in 15 min+10 min in 95:0:5

F: Column: Xbridge C$_{18}$ XP 30×4.6 mm, 2.5 um; flow: 2.0 mL/min; gradient: NH$_4$HCO$_3$ pH 8: ACN (95:5)—0.5 min—(95:5)—6.5 min—(0:100)—1 min—(0:100). Sample dissolved aprox. 1 mg/mL in NH$_4$HCO$_3$ pH 8/ACN H: Column: Aqcuity UPLC BEH C18 2.1×50 mm 1.7 μm; flow rate: 0.61 mL/min; A: NH4HCO3 10 mM; B: ACN; gradient: 0.3 min in 98% A, 98% A to 5% A in 2.52 min, 1.02 min in 5% A, 5% A to 98% A in 0.34 min, 0.57 min in 98% A.

i: Column Gemini-NX 30×4.6 mm, 3 um; Temperature: 40° C.; Flow: 2.0 mL/min; Gradient: NH$_4$HCO$_3$ pH 8: ACN (95:5)—0.5 min—(95:5)—6.5 min—(0:100)—1 min—(0:100).

Synthesis of Intermediates

Intermediate 1A.

1'-Benzyl-2H-spiro[isoquinoline-1,4'-piperidin]-3(4H)-one

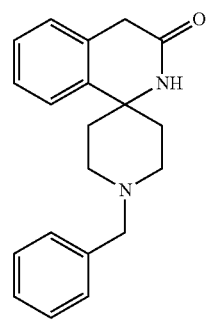

A mixture of 2-phenylacetamide (10 g, 73.98 mmol), 1-benzylpiperidin-4-one (21 g, 110.97 mmol) and PPA (200 g) was stirred at 100° C. for 24 h. Additional 1-benzylpiperidin-4-one (7 g, 36.99 mmol) was added and the reaction mixture was stirred at 100° C. until full conversion was achieved (3 days, checked by HPLC analysis). It was cooled down to 50° C. and slowly poured into H$_2$O/ice (600 g). NaOH 36% aqueous solution (100 mL) was added until pH=7-8. The mixture was stirred for 10 min and the aqueous layer was extracted with DCM. The combined organic layers were dried over Na$_2$SO$_4$, filtered and concentrated. The crude residue was purified by flash chromatography on silica-gel (30→40% acetone/hexanes), to give 21.21 g of a solid, which was slurred with MeOH/Et$_2$O (20%, 60 mL), filtered and eluted with Et$_2$O, to give the title compound as a yellow solid (14.53 g, yield 64%).

HPLC-MS (Method A): Ret, 8.66 min; ESI$^+$-MS m/z, 307.3 (M+1).

This method was used for the preparation of intermediates 1B-1C using suitable starting materials:

| EX | Structure | Chemical name | Method | Ret (min) | MS (M + H) |
|---|---|---|---|---|---|
| 1B | 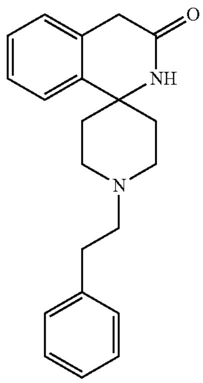 [SMILES: O=C1Cc2ccccc2C2(CCN(CCc3ccccc3)CC2)N1] | 1'-phenethyl-2H-spiro[isoquinoline-1,4'-piperidin]-3(4H)-one | B | 15.45 | 321.3 |
| 1C | 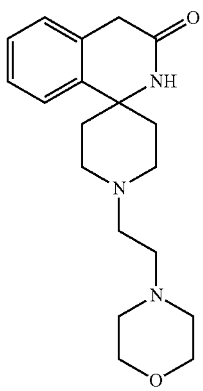 [SMILES: O=C1Cc2ccccc2C2(CCN(CCN3CCOCC3)CC2)N1] | 1'-(2-Morpholino-ethyl)-2H-spiro[isoquinoline-1,4'-piperidin]-3(4H)-one | C | 10.7 | 330.2 |

Intermediate 1 D.

1'-((Tetrahydro-2H-pyran-4-yl)methyl)-2H-spiro[isoquinoline-1,4'-piperidin]-3(4H)-one

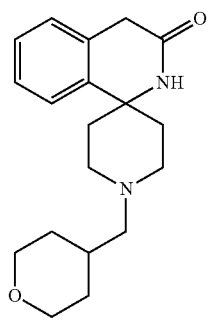 [SMILES: O=C1Cc2ccccc2C2(CCN(CC3CCOCC3)CC2)N1]

a) 2H-Spiro[isoquinoline-1,4'-piperidin]-3(4H)-one

1'-Benzyl-2H-spiro[isoquinoline-1,4'-piperidin]-3(4H)-one (intermediate 1A 5.06 g, 16.51 mmol) was added to a suspension of Pd(OH)₂ (2.39 g, 20% Pd, 48.40% H₂O w/w, 1.65 mmol) and AcOH (94 μL, 1.65 mmol) in MeOH (90 mL). The suspension was stirred under H₂ atmosphere for 19 h. The reaction mixture was filtered through Celite, washed with MeOH and concentrated, to furnish 2H-spiro[isoquinoline-1,4'-piperidin]-3(4H)-one (3.49 g, yield 98%).

HPLC-MS (Method D): Ret, 14.13 min; ESI⁺-MS m/z, 217.1 (M+1).

b) 1'-((Tetrahydro-2H-pyran-4-yl)methyl)-2H-spiro[isoquinoline-1,4'-piperidin]-3(4H)-one AcOH (118 mL, 2.07 mmol) was added to a solution of the previous compound (50 mg, 0.23 mmol) and tetrahydro-2H-pyran-4-carbaldehyde (52 mg, 0.46 mmol) in DCM (10 mL). The mixture was stirred at r.t. for 20 h and NaB(OAc)₃H (97 mg, 0.46 mmol) was added. The solution was stirred until full conversion was achieved (20 h, TLC analysis), poured into NaHCO₃ saturated aqueous solution (15 mL) and extracted with DCM. The combined organic layers were dried over Na₂SO₄, filtered and concentrated. The crude residue was purified by flash chromatography on SiO₂ (4% MeOH/DCM), to give the title compound (61 mg, yield 85%).

HPLC-MS (Method A): Ret, 6.98 min; ESI⁺-MS m/z, 315.2 (M+1).

Intermediate 1E.

1'-(2-(Methyl(phenyl)amino)ethyl)-2H-spiro[isoquinoline-1,4'-piperidin]-3(4H)-one

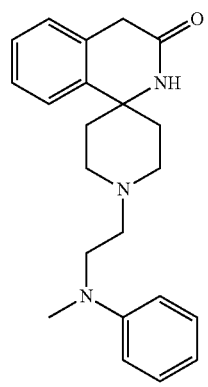 [SMILES: CN(CCN1CCC2(CC1)NC(=O)Cc1ccccc12)c1ccccc1]

N-2-bromoethyl-N-methylaniline (235.4 mg, 1.10 mmol) was added to a suspension of 2H-spiro[isoquinoline-1,4'-piperidin]-3(4H)-one (obtained in the synthesis of intermediate 1 D, step a, 200 mg, 0.92 mmol) and K₂CO₃ (381 mg, 2.76 mmol) in ACN (8 mL). The reaction mixture was refluxed for 20 h and it was cooled down to r.t., poured into H₂O (10 mL) and extracted with EtOAc. The combined organic layers were washed with H₂O, dried over Na₂SO₄, filtered and concentrated. The crude residue was purified by flash chromatography on SiO₂ (mobile phase: MeOH/DCM), to give the title compound (268.7 mg, yield 70%).

HPLC-MS (Method A): Ret, 8.91 min; ESI⁺-MS m/z, 350.2 (M+1).

This method was used for the preparation of intermediates 1F-1U using suitable alkylating agents:

| INT | Structure | Chemical name | Method | Ret time (min) | MS (M + H |
|---|---|---|---|---|---|
| 1F | 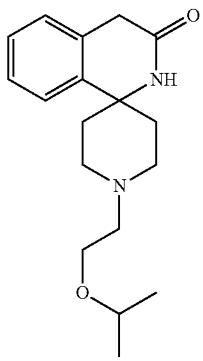 [SMILES: CC(C)OCCN1CCC2(CC1)NC(=O)Cc1ccccc12] | 1'-(2-isopropoxyethyl)-2H-spiro[isoquinoline-1,4'-piperidin]-3(4H)-one | A | 7.59 | 303.1 |
| 1G | 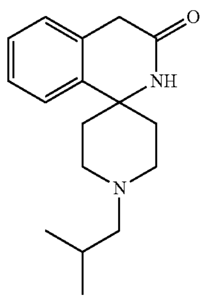 [SMILES: CC(C)CN1CCC2(CC1)NC(=O)Cc1ccccc12] | 1'-isobutyl-2H-spiro[isoquinoline-1,4'-piperidin]-3(4H)-one | A | 7.90 | 286.9 |
| 1H | 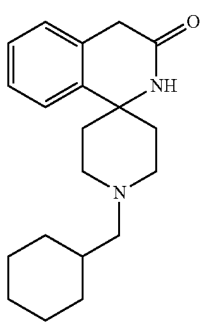 [SMILES: O=C1Cc2ccccc2C2(CCN(CC3CCCCC3)CC2)N1] | 1'-(cyclohexylmethyl)-2H-spiro[isoquinoline-1,4'-piperidin]-3(4H)-one | A | 8.93 | 313.2 |
| 1I | 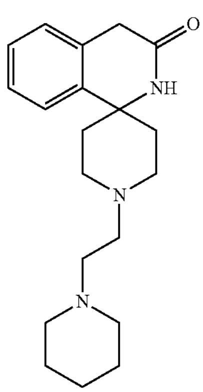 [SMILES: O=C1Cc2ccccc2C2(CCN(CCN3CCCCC3)CC2)N1] | 1'-(2-(piperidin-1-yl)ethyl)-2H-spiro[isoquinoline-1,4'-piperidin]-3(4H)one | A | 6.75 | 328.1 |

-continued

| INT | Structure | Chemical name | Method | Ret time (min) | MS (M + H) |
|---|---|---|---|---|---|
| 1J | 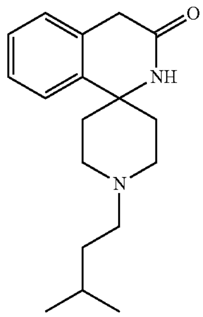 [SMILES: CC(C)CCN1CCC2(CC1)NC(=O)Cc1ccccc12] | 1'-isopentyl-2H-spiro[isoquinoline-1,4'-piperidin]-3(4H)-one | A | 7.90 | 286.9 |
| 1K | 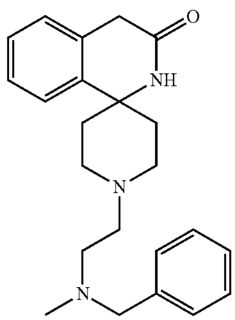 [SMILES: CN(CCN1CCC2(CC1)NC(=O)Cc1ccccc12)Cc1ccccc1] | 1'-(2-(benzyl(methyl)amino)ethyl)-2H-spiro[isoquinoline-1,4'-piperidin]-3(4H)-one | A | 8.10 | 363.8 |
| 1L | 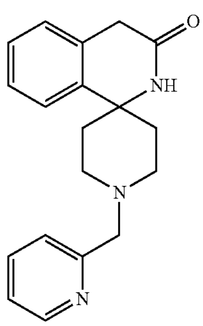 [SMILES: O=C1Cc2ccccc2C2(CCN(Cc3ccccn3)CC2)N1] | 1'-(pyridin-2-ylmethyl)-2H-spiro[isoquinoline-1,4'-piperidin]-3(4H)-one | C | 13.21 | 307.8 |
| 1M | 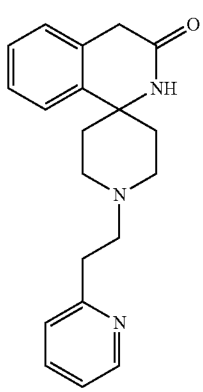 [SMILES: O=C1Cc2ccccc2C2(CCN(CCc3ccccn3)CC2)N1] | 1'-(2-(pyridin-2-yl)ethyl)-2H-spiro[isoquinoline-1,4'-piperidin]-3(4H)-one | A | 7.26 | 321.9 |

-continued
| INT | Structure | Chemical name | Method | Ret time (min) | MS (M + H) |
|---|---|---|---|---|---|
| 1N | 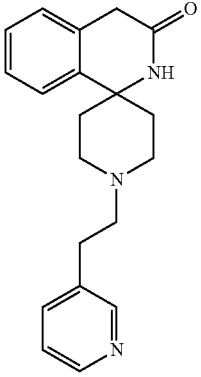 | 1'-(2-(pyridin-3-yl)ethyl)-2H-spiro[isoquinoline-1,4'-piperidin]-3(4H)-one | A | 7.23 | 322.1 |
| 1O | 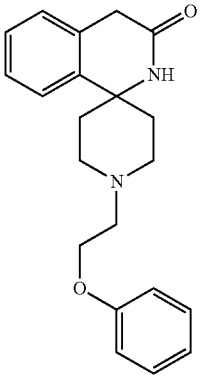 | 1'-(2-phenoxyethyl)-2H-spiro[isoquinoline-1,4'-piperidin]-3(4H)-one | B1 | 8.62 | 337.2 |
| 1P* | 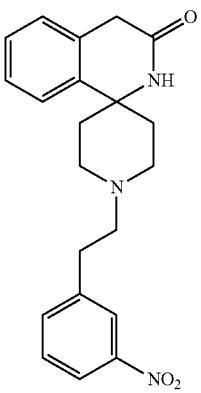 [SMILES: O=C1Cc2ccccc2C2(CCN(CCc3cccc([N+](=O)[O-])c3)CC2)N1] | 1'-(3-nitrophenethyl)-2H-spiro[isoquinoline-1,4'-piperidin]-3(4H)-one | — | — | — |

| INT | Structure | Chemical name | Method | Ret time (min) | MS (M + H |
|---|---|---|---|---|---|
| 1Q | 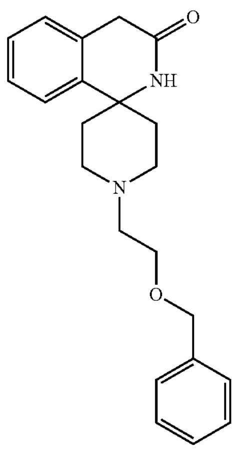 [SMILES: O=C1Cc2ccccc2C2(CCN(CCOCc3ccccc3)CC2)N1] | 1'-(2-(benzyloxy)ethyl)-2H-spiro[isoquinoline-1,4'-piperidin]-3(4H)-one | F | 364 | 351.1 |
| 1R | 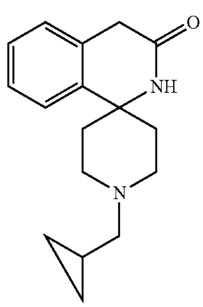 [SMILES: O=C1Cc2ccccc2C2(CCN(CC3CC3)CC2)N1] | 1'-(cyclopropylmethyl)-2H-spiro[isoquinoline-1,4'-piperidin]-3(4H)-one | F | 2.85 | 271.1 |
| 1S | 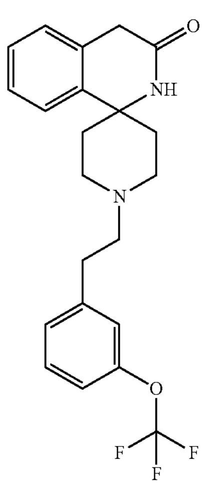 [SMILES: O=C1Cc2ccccc2C2(CCN(CCc3cccc(OC(F)(F)F)c3)CC2)N1] | 1'-(3-(trifluoromethoxy)phenethyl)-2H-spiro[isoquinoline-1,4'-piperidin]-3(4H)-one | F | 4.46 | 405.1 |

| INT | Structure | Chemical name | Method | Ret time (min) | MS (M + H) |
|---|---|---|---|---|---|
| 1T | 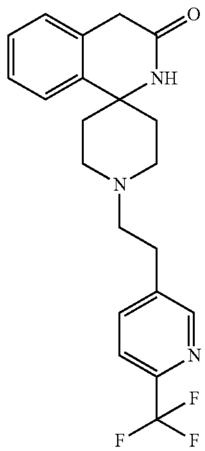 [SMILES: O=C1Cc2ccccc2C2(CCN(CCc3ccc(C(F)(F)F)nc3)CC2)N1] | 1'-(2-(6-(trifluoromethyl)pyridin-3-yl)ethyl)-2H-spiro[isoquinoline-1,4'-piperidin]-3(4H)-one | F | 3.63 | 390.1 |
| 1U | 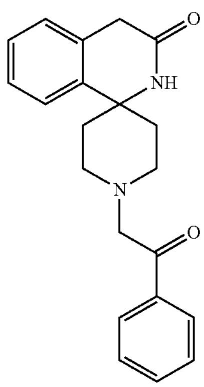 [SMILES: O=C1Cc2ccccc2C2(CCN(CC(=O)c3ccccc3)CC2)N1] | 1'-(2-oxo-2-phenylethyl)-2H-spiro[isoquinoline-1,4'-piperidin]-3(4H)-one | F | 3.39 | 335.1 |

Intermediate 1P*: RMN-¹H: ¹H-NMR (CDCl₃, 500 MHz, 6): 8.14 (bs, 1H, ArH); 8.09 (d, J=7.7 Hz, 1H, ArH); 7.56 (d, J=7.7 Hz, 1H, ArH); 7.48 (t, J=7.7 Hz, 1H, ArH); 7.39 (d, J=7.7 Hz, 1H, ArH); 7.29 (m, 2H, ArH); 7.17 (d, J=7.7 Hz, 1H, ArH); 6.41 (bs, 1H, NH); 3.66 (s, 2H, CH₂); 3.01-2.93 (m, 4H, CH₂); 2.72 (d, J=7.7 Hz, 2H, CH₂); 2.38 (d, J=12.0 Hz, 2H, CH₂); 2.25 (m, 2H, CH₂); 1.84 (m, 2H, CH₂).

Intermediate 2A.

6-Methoxy-1'-phenethyl-3,4-dihydro-2H-spiro[isoquinoline-1,4'-piperidine]

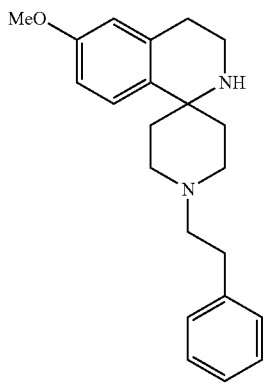 [SMILES: COc1ccc2c(c1)CCNC21CCN(CCc2ccccc2)CC1]

1-Phenethylpiperidin-4-one (3.09 g, 15 mmol) was slowly added to a solution of 2-(3-methoxyphenyl)ethanamine (2 g, 13 mmol) in phosphoric acid (12 mL), and the reaction mixture was heated under reflux for 16 hours. Then, it was cooled down to r.t., poured carefully into ice/water, and diluted with dichloromethane. The mixture was basified using concentrated sodium hydroxide solution, and extracted with dichlorometane. The combined organic layers were dried over Na₂SO₄, filtered and concentrated to dryness, to give the title compound (3.5 g, yield 79%). HPLC-MS (Method H): Ret, 1.78 min; ESI⁺-MS m/z, 350.2 (M+1).

Intermediate 2B.

1'-Benzyl-3,4-dihydro-2H-spiro[isoquinoline-1,4'-piperidine]

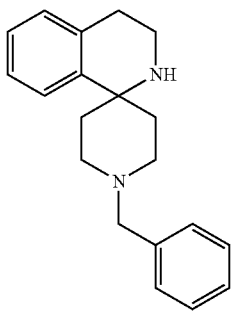 [SMILES: c1ccc(CN2CCC3(CC2)NCCc2ccccc23)cc1]

A solution of BH$_3$.SMe$_2$ in toluene (10 M, 5.8 mL, 61.22 mmol) was added to a solution of 1'-benzyl-2H-spiro[isoquinoline-1,4'-piperidin]-3(4H)-one (intermediate 1A, 9.38 g, 30.61 mmol) in toluene (120 mL) and the reaction mixture was refluxed for 17 h. It was cooled down to r.t., 10% aqueous solution of HCl (19 mL) was added, and the suspension was stirred for 5 min. MeOH (75 mL) was added and the mixture was stirred for 45 min at reflux temperature. After cooling down to r.t., the mixture was poured into NaOH (10% aqueous solution, pH 9-10) and extracted with DCM. The combined organic layers were dried over Na$_2$SO$_4$, filtered and concentrated. The crude residue was purified by flash chromatography on silica-gel (3→10% MeOH/DCM and 2→10% MeOH/DCM), to give the title compound (6.8 g, yield 69%).

HPLC-MS (Method A): Ret, 8.38 min; ESI$^+$-MS m/z, 292.7 (M+1).

This method was used for the preparation of intermediates 2C-2V:

| INT | Structure | Chemical name | Method | Ret (min) | MS (M + H) |
|---|---|---|---|---|---|
| 2C | 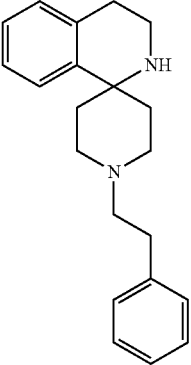 [SMILES: c1ccc(CCN2CCC3(CC2)NCCc2ccccc23)cc1] | 1'-(2-Phenylethyl)-3,4-dihydro-2H-spiro[isoquinoline-1,4'-piperidine] | B | 9.55 | 307.1 |
| 2D | 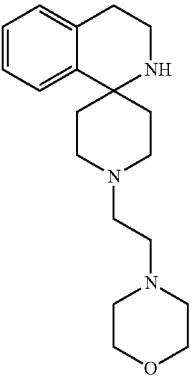 [SMILES: c1ccc2c(c1)CCNC21CCN(CCN2CCOCC2)CC1] | 4-(2-(3,4-dihydro-2H-spiro[isoquinoline-1,4'-piperidin]-1'yl)ethyl)morpholine | A | 6.75 | 316.2 |
| 2E | 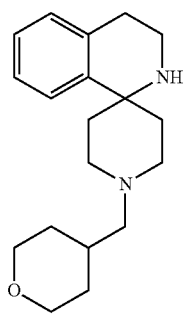 [SMILES: c1ccc2c(c1)CCNC21CCN(CC2CCOCC2)CC1] | 1'-((tetrahydro-2H-pyran-4-yl)methyl)-3,4-dihydro-2H-spiro[isoquinoline-1,4'-piperidine] | A | 6.97 | 301.0 |

-continued

| INT | Structure | Chemical name | Method | Ret (min) | MS (M + H) |
|---|---|---|---|---|---|
| 2F | 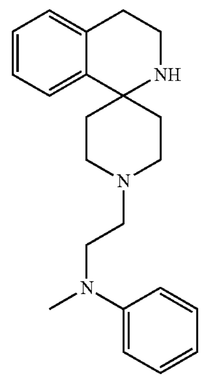 [SMILES: CN(CCN1CCC2(CC1)NCCc1ccccc12)c1ccccc1] | N-(2-(3,4-dihydro-2H-spiro[isoquinoline-1,4'-piperidine]-1'-yl)ethyl)-N-methylaniline | A | 8.92 | 335.9 |
| 2G | 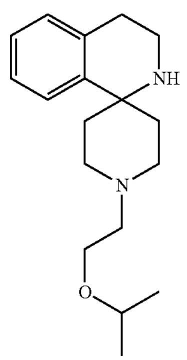 [SMILES: CC(C)OCCN1CCC2(CC1)NCCc1ccccc12] | 1'-(2-isopropoxyethyl)-3,4-dihydro-2H-spiro[isoquinoline-1,4'-piperidine] | A | 7.62 | 289.1 |
| 2H | 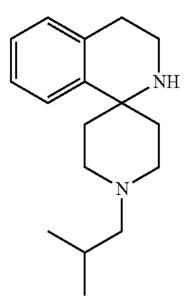 [SMILES: CC(C)CN1CCC2(CC1)NCCc1ccccc12] | 1'-isobutyl-3,4-dihydro-2H-spiro[isoquinoline-1,4'-piperidine] | A | 7.30 | 258.8 |
| 2I | 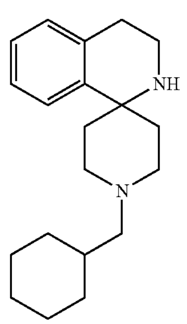 [SMILES: c1ccc2c(c1)CCNC21CCN(CC2CCCCC2)CC1] | 1'-(cyclohexylmethyl)-3,4-dihydro-2H-spiro[isoquinoline-1,4'-piperidine] | A | 8.42 | 298.7 |

-continued

| INT | Structure | Chemical name | Method | Ret (min) | MS (M + H) |
|---|---|---|---|---|---|
| 2J | 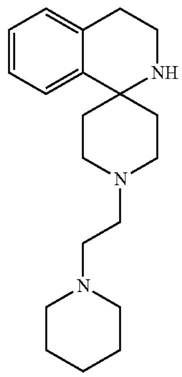 [SMILES: c1ccc2c(c1)CCNC21CCN(CCN2CCCCC2)CC1] | 1'-(2-(piperidin-1-yl)ethyl)-3,4-dihydro-2H-spiro[isoquinoline-1,4'-piperidine] | A | 7.02 | 314.0 |
| 2K | 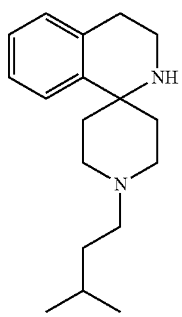 [SMILES: CC(C)CCN1CCC2(CC1)NCCc1ccccc12] | 1'-isopentyl-3,4-dihydro-2H-spiro[isoquinoline-1,4'-piperidine] | A | 7.71 | 272.9 |
| 2L | 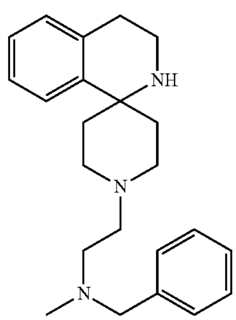 [SMILES: CN(CCN1CCC2(CC1)NCCc1ccccc12)Cc1ccccc1] | N-benzyl-2-(3,4-dihydro-2H-spiro[isoquinoline-1,4'-piperidine]-1'-yl)-N-methylethanamine | A | 8.39 | 350.2 |
| 2M | 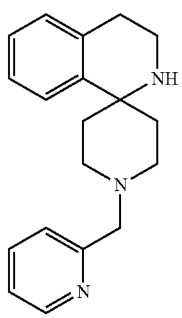 [SMILES: c1ccc(CN2CCC3(CC2)NCCc2ccccc23)nc1] | 1'-(pyridin-2-ylmethyl)-3,4-dihydro-2H-spiro[isoquinoline-1,4'-piperidine] | C | 14.76 | 293.9 |

-continued
| INT | Structure | Chemical name | Method | Ret (min) | MS (M + H) |
|---|---|---|---|---|---|
| 2N | 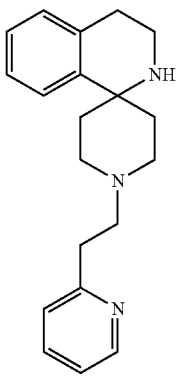 [SMILES: c1ccc(CCN2CCC3(CC2)NCCc2ccccc23)nc1] | 1'-(2-(pyridin-2-yl)ethyl)-3,4-dihydro-2H-spiro[isoquinoline-1,4'-piperidine] | A | 7.36 | 308.1 |
| 2O | 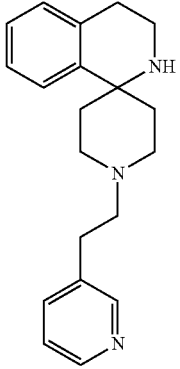 [SMILES: c1cncc(CCN2CCC3(CC2)NCCc2ccccc23)c1] | 1'-(2-(pyridin-3-yl)ethyl)-3,4-dihydro-2H-spiro[isoquinoline-1,4'-piperidine] | A | 7.27 | 308.3 |
| 2P | 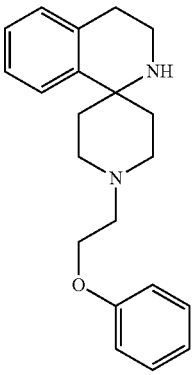 [SMILES: c1ccc(OCCN2CCC3(CC2)NCCc2ccccc23)cc1] | 1'-(2-phenoxyethyl)-3,4-dihydro-2H-spiro[isoquinoline-1,4'-piperidine] | A | 8.61 | 323.2 |
| 2Q | 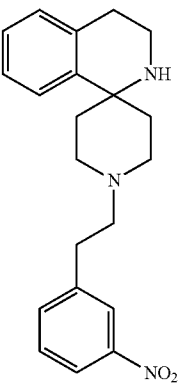 [SMILES: O=[N+]([O-])c1cccc(CCN2CCC3(CC2)NCCc2ccccc23)c1] | 1'-(3-nitrophenethyl)-3,4-dihydro-2H-spiro[isoquinoline-1,4'-piperidine] | A | 8.54 | 351.9 |

-continued

| INT | Structure | Chemical name | Method | Ret (min) | MS (M + H) |
|---|---|---|---|---|---|
| 2R | 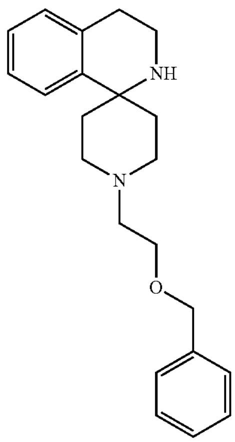 [SMILES: c1ccc(COCCN2CCC3(CC2)NCCc2ccccc23)cc1] | 1'-(2-(benzyloxy)ethyl)-3,4-dihydro-2H-spiro[isoquinoline-1,4'-piperidine] | F | 3.93 | 337.2 |
| 2S | 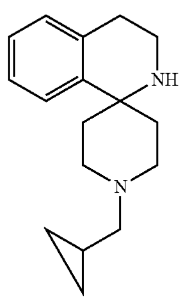 [SMILES: c1ccc2c(c1)CCNC21CCN(CC2CC2)CC1] | 1'-(cyclopropylmethyl)-3,4-dihydro-2H-spiro[isoquinoline-1,4'-piperidine] | F | 2.84 | 257.1 |
| 2T | 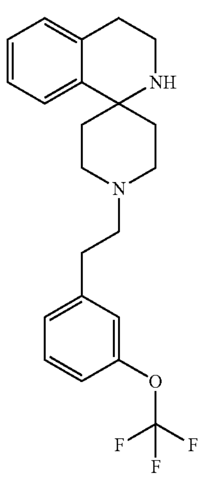 [SMILES: FC(F)(F)Oc1cccc(CCN2CCC3(CC2)NCCc2ccccc23)c1] | 1'-(3-(trifluoromethoxy)phenethyl)-3,4-dihydro-2H-spiro[isoquinoline-1,4'-piperidine] | F | 4.81 | 391.1 |

| INT | Structure | Chemical name | Method | Ret (min) | MS (M + H) |
|---|---|---|---|---|---|
| 2U | 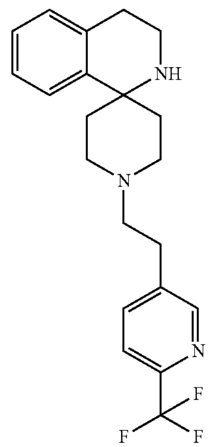 [SMILES: FC(F)(F)c1ccc(CCN2CCC3(CC2)NCCc2ccccc23)cn1] | 1'-(2-(6-(trifluoromethyl)pyridin-3-yl)ethyl)-3,4-dihydro-2H-spiro[isoquinoline-1,4'-piperidine] | F | 3.97 | 376.0 |
| 2V | 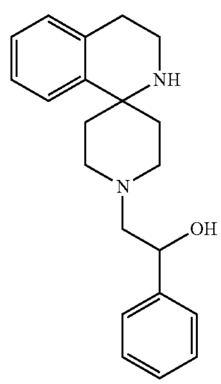 [SMILES: OC(CN1CCC2(CC1)NCCc1ccccc12)c1ccccc1] | 2-(3,4-dihydro-2H-spiro[isoquinoline-1,4'-piperidine]-1'-yl)-1-phenylethanol | F | 3.57 | 323.1 |

Intermediate 2W.

1'-(2-(Pyridin-4-yl)ethyl)-3,4-dihydro-2H-spiro[isoquinoline-1,4'-piperidine]

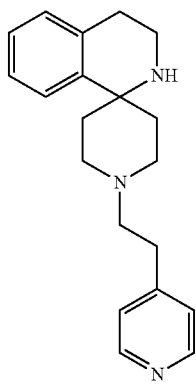 [SMILES: c1ccc2c(c1)CCNC21CCN(CCc2ccncc2)CC1]

a) 3,4-Dihydro-2H-spiro[isoquinoline-1,4'-piperidine]

1'-Benzyl-3,4-dihydro-2H-spiro[isoquinoline-1,4'-piperidine] (intermediate 2B, 1.27 g, 4.34 mmol) was added to a suspension of Pd(OH)$_2$ (629 mg, 20% Pd, 48.40% H$_2$O w/w, 0.434 mmol) and AcOH (25 µL, 0.434 mmol) in MeOH (15 mL). The suspension was stirred under H$_2$ atmosphere (balloon) for 24 h. The reaction mixture was filtered through Celite, rinsed with MeOH and concentrated, to furnish 3,4-dihydro-2H-spiro[isoquinoline-1,4'-piperidine] as an off-white solid (895 mg, yield 98%).

HPLC-MS (Method E): Ret, 3.25 min; ESI$^+$-MS m/z, 203.2 (M+1).

b) 1-(3,4-Dihydro-2H-spiro[isoquinoline-1,4'-piperidin]-1'-yl)-2-(pyridin-4-yl)ethanone HOBt (33% H$_2$O w/w, 1.0 g, 5.00 mmol), EDC (1.47 g, 7.70 mmol) and DIPEA (2.0 mL, 11.7 mmol) were added to a solution of pyridin-4-yl-acetic acid hydrochloride (601 mg, 3.46 mmol) in DMF (10 mL). The mixture was stirred at r.t. for 10 min and a solution of the compound obtained in step a, (795 mg, 3.85 mmol) in DMF (8 mL) was added. The reaction mixture was stirred at r.t. for 21 h, the solvent was concentrated and the residue was purified by medium pressure flash chromatography (MeOH/H$_2$O), to furnish 1-(3,4-dihydro-2H-spiro[isoquinoline-1,4'-piperidin]-1'-yl)-2-(pyridin-4-yl)ethanone as a yellow oil (465 mg, 42% yield).

HPLC-MS (Method E): Ret, 14.34 min; ESI$^+$-MS m/z, 322.1 (M+1).

c) Title Compound

LiAlH$_4$ solution (1.0 M in THF, 1.05 mL, 1.05 mmol) was added at 0° C. to a solution of the previous compound (226 mg, 0.703 mmol) in THF (14 mL). The reaction mixture was allowed to reach r.t. and stirred at this temperature for 2.5 h. The mixture was cooled down to 0° C., H$_2$O (35 mL), NaOH (15% aqueous solution, 35 mL) and H$_2$O (105 mL) were added and the suspension was stirred at 0° C. for 10 min. The mixture was filtered and rinsed with EtOAc and EtOH. The filtrate was concentrated off and the crude residue was purified by medium pressure flash chromatography (MeOH/H$_2$O), to give 1'-(2-(pyridin-4-yl)ethyl)-3,4-dihydro-2H-spiro[isoquinoline-1,4'-piperidine] as a white solid (59 mg, yield 26%).

HPLC-MS (Method E): Ret, 13.96 min; ESI+-MS m/z, 307.8 (M+1).

Intermediate 2X.

2-(3,4-Dihydro-2H-spiro[isoquinoline-1,4'-piperidine]-1'-yl)-1-morpholinoethanone

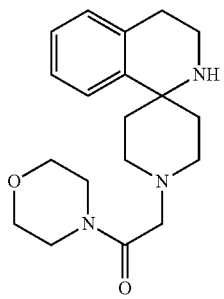 [SMILES: O=C(CN1CCC2(CC1)NCCc1ccccc12)N1CCOCC1]

A mixture of 3,4-dihydro-2H-spiro[isoquinoline-1,4'-piperidine] (obtained in the synthesis of intermediate 2W step a, 88 mg, 0.43 mmol), 4-(chloroacetyl)morpholine (0.06 mL, 0.45 mmol) and K$_2$CO$_3$ (150 mg, 1.09 mmol) in ACN (5 mL) was stirred at room temperature overnight. It was diluted with water and extracted with EtOAc. The combined organic layers were washed with brine, dried over MgSO$_4$, filtered and concentrated to dryness to give the title compound (121 mg, yield 84%).

HPLC-MS (Method F): Ret, 2.85 min; ESI$^+$-MS m/z, 330.2 (M+1).

This method was used for the preparation of examples 2Y-2AM using suitable starting materials:

| INT | Structure | Chemical name | Method | Ret (min) | MS (M + H) |
|---|---|---|---|---|---|
| 2Y | 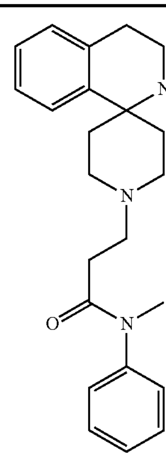 | 3-(3,4-dihydro-2H-spiro[isoquinoline-1,4'-piperidine]-1'-yl)-N-methyl-N-phenyl-propanamide | F | 3.53 | 364.2 |
| 2Z | 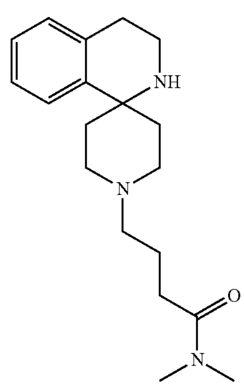 [SMILES: CN(C)C(=O)CCCN1CCC2(CC1)NCCc1ccccc12] | 4-(3,4-dihydro-2H-spiro[isoquinoline-1,4'-piperidine]-1'-yl)-N,N-dimethyl-butanamide | F | 2.57 | 316.1 |

-continued
| INT | Structure | Chemical name | Method | Ret (min) | MS (M + H) |
|---|---|---|---|---|---|
| 2AA | 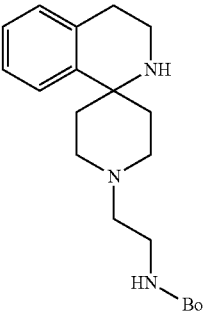 | tert-butyl 2-(3,4-dihydro-2H-spiro[isoquinoline-1,4'-piperidine]-1'-yl)ethyl-carbamate | F | 3.62 | 346.1 |
| 2AB | 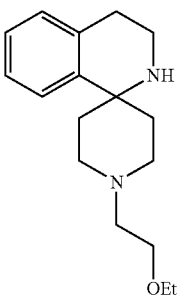 [SMILES: CCOCCN1CCC2(CC1)NCCc1ccccc12] | 1'-(2-ethoxyethyl)-3,4-dihydro-2H-spiro[isoquinoline-1,4'-piperidine] | F | 2.94 | 275.2 |
| 2AC | 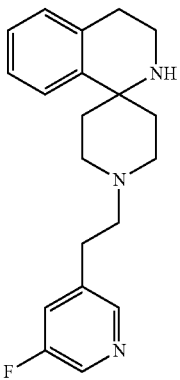 | 1'-(2-(5-fluoropyridin-3-yl)ethyl)-3,4-dihydro-2H-spiro[isoquinoline-1,4'-piperidine] (*) | F | 3.37 | 326.2 |
| 2AD | 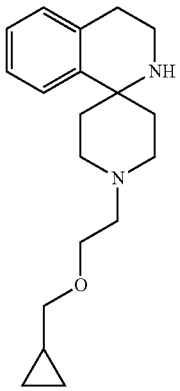 [SMILES: c1ccc2c(c1)CCNC21CCN(CCOCC2CC2)CC1] | 1'-(2-(cyclopropyl-methoxy)ethyl)-3,4-dihydro-2H-spiro[isoquinoline-1,4'-piperidine] (*) | F | 3.40 | 301.2 |

| INT | Structure | Chemical name | Method | Ret (min) | MS (M + H) |
|---|---|---|---|---|---|
| 2AE | 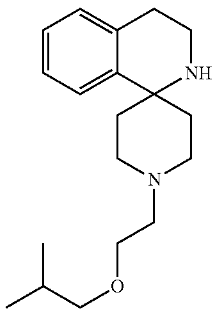 [SMILES: CC(C)COCCN1CCC2(CC1)NCCc1ccccc12] | 1'-(2-(isobutoxyethyl)-3,4-dihydro-2H-spiro[isoquinoline-1,4'-piperidine] (*) (**) | F | 3.87 | 303.2 |
| 2AF | 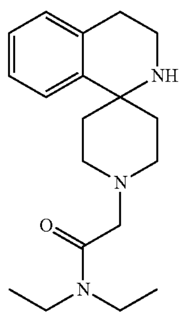 [SMILES: CCN(CC)C(=O)CN1CCC2(CC1)NCCc1ccccc12] | 2-(3,4-dihydro-2H-spiro[isoquinoline-1,4'-piperidine]-1'-yl)-N,N-diethyl-acetamide (*) | F | 3.39 | 316.2 |
| 2AG | 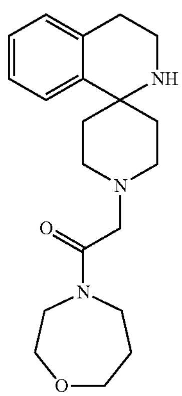 [SMILES: O=C(CN1CCC2(CC1)NCCc1ccccc12)N1CCCOCC1] | 2-(3,4-dihydro-2H-spiro[isoquinoline-1,4'-piperidine]-1'-yl)-1-(1,4-oxazepan-4-yl)ethanone (*) | F | 2.94 | 344.2 |
| 2AH | 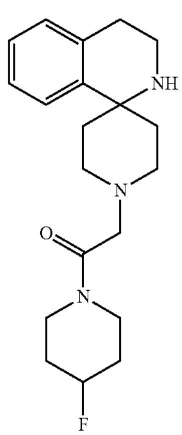 [SMILES: O=C(CN1CCC2(CC1)NCCc1ccccc12)N1CCC(F)CC1] | 2-(3,4-dihydro-2H-spiro[isoquinoline-1,4'-piperidine]-1'-yl)-1-(4-fluoropiperidin-1-yl)ethanone (*) | F | 3.39 | 346.2 |

-continued

| INT | Structure | Chemical name | Method | Ret (min) | MS (M + H) |
|---|---|---|---|---|---|
| 2AI | 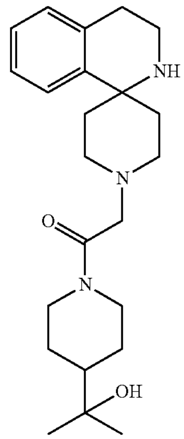 [SMILES: CC(C)(O)C1CCN(C(=O)CN2CCC3(CC2)NCCc2ccccc23)CC1] | 2-(3,4-dihydro-2H-spiro[isoquinoline-1,4'-piperidine]-1'-yl)-1-(4-(2-hydroxypropan-2-yl)piperidin-1-yl)ethanone (*) | F | 3.19 | 386.2 |
| 2AJ | 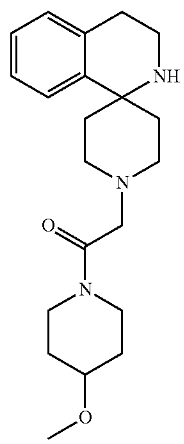 [SMILES: COC1CCN(C(=O)CN2CCC3(CC2)NCCc2ccccc23)CC1] | 2-(3,4-dihydro-2H-spiro[isoquinoline-1,4'-piperidine]-1'-yl)-1-(4-methoxypiperidin-1-yl)ethanone (*) | F | 3.24 | 358.2 |
| 2AK | 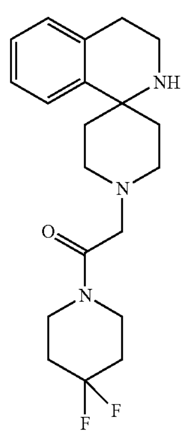 [SMILES: O=C(CN1CCC2(CC1)NCCc1ccccc12)N1CCC(F)(F)CC1] | 1-(4,4-difluoro-piperidin-1-yl)-2-(3,4-dihydro-2H-spiro[isoquinoline-1,4'-piperidine]-1'-yl)ethanone (*) | F | 3.69 | 364.2 |

-continued

| INT | Structure | Chemical name | Method | Ret (min) | MS (M + H) |
|---|---|---|---|---|---|
| 2AL | 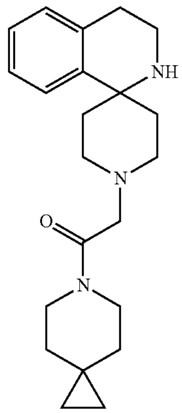 [SMILES: O=C(CN1CCC2(CC1)NCCc1ccccc12)N1CCC2(CC1)CC2] | 2-(3,4-dihydro-2H-spiro[isoquinoline-1,4'-piperidine]-1'-yl)-1-(6-azaspiro[2.5]octan-6-yl)ethanone (*) | F | 3.97 | 354.2 |
| 2AM | 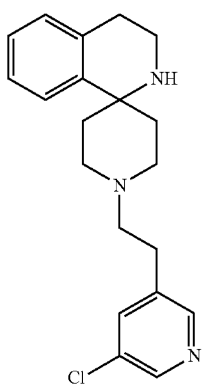 [SMILES: Clc1cncc(CCN2CCC3(CC2)NCCc2ccccc23)c1] | 1'-(2-(5-chloropyridin-3-yl)ethyl)-3,4-dihydro-2H-spiro[isoquinoline-1,4'-piperidine] (*) (**) | F | 3.67 | 342.2 |

(*) The reaction mixture was heated to reflux
(**) DIPEA was used as base instead of $K_2CO_3$.

Intermediate 2AN.

3-(3,4-Dihydro-2H-spiro[isoquinoline-1,4'-piperidine]-1'-yl)-N,N-dimethylpropanamide

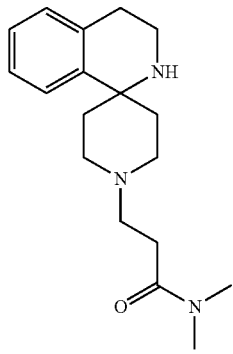 [SMILES: CN(C)C(=O)CCN1CCC2(CC1)NCCc1ccccc12]

A mixture of 3,4-dihydro-2H-spiro[isoquinoline-1,4'-piperidine] (obtained in the synthesis of intermediate 2W step a, 100 mg, 0.49 mmol) and N,N-dimethylacrylamide (0.08 mL, 0.75 mmol) in ethanol (1 mL) was heated at 95° C. in a sealed tube overnight. It was concentrated to dryness and the crude residue was purified by flash chromatography on $SiO_2$ (mobile phase: mixtures of MeOH/DCM of increasing polarity), to give the title compound (59 mg, yield 39%).

HPLC-MS (Method F): Ret, 2.55 min; ESI+-MS m/z, 302.1 (M+1).

A similar method was used for the preparation of intermediates 2AO-2AR using suitable starting materials and performing the reaction at 120° C. in 2-methoxyethanol instead of ethanol:

| INT | Structure | Chemical name | Method | Ret (min) | MS (M + H) |
|---|---|---|---|---|---|
| 2AO | 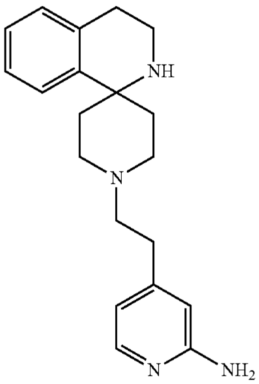 [SMILES: Nc1cc(CCN2CCC3(CC2)NCCc2ccccc23)ccn1] | 4-(2-(3,4-dihydro-2H-spiro[isoquinoline-1,4'-piperidine]-1'-yl)ethyl)pyridin-2-amine | F | 2.86 | 323.0 |
| 2AP | 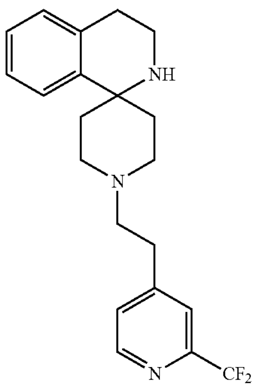 | 1'-(2-(2-(trifluoromethyl)pyridin-4-yl)ethyl)-3,4-dihydro-2H-spiro[isoquinoline-1,4'-piperidine] | F | 4.01 | 376.2 |
| 2AQ | 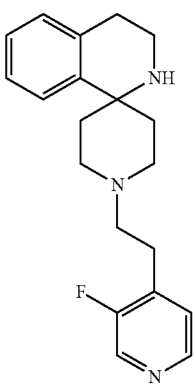 [SMILES: Fc1cnccc1CCN1CCC2(CC1)NCCc1ccccc12] | 1'-(2-(3-fluoropyridin-4-yl)ethyl)-3,4-dihydro-2H-spiro[isoquinoline-1,4'-piperidine] | F | 3.34 | 326.2 |
| 2AR | 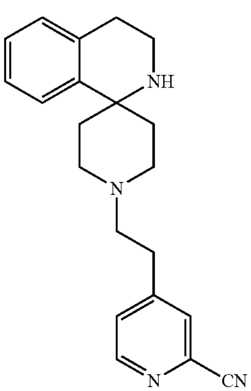 [SMILES: N#Cc1cc(CCN2CCC3(CC2)NCCc2ccccc23)ccn1] | 4-(2-(3,4-dihydro-2H-spiro[isoquinoline-1,4'-piperidine]-1'-yl)ethyl)picolinonitrile | F | 3.45 | 333.2 |

Intermediate 2AS.

3-[2-(3,4-Dihydro-2H-spiro[isoquinoline-1,4'-piperidin]-1'-yl)-ethyl]-phenylamine

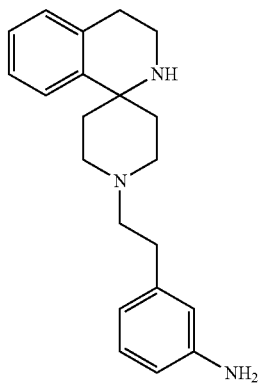

1'-(3-Nitrophenethyl)-3,4-dihydro-2H-spiro[isoquinoline-1,4'-piperidine] (intermediate 2Q 132 mg, 0.38 mmol) was added to a suspension of Pd/C (67 mg, 10% Pd w/w, 63% H$_2$O w/w, 0.04 mmol) in MeOH (10 mL) and the mixture was stirred at r.t. under H$_2$ atmosphere (balloon) for 1 h. The reaction mixture was filtered through Celite, rinsed with MeOH and concentrated. The crude residue was slurred with hexanes, filtered and eluted with hexanes. The solid collected was dried under high vacuum to furnish the title compound as a pale yellow solid (103 mg, yield 84%).

HPLC-MS (Method C): Ret, 12.80 min; ESI$^+$-MS m/z, 322.1 (M+1).

Intermediate 2AT.

2-(3,4-Dihydro-2H-spiro[isoquinoline-1,4'-piperidine]-1'-yl)ethanol

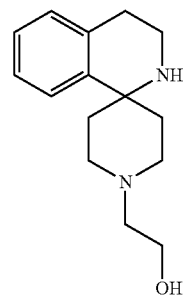 [SMILES: OCCN1CCC2(CC1)NCCc1ccccc12]

a) 1'-(2-((Tetrahydro-2H-pyran-2-yl)oxy)ethyl)-2H-spiro[isoquinoline-1,4'-piperidin]-3(4H)-one 2-(2-Bromoethoxy)tetrahydro-2H-pyran (464 mg, 2.22 mmol) was added to a suspension of 2H-spiro[isoquinoline-1,4'-piperidine]-3(4H)-one (obtained in the synthesis of intermediate 1 D step a, 400 mg, 1.85 mmol) and K$_2$CO$_3$ (767 mg, 5.55 mmol) in ACN (10 mL). The reaction mixture was refluxed overnight. It was cooled down to r.t., diluted with water and extracted with EtOAc. The combined organic layers were washed with brine, dried over MgSO$_4$, filtered and concentrated. The crude residue was purified by flash chromatography on SiO$_2$ (mobile phase: MeOH/DCM mixtures of increasing polarity) to give 1'-(2-((tetrahydro-2H-pyran-2-yl)oxy)ethyl)-2H-spiro[isoquinoline-1,4'-piperidin]-3(4H)-one (300 mg, yield 47%).

HPLC-MS (Method F): Ret, 3.11 min; ESI+-MS m/z, 345.2 (M+1).

b) 2-(3,4-Dihydro-2H-spiro[isoquinoline-1,4'-piperidine]-1'-yl)ethanol

A solution of BH$_3$.SMe$_2$ in toluene (10 M, 0.26 mL, 2.57 mmol) was added to a solution of the compound obtained in step a (295 mg, 0.86 mmol) in dry toluene (5 mL) and the reaction mixture was refluxed overnight. It was cooled down to r.t., MeOH (5 mL) was added and the suspension was concentrated to dryness. MeOH (6 mL) and N,N'-dimethylethylenediamine (0.46 mL, 4.2 mmol) were added and the mixture was stirred for 5 h at reflux temperature. After cooling down to r.t., it was diluted with water and DCM, the phases were separated and the combined organic layers were dried over MgSO$_4$, filtered and concentrated to give the title compound (210 mg, quantitative yield).

HPLC-MS (Method F): Ret, 2.21 min; ESI$^+$-MS m/z, 247.1 (M+1).

Intermediate 2AU.

1'-Phenethyl-3,4-dihydro-2H-spiro[isoquinoline-1,4'-piperidin]-6-ol

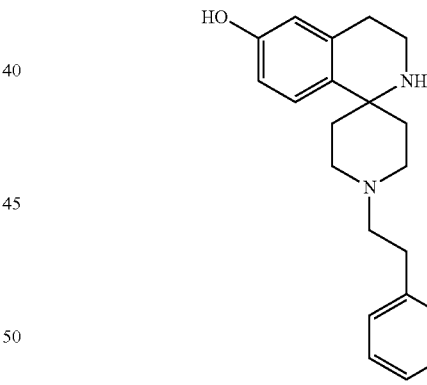

HBr (8.8 mL, 33% AcOH solution, 155 mmol) was added to a solution of 6-methoxy-1'-phenethyl-3,4-dihydro-2H-spiro[isoquinoline-1,4'-piperidine] (intermediate 2A, 1.6 g, 5 mmol) in AcOH (30 mL) and the reaction mixture was subjected to microwave irradiating conditions for 30 min at 150° C. The mixture was allowed to coil to r.t and the solvent was evaporated under vacuum. The residue thus obtained was neutralized with NaHCO$_3$ and extracted with ethyl acetate. The combined organic layers were dried over Na$_2$SO$_4$, filtered and evaporated under vacuum to yield the title compound (1.65 g, quantitative yield).

HPLC-MS (Method H): Ret, 1.51 min; ESI$^+$-MS m/z, 323.2 (M+1).

Intermediate 2AV.

2-(3,4-dihydro-2H-spiro[isoquinoline-1,4'-piperidine]-1'-yl)-N-ethyl-N-isopropylacetamide

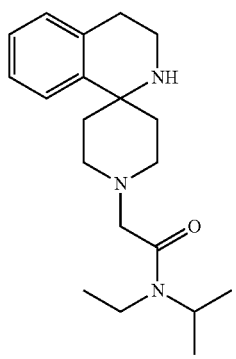 [SMILES: CCN(C(=O)CN1CCC2(CC1)NCCc1ccccc12)C(C)C]

Following a similar procedure to that described in the synthesis of intermediate 2X, the title intermediate was obtained as an oil (yield 16%).

HPLC-MS (Method H): Ret, 1.73 min; ESI$^+$-MS m/z, 330.3 (M+1).

Intermediate 2AW.

2-(3,4-dihydro-2H-spiro[isoquinoline-1,4'-piperidine]-1'-yl)-1-(pyridin-4-yl)ethanol

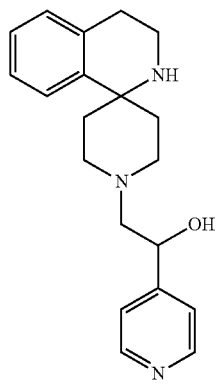 [SMILES: OC(CN1CCC2(CC1)NCCc1ccccc12)c1ccncc1]

A solution of 3,4-dihydro-2H-spiro[isoquinoline-1,4'-piperidine] (obtained in the synthesis of intermediate 2W step a, 144 mg, 0.7 mmol) and 4-(oxiran-2-yl)pyridine (86 mg, 0.7 mmol) in EtOH was stirred at r.t overnight. Then, the solvent was evaporated under reduced pressure and the crude directly absorbed onto silica gel and purified by flash chromatography (mobile phase: DCM/MeOH), to give the title compound (38 mg, yield 16%).

HPLC-MS (Method H): Ret, 1.30 min; ESI$^+$-MS m/z, 325.3 (M+1).

Intermediate 3A.

1-(1'-benzyl-3,4-dihydro-2H-spiro[isoquinoline-1,4'-piperidin]-2-yl)-2-methoxyethanone

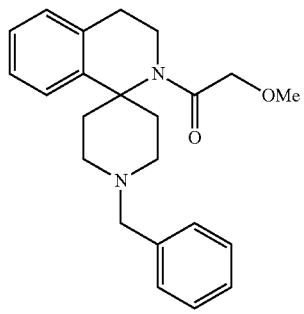 [SMILES: COCC(=O)N1CCc2ccccc2C12CCN(Cc1ccccc1)CC2]

To a solution of 1'-(benzyl)-3,4-dihydro-2H-spiro[isoquinoline-1,4'-piperidine (intermediate 2B, 600 mg, 2.06 mmol) in DCM (12 mL), methoxyacetyl chloride (1.34 g, 12.35 mmol) and pyridine (1.5 mL, 18.6 mmol) were added. The reaction mixture was refluxed for 24 h. Water was added and the mixture was twice extracted with DCM The combined organic layers were washed with 1 N NaOH, dried over Na$_2$SO$_4$, filtered and concentrated. The crude residue was purified by flash chromatography on silica-gel (mobile phase: DCM/MeOH), to give the title compound as an orange oil (609 mg, yield 81%).

HPLC-MS (Method F): Ret, 4.08 min; ESI$^+$-MS m/z, 365.2 (M+1).

A similar method was used for the preparation of intermediate 3B using suitable starting materials:

| INT | Structure | Chemical name | Method | Ret (min) | MS (M + H) |
|---|---|---|---|---|---|
| 3B | 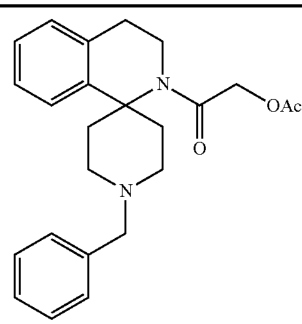 | 2-(1'-benzyl-3,4-dihydro-2H-spiro[isoquinoline-1,4'-piperidine]-2-yl)-2-oxoethyl acetate | F | 4.07 | 393.2 |

Intermediate 3C.

1'-Benzyl-2-methyl-3,4-dihydro-2H-spiro[isoquinoline-1,4'-piperidine]

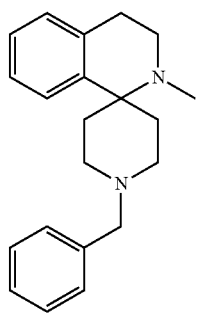 [SMILES: CN1CCc2ccccc2C12CCN(Cc1ccccc1)CC2]

Formaldehyde (37% aqueous solution, 4.3 mL, 56.90 mmol) was added to a solution of 1'-benzyl-3,4-dihydro-2H-spiro[isoquinoline-1,4'-piperidine] (intermediate 2B, 1.04 g, 3.22 mmol) in MeOH (25 mL). The reaction mixture was stirred at r.t. for 22 h, NaBH(OAc)$_3$ (1.88 g, 8.89 mmol) was added and the mixture was stirred at r.t. for 24 h. The reaction mixture was slowly poured into NaHCO$_3$ saturated aqueous solution, the solvent was concentrated off and the residue was diluted with DCM. The organic layer was washed with NaHCO$_3$ saturated aqueous solution, NaCl saturated aqueous solution and H$_2$O, dried over Na$_2$SO$_4$, filtered and concentrated. The resulting oil was purified by flash chromatography on SiO$_2$ (15→50% acetone/hexanes), to afford the title compound as a white solid (810 mg, yield 74%).

HPLC-MS (Method B): Ret, 16.55 min ESI$^+$-MS; m/z, 307.0 (M+1)

Intermediate 3D.

1'-Benzyl-2-(2-methoxyethyl)-3,4-dihydro-2H-spiro[isoquinoline-1,4'-piperidine]

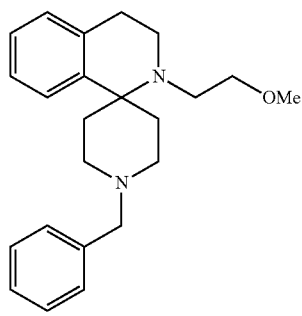 [SMILES: COCCN1CCc2ccccc2C12CCN(Cc1ccccc1)CC2]

BH$_3$.SMe$_2$ solution (10 M, 125 µL, 1.25 mmol) was added to solution of 1-(1'-benzyl-3,4-dihydro-2H-spiro[isoquinoline-1,4'-piperidin]-2-yl)-2-methoxyethanone (intermediate 3A, 302 mg, 0.828 mmol) in toluene (15 mL). The reaction mixture was warmed up to reflux and stirred at this temperature for 1 h. It was cooled down to r.t., HCl (10% aqueous solution, 1 mL) was added and the suspension was stirred at r.t. for 10 min. MeOH (5 mL) was added, the mixture was warmed up to reflux and stirred at this temperature for 40 min. It was cooled down to r.t., poured into NaOH (10% aqueous solution, 10 mL) and extracted with DCM (3×20 mL). The combined organic layers were dried over Na$_2$SO$_4$ (anhydrous), filtered and concentrated, to give the title compound as a yellow oil (234 mg, yield 81%).

HPLC-MS (Method E): Ret, 9.72 min; ESI$^+$-MS m/z, 351.1 (M+1).

Intermediate 3E.

2-(1'-Benzyl-3,4-dihydro-2H-spiro[isoquinoline-1,4'-piperidine]-2-yl)ethanol

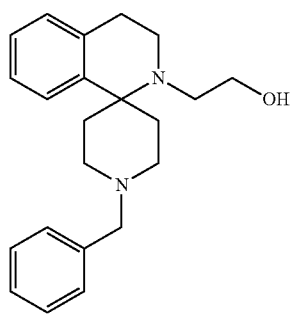 [SMILES: OCCN1CCc2ccccc2C12CCN(Cc1ccccc1)CC2]

A solution of BH$_3$.THF in THF (1 M, 12 mL, 12 mmol) was added to a solution of 2-(1'-benzyl-3,4-dihydro-2H-spiro[isoquinoline-1,4'-piperidin]-2-yl)-2-oxoethyl acetate (intermediate 3B, 0.2 g, 0.52 mmol) in THF (20 mL) and the reaction mixture was refluxed for 18 h. It was cooled down to r.t., 1 M HCl solution and methanol were added, and the mixture was refluxed for 1 h. After cooling down to r.t., the mixture was adjusted to pH 9-10 with 1N NaOH and extracted with DCM. The combined organic layers were dried over MgSO$_4$, filtered and concentrated. The crude residue was purified by flash chromatography on SiO$_2$ (mobile phase: MeOH/DCM mixtures of increasing polarity) to give the title compound (0.85 g, yield 81%).

HPLC-MS (Method F): Ret, 3.78 min; ESI$^+$-MS m/z, 337.2 (M+1).

Intermediate 3F.

1',2-Dibenzyl-3,4-dihydro-2H-spiro[isoquinoline-1,4'-piperidine

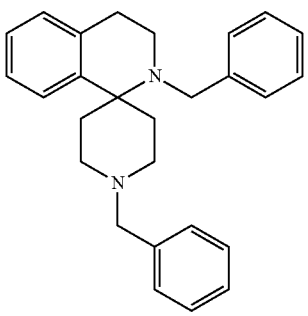 [SMILES: c1ccc(CN2CCC3(CC2)c2ccccc2CCN3Cc2ccccc2)cc1]

Benzyl bromide (41 µL, 0.34 mmol) was added to a solution of 1'-benzyl-3,4-dihydro-2H-spiro[isoquinoline-1,4'-piperidine] (intermediate 2B, 100 mg, 0.34 mmol), and K$_2$CO$_3$ (94.5 mg, 0.68 mmol) in ACN (50 mL) and the reaction mixture was heated at 50° C. for 48 h. After cooling back to r.t., the solvent was evaporated under reduced pressure and the crude directly absorbed onto silica gel with the aid of ethyl acetate. The crude residue was purified by flash chromatography on SiO$_2$, (Cyclohexane/AcOEt, 90:10). Further purification by semipreparative reverse phase HPLC gave the title compound (51.5 mg, 39.4% yield). HPLC-MS (Method H): Ret, 1.98 min; ESI$^+$-MS m/z, 383 (M+1).

Intermediate 3G.

1-(1'-benzyl-3,4-dihydro-2H-spiro[isoquinoline-1,4'-piperidine]-2-yl)-2,2,2-trifluoroethanone

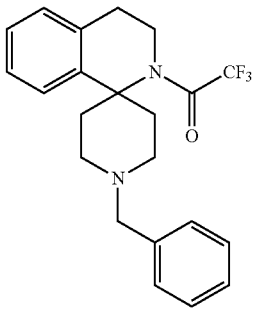 [SMILES: O=C(N1CCc2ccccc2C12CCN(Cc1ccccc1)CC2)C(F)(F)F]

To a solution of 1'-(benzyl)-3,4-dihydro-2H-spiro[isoquinoline-1,4'-piperidine (intermediate 2B, 400 mg, 1.37 mmol) in DCM (20 mL), trifluoroacetic anhydride (2.87 g, 13.7 mmol) and pyridine (1.1 mL, 13.7 mmol) were added. The reaction mixture was refluxed for 24 h. A saturated solution of NaHCO$_3$ was added, and the reaction mixture was extracted with DCM. The combined organic layers were dried over MgSO$_4$, filtered and evaporated under vacuum to give the title compound 378 mg, 71% yield).

HPLC-MS (Method F): Ret, 5.33 min; ESI$^+$-MS m/z, 389.1 (M+1).

Intermediate 3H.

1'-benzyl-2-(2,2,2-trifluoroethyl)-3,4-dihydro-2H-spiro[isoquinoline-1,4'-piperidine]

Following a similar procedure to that described for Intermediate 3D, but starting from intermediate 3G the title compound was obtained.

HPLC-MS (Method F): Ret, 5.52 min; ESI$^+$-MS m/z, 375.2 (M+1).

Intermediate 3I.

1'-Benzyl-4,4-dimethyl-2H-spiro[isoquinoline-1,4'-piperidin]-3(4H)-one

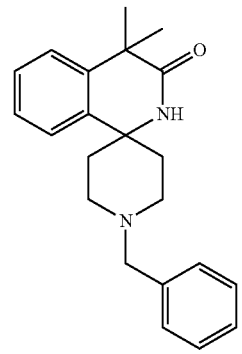 [SMILES: CC1(C)C(=O)NC2(CCN(Cc3ccccc3)CC2)c2ccccc21]

NaH (60% dispersion in mineral iol, 78 mg, 1.9 mmol) was added to a solution of 1'-benzyl-2H-spiro[isoquinoline-1,4'-piperidin]-3(4H)-one (intermediate 1A, 0.3 g, 0.98 mmol) in DMF (3 mL). The mixture was stirred at r.t for 30 min and then iodomethane (60 mL, 0.98 mmol) was added, and the reaction mixture was stirred at r.t overnight. A saturated solution of NaHCO$_3$ was added, and it was extracted with ethyl acetate. The combined organic layers were dried over MgSO$_4$, filtered and evaporated. The residue was purified by flash chromatography on C$_{18}$ (mobile phase: gradient aqueous NH$_4$HCO$_3$ to ACN) to give the title compound (102 mg, 31% yield).

HPLC-MS (Method F): Ret, 4.17 min; ESI$^+$-MS m/z, 335.2 (M+1).

Intermediate 3J.

1'-Benzyl-4,4-dimethyl-3,4-dihydro-2H-spiro[isoquinoline-1,4'-piperidine]

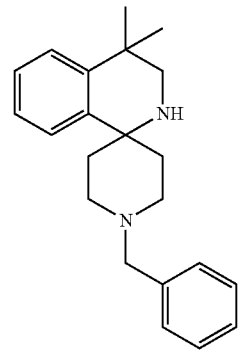 [SMILES: CC1(C)CNC2(CCN(Cc3ccccc3)CC2)c2ccccc21]

Following a similar procedure to that described in the synthesis of intermediate 2B, but starting from intermediate 3I (240 mg, 0.71 mmol), the title compound was obtained (212 mg, 66% yield).

HPLC-MS (Method F): Ret, 4.96 min; ESI$^+$-MS m/z, 321.1 (M+1).

Intermediate 3K.

1'-Benzyl-2,4,4-trimethyl-3,4-dihydro-2H-spiro[isoquinoline-1,4'-piperidine]

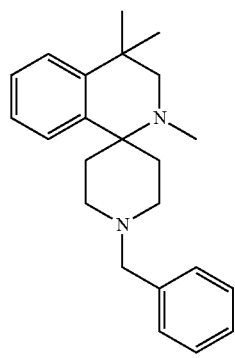 [SMILES: CN1CC(C)(C)c2ccccc2C12CCN(Cc1ccccc1)CC2]

Following a similar procedure to that described in the synthesis of intermediate 3C but starting from intermediate 3J (202 mg, 0.63 mmol), the title compound was obtained (147 mg, 70% yield).

HPLC-MS (Method F): Ret, 5.53 min; ESI$^+$-MS m/z, 335.2 (M+1).

Intermediate 3L.

1'-Benzyl-2-ethyl-3,4-dihydro-2H-spiro[isoquinoline-1,4'-piperidine]

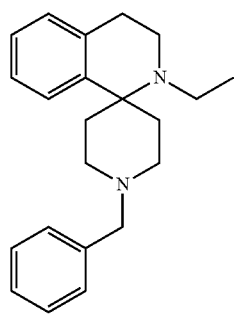 [SMILES: CCN1CCc2ccccc2C12CCN(Cc1ccccc1)CC2]

Following a similar procedure to that described in the synthesis of intermediate 3C, but using acetaldehyde as reactant, the title intermediate was obtained as an oil (yield 43%).

HPLC-MS (Method H): Ret, 2.43 min; ESI$^+$-MS m/z, 321 (M+1).

Intermediate 4A.

1'-Benzylspiro[isoindoline-1,4'-piperidin]-3-one

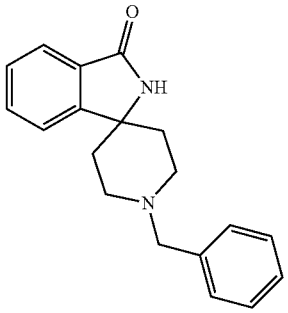 [SMILES: O=C1NC2(CCN(Cc3ccccc3)CC2)c2ccccc21]

a) 2-Iodo-N-(4-methoxybenzyl)-N-(1-Boc-1,2,3,6-tetrahydropyridin-4-yl)benzamide 1-Boc-piperidin-4-one (10.04 g, 50.39 mmol) was added to a solution of 1-(4-methoxyphenyl)methanamine (6.91 g, 50.39 mmol) in toluene (120 mL). The reaction was refluxed (Dean-Stark) for 20.5 h, allowed to reach r.t. and concentrated, to give the imine intermediate as a yellow oil. This imine was used in the next step without further purification.

Freshly prepared 2-iodobenzoyl chloride (40.31 mmol) in toluene (160 mL) was slowly added to a solution of imine intermediate (50.39 mmol) and Et$_3$N (13.5 mL, 96.74 mmol) in toluene (60 mL). The reaction mixture was warmed up to 80° C. and stirred at this temperature for 20 h. The resulting solution was allowed to reach r.t., solvent was concentrated, the crude residue was dissolved in EtOAc (200 mL), washed with NaCl (saturated aqueous solution, 2×250 mL) and H$_2$O (1×250 mL). The organic layer was dried over Na$_2$SO$_4$, filtered and concentrated. The crude residue was purified by flash chromatography on SiO$_2$ (30% acetone/hexanes), to give the title compound as a yellow solid (17 g, yield 55%).

HPLC-MS (Method B1): Ret, 10.46 min; ESI$^+$-MS m/z, 549.1 (M+1).

b) 1'-Boc-2-(4-methoxybenzyl)-2',3'-dihydro-1'H-spiro[isoindole-1,4'-pyridin]-3(2H)-one Pd(OAc)$_2$ (1.92 g, 2.85 mmol) was added to a suspension of the compound obtained in step a (15.64 g, 20.34 mmol), PPh$_3$ (1.49 g, 5.70 mmol), K$_2$CO$_3$ (7.88 g, 57.02 mmol) and TBACl (7.92 g, 28.51 mmol) in ACN (200 mL). The reaction mixture was warmed up to reflux and allowed to react for 24 h. It was cooled down to r.t., filtered through Celite, washed with EtOAc (300 mL), and concentrated. The residue was diluted with H$_2$O (250 mL) and extracted with EtOAc (2×200 mL). The combined organic layers were dried over Na$_2$SO$_4$, filtered and concentrated. The crude residue was purified by flash chromatography on SiO$_2$ (20% acetone/hexanes and 15% acetone/hexanes), to give the title compound as a yellow solid (9.0 g, yield 97%).

HPLC-MS (Method B1): Ret, 10.37 min; ESI$^+$-MS m/z, 221.2 (M+1).

c) 2',3'-Dihydro-1'H-spiro[isoindole-1,4'-pyridin]-3(2H)-one

A suspension of the compound obtained in step b (2.15 g, 4.73 mmol) in TFA (30 mL) was warmed up to reflux and stirred at this temperature for 3 days in a sealed tube. The reaction mixture was allowed to reach r.t. and the solvent was concentrated off.

The crude residue was diluted with H$_2$O (30 mL), taken up to pH 10 with NaOH (10% aqueous solution) and extracted with DCM (5×50 mL). The combined organic layers were dried over Na$_2$SO$_4$, filtered and concentrated. The crude residue was purified by flash chromatography on SiO$_2$ (MeOH/H$_2$O), to give the title compound as an off-white solid (335 mg, yield 35%).

HPLC-MS (Method A): Ret, 5.85 min; ESI$^+$-MS m/z, 201.2 (M+1).

d) Spiro[isoindole-1,4'-piperidin]-3(2H)-one

NaBH(OAc)$_3$ (856 mg, 4.05 mmol) was added to a 0° C. cooled suspension of the compound obtained in step c (326 mg, 1.62 mmol) and AcOH (5 mL) in ACN (5 mL).

The reaction mixture was allowed to reach r.t., stirred at this temperature for 3 h and slowly poured into NaHCO$_3$ (saturated aqueous solution, 20 mL). The mixture was taken up to pH 8-9 with NaOH (36% aqueous solution) and extracted with DCM (5×20 mL) and n-BuOH (2×15 mL). The combined organic layers were dried over Na$_2$SO$_4$, filtered and concentrated, to give the title compound as an off-white solid (360 mg, quantitative yield). The crude residue was submitted to next step without purification.

HPLC-MS (Method B1): Ret, 5.61 min; ESI$^+$-MS m/z, 203.1 (M+1).

e) Title Compound

Following a similar procedure to that described in the synthesis of intermediate 3C, but starting from the compound obtained in step d, and using benzaldehyde instead of formaldehyde, the title compound was obtained as a white solid (1.0 g, yield 62%).

HPLC-MS (Method B): Ret, 15.46 min; ESI$^+$-MS m/z, 293.1 (M+1).

Intermediate 4B.

1'-Benzyl-2-methylspiro[isoindoline-1,4'-piperidine]

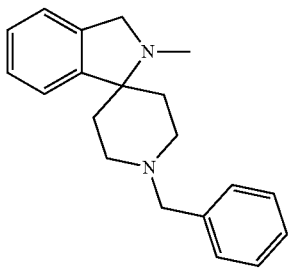 [SMILES: CN1Cc2ccccc2C12CCN(Cc1ccccc1)CC2]

a) 1'-Benzylspiro[isoindole-1,4'-piperidine

Following a similar procedure to that described in the synthesis of intermediate 2B, but starting from intermediate 4A, the title compound was obtained as an off-white oil (190 mg, yield 56%).

HPLC-MS (Method D): Ret, 15.63 min; ESI$^+$-MS m/z, 279.2 (M+1).

b) Title Compound

Following a similar procedure to that described in the synthesis of intermediate 3C, but starting from the compound obtained in step a, the title compound was obtained as an off-white solid (yield 90%).

HPLC-MS (Method B): Ret, 16.92 min; ESI$^+$-MS m/z, 293.2 (M+1).

Intermediate 4C.

2-Methyl-1'-phenethylspiro[isoindoline-1,4'-piperidin]-3-one

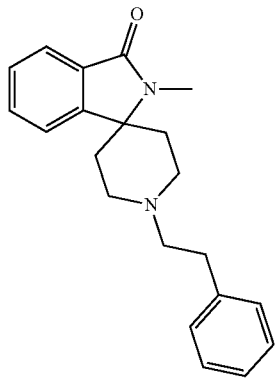 [SMILES: CN1C(=O)c2ccccc2C12CCN(CCc1ccccc1)CC2]

a) 1'-(2-Phenylethyl)spiro[isoindole-1,4'-piperidin]-3(2H)-one

Following a similar procedure to that described in the synthesis of intermediate 4A steps a and b, but starting from 1-(2-phenylethyl)piperidin-4-one instead of 1-boc-piperidin-4-one, the title compound was obtained as a yellow solid (yield 15% in four steps).

HPLC-MS (Method B1): Ret, 8.68 min; ESI$^+$-MS m/z, 306.9 (M+1).

b) Title compound.

NaH (60% mineral oil suspension, 22 mg, 0.561 mmol) was added to a 0 ° C. cooled solution of the compound obtained in step a (86 mg, 0.281 mmol) in THF (5 mL). The reaction mixture was allowed to reach r.t., stirred at this temperature for 10 min and MeI (22 μL, 0.351 mmol) was added. The reaction mixture was stirred at r.t. until full conversion was achieved (3 h). The mixture was poured into H$_2$O (5 mL) and extracted with EtOAc (4×10 mL). The combined organic layers were dried over Na$_2$SO$_4$ (anhydrous), filtered and concentrated. The crude residue (100 mg) was purified by flash chromatography on SiO$_2$ (5.5% MeOH/DCM) to give an oil, which was slurred with hexanes (2 mL), to afford the title compound as an off-white solid (25 mg, yield 28%).

HPLC-MS (Method B): Ret, 17.32 min; ESI$^+$-MS m/z, 321.3 (M+1).

SYNTHESIS OF EXAMPLES

Example 1.

2-Methyl-1-(1'-phenethyl-3,4-dihydro-2H-spiro[isoquinoline-1,4'-piperidine]-2-yl)ethan-1-one

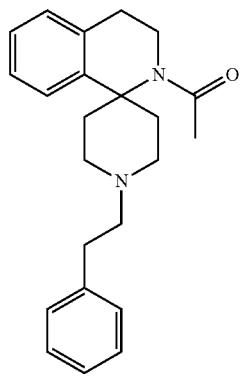

Acetyl chloride (91 mL, 1.27 mmol) was added to a solution of 1'-(2-phenylethyl)-3,4-dihydro-2H-spiro[isoquinoline-1,4'-piperidine (intermediate 2C, 300 mg, 0.98 mmol) and K2CO3 (405 mg, 2.93 mmol) in ACN (15 mL). The reaction was stirred at room temperature until full conversion was achieved (2.5 h). Water was added and the mixture was extracted with EtOAc (2×20 mL). The combined organic layers were dried over $Na_2SO_4$, filtered and concentrated. The crude residue was purified by flash chromatography on silica-gel (3% MeOH/DCM), to give the title compound as a white solid (283 mg, yield 83%).

HPLC-MS (Method D): Ret, 16.83 min; $ESI^+$-MS m/z, 349.0 (M+1).

Example 2.

2-Methyl-1-(1'-phenethyl-3,4-dihydro-2H-spiro[isoquinoline-1,4'-piperidine]-2-yl)propan-1-one

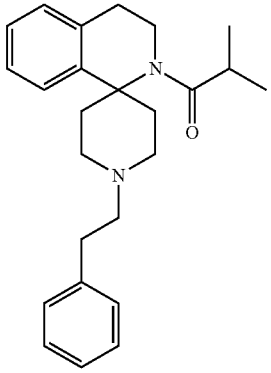 [SMILES: CC(C)C(=O)N1CCc2ccccc2C12CCN(CCc1ccccc1)CC2]

Following a similar procedure to that used in example 1, but using isobutyryl chloride instead of acetyl chloride the title compound was obtained as an oil (yield 77%).

HPLC-MS (Method B): Ret, 17.61 min; $ESI^+$-MS m/z, 377.2 (M+1).

This method was used for the preparation of examples 3-7 using suitable starting materials:

| EX | Structure | Chemical name | Method | Ret (min) | MS (M + H) |
|---|---|---|---|---|---|
| 3 | 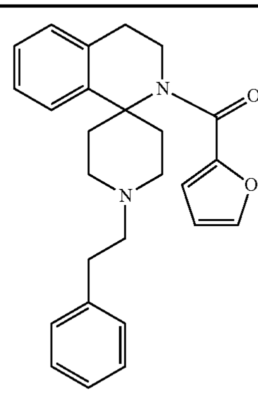 | furan-2-yl(1'-phenethyl-3,4-dihydro-2H-spiro[isoquinoline-1,4'-piperidine]-2-yl)methanone | B | 17.68 | 401.2 |
| 4 | 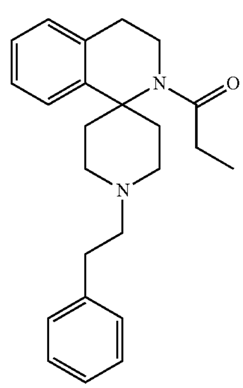 [SMILES: CCC(=O)N1CCc2ccccc2C12CCN(CCc1ccccc1)CC2] | 1-(1'-phenethyl-3,4-dihydro-2H-spiro[isoquinoline-1,4'-piperidine]-2-yl)propan-1-one | B | 16.18 | 363.2 |

-continued

| EX | Structure | Chemical name | Method | Ret (min) | MS (M + H) |
|----|-----------|---------------|--------|-----------|------------|
| 5 | 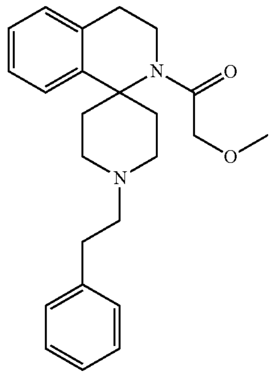 [SMILES: COCC(=O)N1CCc2ccccc2C12CCN(CCc1ccccc1)CC2] | 2-methoxy-1-(1'-phenethyl-3,4-dihydro-2H-spiro[isoquinoline-1,4'-piperidine]-2-yl)ethanone | B | 18.78 | 455.2 |
| 6 | 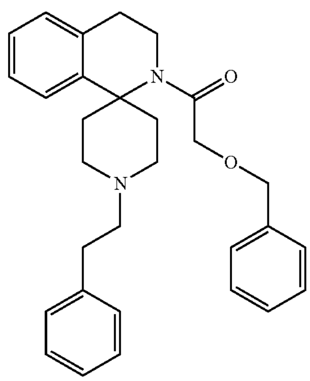 [SMILES: O=C(COCc1ccccc1)N1CCc2ccccc2C12CCN(CCc1ccccc1)CC2] | 2-(benzyloxy)-1-(1'-phenethyl-3,4-dihydro-2H-spiro[isoquinoline-1,4'-piperidine]-2-yl)ethanone | B | 15.08 | 379.2 |
| 7 | 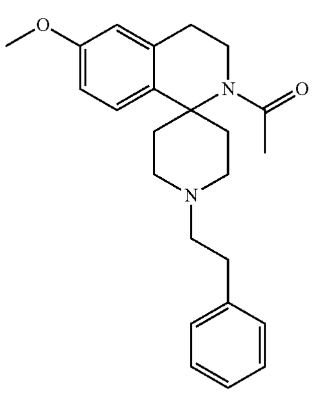 [SMILES: COc1ccc2c(c1)CCN(C(C)=O)C21CCN(CCc2ccccc2)CC1] | 1-(6-methoxy-1'-phenethyl-3,4-dihydro-2H-spiro[isoquinoline-1,4'-piperidine]-2-yl)ethanone | H | 1.79 | 379.3 |

Example 8.

1-[1'-(2-Morpholin-4-yl-ethyl)-3,4-dihydro-spiro[isoquinoline-1,4'-piperidin]-2-yl]-ethanone

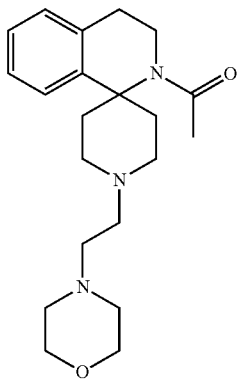 [SMILES: CC(=O)N1CCc2ccccc2C12CCN(CCN1CCOCC1)CC2]

Acetyl chloride (51 μL, 0.718 mmol) was added to a solution of 4-(2-(3,4-dihydro-2H-spiro[isoquinoline-1,4'-piperidin]-1'-yl)ethyl)morpholine (intermediate 2D, 0.598 mmol) and DIPEA (0.205 mL, 1.20 mmol) in DCM (3 mL). The reaction mixture was stirred at r.t. for 20 h, poured into H$_2$O and extracted with DCM. The combined organic layers were dried over Na$_2$SO$_4$, filtered and concentrated. The crude residue was purified by flash chromatography on silica-gel (8→10% MeOH/DCM), to give the title compound as a yellow oil (78 mg, yield 36%).

HPLC-MS (Method C): Ret, 10.71 min; ESI$^+$-MS m/z, 358.0 (M+1).

This method was used for the preparation of examples 9-31 starting from the corresponding examples.

| EX | Structure | Chemical name | Method | Ret time (min) | MS (M + H) |
|---|---|---|---|---|---|
| 9 | 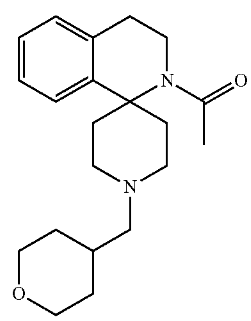 [SMILES: CC(=O)N1CCc2ccccc2C12CCN(CC1CCOCC1)CC2] | 1-(1'-((tetrahydro-2H-pyran-4-yl)methyl)-3,4-dihydro-2H-spiro[isoquinoline-1,4'-piperidine]-2-yl)ethanone | C | 11.64 | 343.1 |
| 10 | 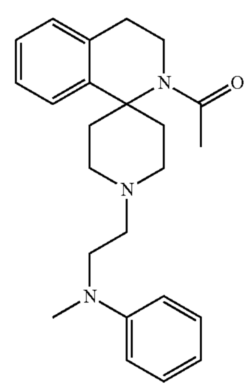 [SMILES: CC(=O)N1CCc2ccccc2C12CCN(CCN(C)c1ccccc1)CC2] | 1-(1'-(2-(methyl(phenyl)amino)ethyl)-3,4-dihydro-2H-spiro[isoquinoline-1,4'-piperidine]-2-yl)ethanone | C | 15.67 | 378.1 |
| 11 | 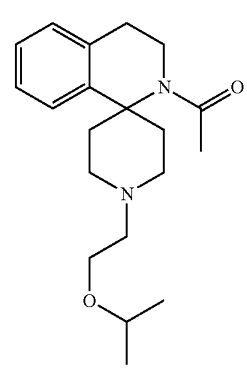 [SMILES: CC(=O)N1CCc2ccccc2C12CCN(CCOC(C)C)CC2] | 1-(1'-(2-isopropoxyethyl)-3,4-dihydro-2H-spiro[isoquinoline-1,4'-piperidine]-2-yl)ethanone | D | 15.76 | 331.2 |

-continued

| EX | Structure | Chemical name | Method | Ret time (min) | MS (M + H) |
|----|-----------|---------------|--------|----------------|------------|
| 12 | 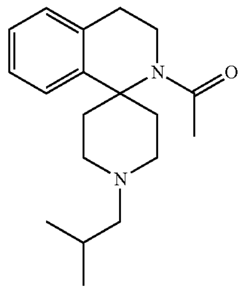 [SMILES: CC(=O)N1CCc2ccccc2C12CCN(CC(C)C)CC2] | 1-(1'-isobutyl-3,4-dihydro-2H-spiro[isoquinoline-1,4'-piperidine]-2-yl)ethanone | D | 14.41 | 301.2 |
| 13 | 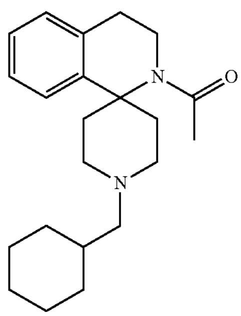 [SMILES: CC(=O)N1CCc2ccccc2C12CCN(CC1CCCCC1)CC2] | 1-(1'-(cyclohexylmethyl)-3,4-dihydro-2H-spiro[isoquinoline-1,4'-piperidine]-2-yl)ethanone | D | 16.64 | 341.2 |
| 14 | 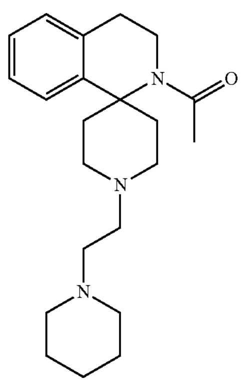 [SMILES: CC(=O)N1CCc2ccccc2C12CCN(CCN1CCCCC1)CC2] | 1-(1'-(2-(piperidin-1-yl)ethyl)-3,4-dihydro-2H-spiro[isoquinoline-1,4'-piperidine]-2-yl)ethanone | D | 13.91 | 356.1 |
| 15 | 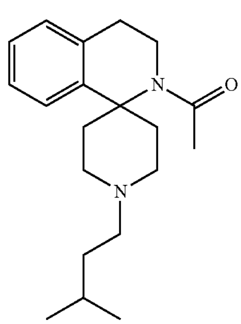 [SMILES: CC(=O)N1CCc2ccccc2C12CCN(CCC(C)C)CC2] | 1-(1'-isopentyl-3,4-dihydro-2H-spiro[isoquinoline-1,4'-piperidine]-2-yl)ethanone | D | 15.29 | 314.8 |

-continued

| EX | Structure | Chemical name | Method | Ret time (min) | MS (M + H) |
|----|-----------|---------------|--------|----------------|------------|
| 16 | 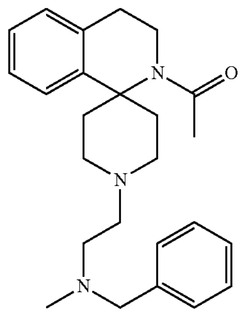 [SMILES: CC(=O)N1CCc2ccccc2C12CCN(CCN(C)Cc1ccccc1)CC2] | 1-(1'-(2-(benzyl(methyl)amino)ethyl)-3,4-dihydro-2H-spiro[isoquinoline-1,4'-piperidine]-2-yl)ethanone | D | 15.67 | 392.0 |
| 17 | 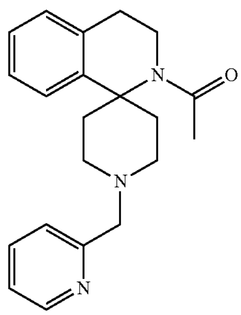 [SMILES: CC(=O)N1CCc2ccccc2C12CCN(Cc1ccccn1)CC2] | 1-(1'-(pyridin-2-ylmethyl)-3,4-dihydro-2H-spiro[isoquinoline-1,4'-piperidine]-2-yl)ethanone | D | 13.73 | 336.1 |
| 18 | 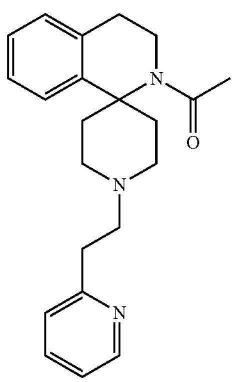 [SMILES: CC(=O)N1CCc2ccccc2C12CCN(CCc1ccccn1)CC2] | 1-(1'-(2-(pyridin-2-yl)ethyl)-3,4-dihydro-2H-spiro[isoquinoline-1,4'-piperidine]-2-yl)ethanone | D | 13.57 | 350.0 |
| 19 | 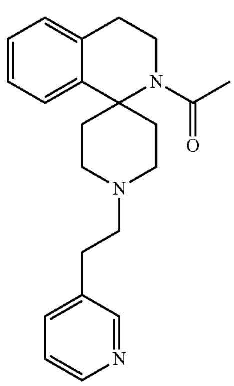 [SMILES: CC(=O)N1CCc2ccccc2C12CCN(CCc1cccnc1)CC2] | 1-(1'-(2-(pyridin-3-yl)ethyl)-3,4-dihydro-2H-spiro[isoquinoline-1,4'-piperidine]-2-yl)ethanone | D | 13.63 | 350.0 |

-continued

| EX | Structure | Chemical name | Method | Ret time (min) | MS (M + H) |
|---|---|---|---|---|---|
| 20 | 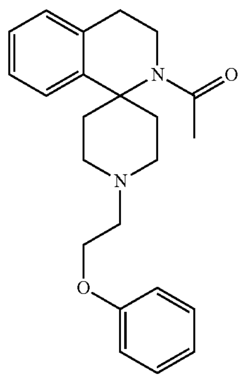 [SMILES: CC(=O)N1CCc2ccccc2C12CCN(CCOc1ccccc1)CC2] | 1-(1'-(2-phenoxyethyl)-3,4-dihydro-2H-spiro[isoquinoline-1,4'-piperidine]-2-yl)ethanone | C | 14.71 | 365.1 |
| 21 | 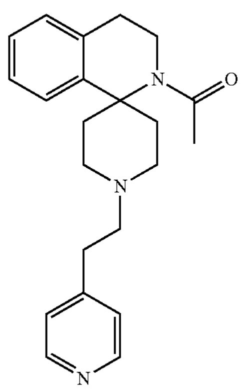 [SMILES: CC(=O)N1CCc2ccccc2C12CCN(CCc1ccncc1)CC2] | 1-(1'-(2-(pyridin-4-yl)ethyl)-3,4-dihydro-2H-spiro[isoquinoline-1,4'-piperidine]-2-yl)ethanone | D | 13.87 | 350.2 |
| 22 | 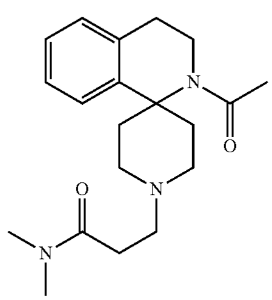 [SMILES: CC(=O)N1CCc2ccccc2C12CCN(CCC(=O)N(C)C)CC2] | 3-(2-acetyl-3,4-dihydro-2H-spiro[isoquinoline-1,4'-piperidine]-1'-yl)-N,N-dimethyl-propanamide | F | 2.67 | 344.2 |
| 23 | 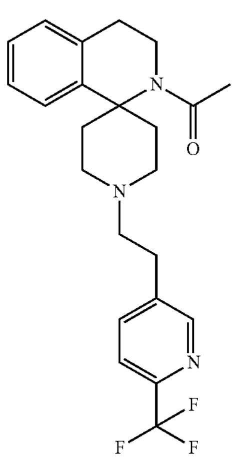 [SMILES: CC(=O)N1CCc2ccccc2C12CCN(CCc1ccc(C(F)(F)F)nc1)CC2] | 1-(1'-(2-(6-(trifluoromethyl)pyridin-3-yl)ethyl)-3,4-dihydro-2H-spiro[isoquinoline-1,4'-piperidine]-2-yl)ethanone | F | 4.08 | 418.0 |

-continued

| EX | Structure | Chemical name | Method | Ret time (min) | MS (M + H) |
|---|---|---|---|---|---|
| 24 | 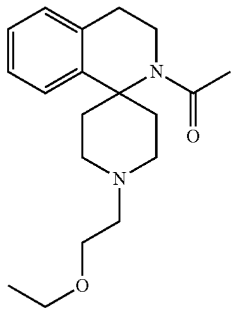 [SMILES: CCOCCN1CCC2(CC1)c1ccccc1CCN2C(C)=O] | 1-(1'-(2-ethoxyethyl)-3,4-dihydro-2H-spiro[isoquinoline-1,4'-piperidine]-2-yl)ethanone | F | 3.07 | 317.2 |
| 25 | 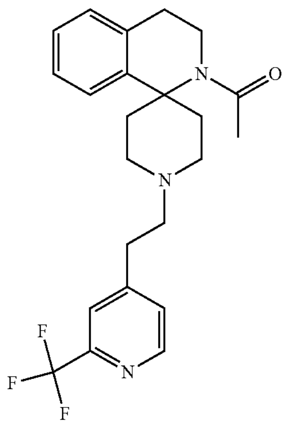 [SMILES: CC(=O)N1CCc2ccccc2C12CCN(CCc1ccnc(C(F)(F)F)c1)CC2] | 1-(1'-(2-(2-(trifluoromethyl)pyridin-4-yl)ethyl)-3,4-dihydro-2H-spiro[isoquinoline-1,4'-piperidine]-2-yl)ethanone | F | 4.05 | 418.2 |
| 26 | 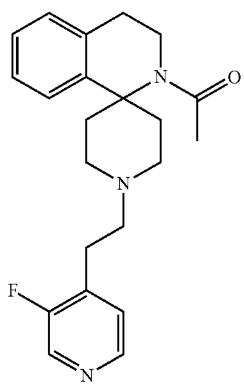 [SMILES: CC(=O)N1CCc2ccccc2C12CCN(CCc1ccncc1F)CC2] | 1-(1'-(2-(3-fluoropyridin-4-yl)ethyl)-3,4-dihydro-2H-spiro[isoquinoline-1,4'-piperidine]-2-yl)ethanone | F | 3.42 | 368.2 |
| 27 | 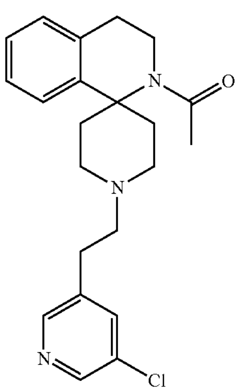 [SMILES: CC(=O)N1CCc2ccccc2C12CCN(CCc1cncc(Cl)c1)CC2] | 1-(1'-(2-(5-chloropyridin-3-yl)ethyl)-3,4-dihydro-2H-spiro[isoquinoline-1,4'-piperidine]-2-yl)ethanone | F | 3.74 | 384.2 |

| EX | Structure | Chemical name | Method | Ret time (min) | MS (M + H) |
|---|---|---|---|---|---|
| 28 | 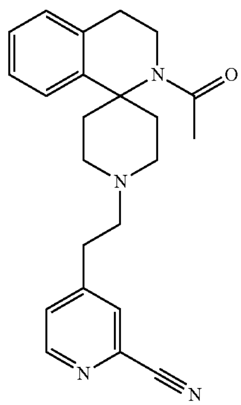 [SMILES: CC(=O)N1CCc2ccccc2C12CCN(CCc1ccnc(C#N)c1)CC2] | 4-(2-(2-acetyl-3,4-dihydro-2H-spiro[isoquinoline-1,4'-piperidine]-1'-yl)ethyl) picolinonitrile | F | 3.52 | 375.2 |
| 29 | 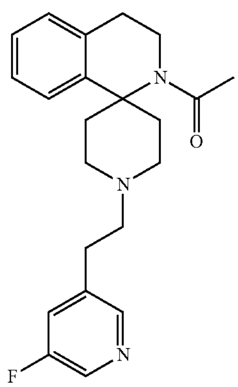 [SMILES: CC(=O)N1CCc2ccccc2C12CCN(CCc1cncc(F)c1)CC2] | 1-(1'-(2-(5-fluoropyridin-3-yl)ethyl)-3,4-dihydro-2H-spiro[isoquinoline-1,4'-piperidine]-2-yl)ethanone | F | 3.38 | 368.2 |
| 30 | 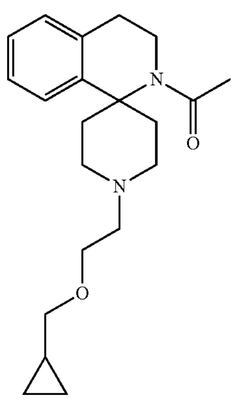 [SMILES: CC(=O)N1CCc2ccccc2C12CCN(CCOCC1CC1)CC2] | 1-(1'-(2-(cyclopropyl-methoxy)ethyl)-3,4-dihydro-2H-spiro[isoquinoline-1,4'-piperidine]-2-yl)ethanone | F | 3.37 | 343.2 |
| 31 | 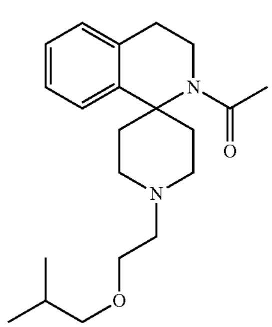 [SMILES: CC(=O)N1CCc2ccccc2C12CCN(CCOCC(C)C)CC2] | 1-(1'-(2-(isobutoxy-ethyl)-3,4-dihydro-2H-spiro[isoquinoline-1,4'-piperidine]-2-yl)ethanone | F | 3.91 | 345.2 |

Example 32

1-(1'-(2-(benzyloxy)ethyl)-3,4-dihydro-2H-spiro[isoquinoline-1,4'-piperidine]-2-yl)ethanone

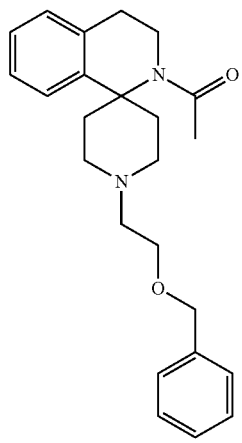 [SMILES: CC(=O)N1CCc2ccccc2C12CCN(CCOCc1ccccc1)CC2]

Ac₂O (39 μL, 4.1 mmol) was added to a solution of 1'-(2-(benzyloxy)ethyl)-3,4-dihydro-2H-spiro[isoquinoline-1,4'-piperidine] (intermediate 2R 140 mg, 0.41 mmol) and pyridine (33 μL, 4.1 mmol) in DCM (3 mL), and the reaction mixture was refluxed overnight. The mixture was poured into NaHCO₃ saturated aqueous solution and the aqueous layer was extracted with DCM. The combined organic layers were dried over MgSO₄, filtered and concentrated. The crude residue was purified by flash chromatography on SiO₂ (mobile phase: DCM/MeOH), to give the title compound (62 mg, yield 39%).

HPLC-MS (Method F): Ret, 3.86 min; ESI$^+$-MS m/z, 379.2 (M+1).

This method was used for the preparation of examples 33-37 starting from the corresponding examples.

| EX | Structure | Chemical name | Method | Ret time (min) | MS (M + H) |
|----|-----------|---------------|--------|----------------|------------|
| 33 | 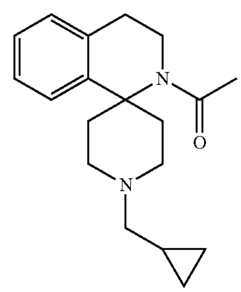 [SMILES: CC(=O)N1CCc2ccccc2C12CCN(CC1CC1)CC2] | 1-(1'-(Cyclopropyl-methyl)-3,4-dihydro-2H-spiro[isoquinoline-1,4'-piperidine]-2-yl)ethanone | F | 2.83 | 299.2 |
| 34 | 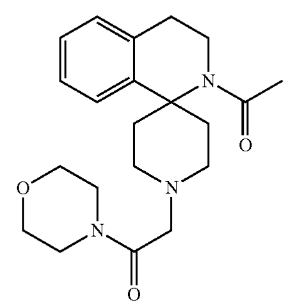 [SMILES: CC(=O)N1CCc2ccccc2C12CCN(CC(=O)N1CCOCC1)CC2] | 2-(2-acetyl-3,4-dihydro-2H-spiro[isoquinoline-1,4'-piperidine]-1'-yl)-1-morpholino-ethanone | F | 2.94 | 372.2 |
| 35 | 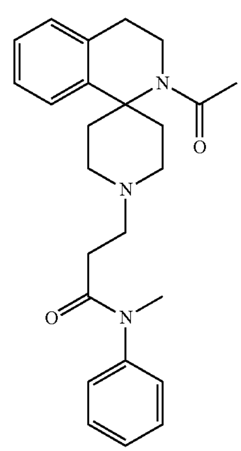 [SMILES: CC(=O)N1CCc2ccccc2C12CCN(CCC(=O)N(C)c1ccccc1)CC2] | 3-(2-acetyl-3,4-dihydro-2H-spiro[isoquinoline-1,4'-piperidine]-1'-yl)-N-methyl-N-phenyl-propanamide | F | 3.51 | 406.2 |

| EX | Structure | Chemical name | Method | Ret time (min) | MS (M + H) |
|---|---|---|---|---|---|
| 36 | 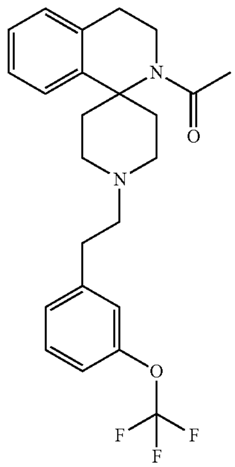 [SMILES: CC(=O)N1CCc2ccccc2C12CCN(CCc1cccc(OC(F)(F)F)c1)CC2] | 1-(1'-(3-(trifluoromethoxy)phenethyl)-3,4-dihydro-2H-spiro[isoquinoline-1,4'-piperidine]-2-yl)ethanone | F | 4.81 | 433.0 |
| 37 | 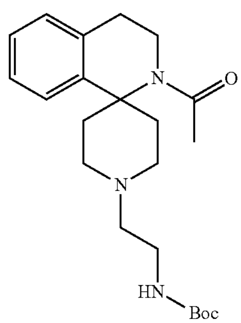 [SMILES: CC(=O)N1CCc2ccccc2C12CCN(CCNC(=O)OC(C)(C)C)CC2] | tert-butyl 2-(2-acetyl-3,4-dihydro-2H-spiro[isoquinoline-1,4'-piperidine]-1'-yl)ethylcarbamate | F | 3.70 | 388.2 |

Example 38

N-{3-[2-(2-Acetyl-3,4-dihydro-2H-spiro[isoquinoline-1,4'-piperidin]-1'-yl)-ethyl]-phenyl}-acetamide

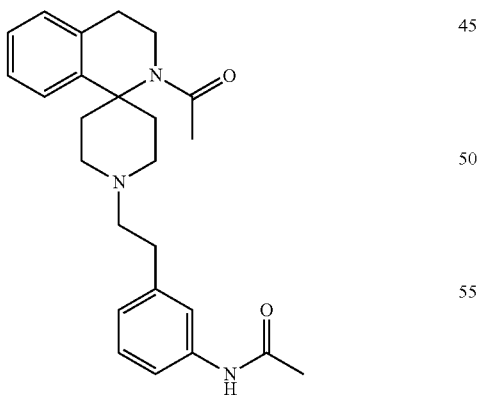

Acetyl chloride (113 mL, 1.58 mmol) was added to a solution of 3-[2-(3,4-dihydro-2H-spiro[isoquinoline-1,4'-piperidin]-1'-yl)-ethyl]-phenylamine (intermediate 2AS, 51 mg, 0.143 mmol) and DIPEA (82 mL, 0.48 mmol) in DCM (5 mL). The reaction mixture was stirred at r.t. for 5 days, poured into NaHCO₃ saturated aqueous solution (10 mL) and extracted with DCM. The combined organic layers were dried over Na₂SO₄, filtered and concentrated. The crude residue was purified by flash chromatography on SiO₂ (2→5% MeOH/DCM) and slurred with hexanes, to yield the title compound as a white solid (40 mg, yield 69%).

HPLC-MS (Method C): Ret, 12.67 min; ESI⁺-MS m/z, 406.1 (M+1).

Example 39

2-(2-Acetyl-3,4-dihydro-2H-spiro[isoquinoline-1,4'-piperidine]-1'-yl)-1-phenylethyl acetate

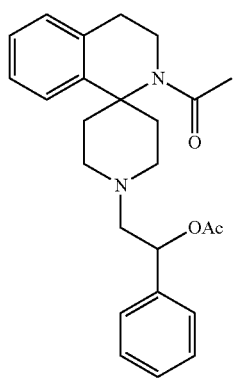 [SMILES: CC(=O)OC(CN1CCC2(CC1)c1ccccc1CCN2C(C)=O)c1ccccc1]

Following the procedure described in example 8, but using intermediate 2V as starting material and 2.2 equivalents of acetyl chloride, the title compound was obtained.

HPLC-MS (Method F): Ret, 4.22 min; ESI⁺-MS m/z, 407.1 (M+1).

Example 40

1-(1'-(2-Hydroxy-2-phenylethyl)-3,4-dihydro-2H-spiro[isoquinoline-1,4'-piperidine]-2-yl)ethanone

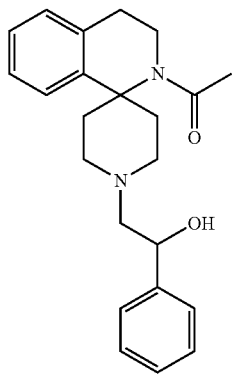 [SMILES: CC(=O)N1CCc2ccccc2C12CCN(CC(O)c1ccccc1)CC2]

A solution of lithium hydroxide monohydrate (25.7 mg, 0.61 mmol) in water (1 mL) was added to a solution of 2-(2-acetyl-3,4-dihydro-2H-spiro[isoquinoline-1,4'-piperidine]-1'-yl)-1-phenylethyl acetate (example 39, 83 mg, 0.20 mmol) in THF (1 mL). The mixture was stirred at room temperature overnight. It was diluted with water and extracted with DCM. The combined organic layers were dried over MgSO₄, filtered and concentrated to dryness. The crude residue was purified by flash chromatography on SiO₂ (mobile phase: MeOH/DCM mixtures of increasing polarity), to give the title compound (19 mg, yield 27%).

HPLC-MS (Method F): Ret, 3.66 min; ESI+-MS m/z, 365.1 (M+1).

Example 41

1-(1'-(2-Hydroxyethyl)-3,4-dihydro-2H-spiro[isoquinoline-1,4'-piperidine]-2-yl)ethanone

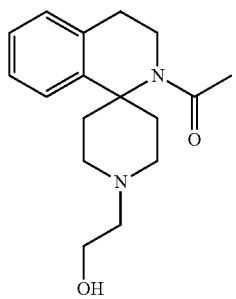 [SMILES: CC(=O)N1CCc2ccccc2C12CCN(CCO)CC2]

a) 2-(2-Acetyl-3,4-dihydro-2H-spiro[isoquinoline-1,4'-piperidin]-1'-yl)ethyl acetate Following the procedure described in example 8 using intermediate 2AT as starting material, the title compound was obtained.

HPLC-MS (Method F): Ret, 3.06 min; ESI⁺-MS m/z, 331.0 (M+1).

b) 1-(1'-(2-Hydroxyethyl)-3,4-dihydro-2H-spiro[isoquinoline-1,4'-piperidine]-2-yl)ethanone Following the procedure described in example 40, but using the compound obtained in step a as starting material, the title compound was obtained.

HPLC-MS (Method F): Ret, 2.33 min; ESI⁺-MS m/z, 289.0 (M+1).

Example 42

1-(1'-(2-(Pyridin-2-yloxy)ethyl)-3,4-dihydro-2H-spiro[isoquinoline-1,4'-piperidine]-2-yl)ethanone

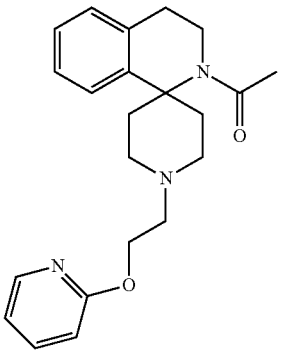

A mixture of the compound obtained in example 41 (55 mg, 0.19 mmol), Cs₂CO₃ (93 mg, 0.28 mmol), CuI (1 mg, 0.009 mmol), bathophenanthroline (0.006 mg, 0.02 mmol) and 2-iodopyridine (0.035 mL, 0.19 mmol) in dry toluene (1 mL) was heated under an argon atmosphere at 110° C. overnight. A second run of reagents was added and the mixture was again stirred at 110° C. overnight to get the reaction to completion. The reaction mixture was allowed to cool to r.t., it was diluted with EtOAc, filtered over a pad of celite and finally concentrated to dryness. The crude residue was purified by flash chromatography on C₁₈ (mobile phase: gradient aqueous NH₄HCO₃ (pH 8) to ACN) to give the title compound (36 mg, yield 52%).

HPLC-MS (Method F): Ret, 3.53 min; ESI⁺-MS m/z, 366.2 (M+1).

This method was used for the preparation of examples 43-44 using 3-iodopyridine and 4-iodopyridine, respectively, instead of 2-iodopyridine:

| EX | Structure | Chemical name | Method | Ret (min) | MS (M + H) |
|---|---|---|---|---|---|
| 43 | 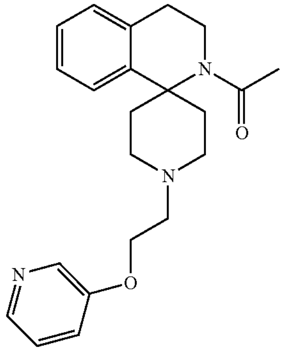 [SMILES: CC(=O)N1CCc2ccccc2C12CCN(CCOc1cccnc1)CC2] | 1-(1'-(2-(pyridin-3-yloxy)ethyl)-3,4-dihydro-2H-spiro[isoquinoline-1,4'-piperidine]-2-yl)ethanone | F | 3.22 | 366.2 |
| 44 | 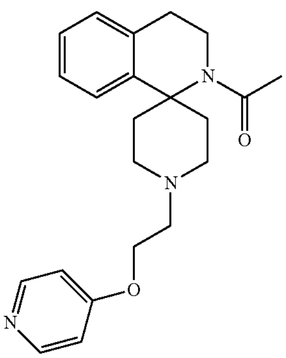 [SMILES: CC(=O)N1CCc2ccccc2C12CCN(CCOc1ccncc1)CC2] | 1-(1'-(2-(pyridin-4-yloxy)ethyl)-3,4-dihydro-2H-spiro[isoquinoline-1,4'-piperidine]-2-yl)ethanone | F | 3.16 | 366.2 |

Example 45

1N-(4-(2-(2-acetyl-3,4-dihydro-2H-spiro[isoquinoline-1,4'-piperidine]-1'-yl)ethyl)pyridin-2-yl)acetamide

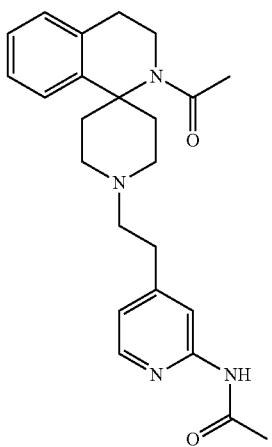 [SMILES: CC(=O)Nc1cc(CCN2CCC3(CC2)c2ccccc2CCN3C(C)=O)ccn1]

Following the procedure described in example 8, but using intermediate 2AO as starting material and 3 equivalents of acetyl chloride, N-acetyl-N-(4-(2-(2-acetyl-3,4-dihydro-2H-spiro[isoquinoline-1,4'-piperidin]-1'-yl)ethyl) pyridin-2-yl)acetamide was obtained as a crude product. A solution of this peracetylated compound (43 mg, 096 mmol) in THF (3 mL) was treated with concentrated ammonia (0.02 mL, 0.29 mmol) at room temperature for 6 h. The mixture was diluted with water and DCM. The combined organic layers were dried over MgSO₄, filtered and concentrated. The crude residue was purified by flash chromatography on SiO₂ (mobile phase: MeOH/DCM mixtures of increasing polarity) to give the title compound (24 mg, yield 62%).

HPLC-MS (Method F): Ret, 3.11 min; ESI⁺-MS m/z, 407.2 (M+1).

Example 46 tert-Butyl 2-(2-acetyl-3,4-dihydro-2H-spiro[isoquinoline-1,4'-piperidine]-1'-yl)ethyl(methyl)carbamate

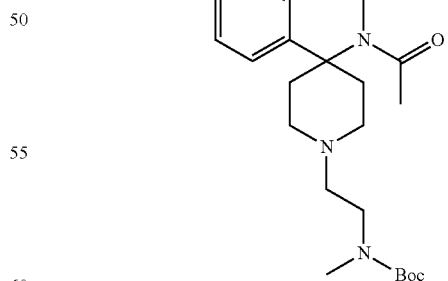

To a solution of example 37 (181 mg, 0.47 mmol) in dry DMF (3 mL), NaH (31 mg, 60 wt % in mineral oil, 0.71 mmol) was added at r.t. The reaction mixture was stirred at r.t. for 30 min, then iodomethane (0.032 mL, 0.51 mmol) was added and the resulting suspension was stirred at r.t. for 4 h. Additional NaH (16 mg, 60 wt % in mineral oil, 0.35 mmol) and iodomethane (0.01 mL, 0.17 mmol) were added and the reaction mixture was stirred at r.t. for further 6 h. Water was slowly added and it was extracted thrice with DCM. The organic phases were combined, washed with brine, dried over MgSO4, filtered and concentrated to dryness. The residue was purified by flash chromatography on $C_{18}$ (mobile phase: gradient aqueous $NH_4HCO_3$ (pH 8) to ACN) to give the title compound (63 mg, yield 34%).

HPLC-MS (Method F): Ret, 4.06 min; ESI+-MS m/z, 402.2 (M+1).

Example 47

1-(1'-(2-(Methylamino)ethyl)-3,4-dihydro-2H-spiro[isoquinoline-1,4'-piperidine]-2-yl)ethanone

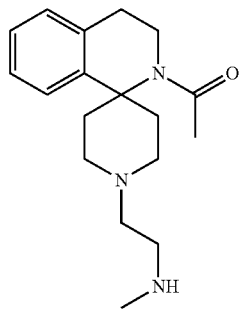 [SMILES: CNCCN1CCC2(CC1)c1ccccc1CCN2C(C)=O]

Trifluoroacetic acid (0.12 mL, 1.5 mmol) was added to a solution of tert-butyl 2-(2-acetyl-3,4-dihydro-2H-spiro[isoquinoline-1,4'-piperidine]-1'-yl)ethyl(methyl)carbamate (example 46, 63 mg, 0.15 mmol) in DCM (3 mL), and the reaction mixture was stirred at r.t. for 4 h. The solvent was evaporated to dryness to give the title compound (118 mg, quant yield).

HPLC-MS (Method F): Ret, 2.48 min; ESI+-MS m/z, 302.2 (M+1).

Example 48

N-(2-(2-Acetyl-3,4-dihydro-2H-spiro[isoquinoline-1,4'-piperidine]-1'-yl)ethyl)-N-methylbenzamide

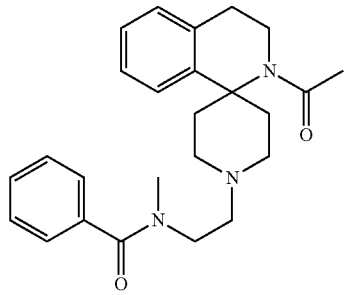 [SMILES: CC(=O)N1CCc2ccccc2C12CCN(CCN(C)C(=O)c1ccccc1)CC2]

Benzoyl chloride (0.025 mL, 0.19 mmol) was added at 0° C. to a solution of 1-(1'-(2-(methylamino)ethyl)-3,4-dihydro-2H-spiro[isoquinoline-1,4'-piperidine]-2-yl)ethanone (example 47, 118 mg, 0.15 mmol) and TEA (0.205 mL, 1.20 mmol) in DCM (3 mL), and the reaction mixture was stirred at r.t. overnight. It was then diluted with NaHCO3 sat. sol. and extracted with DCM. The combined organic layers were dried over MgSO4, filtered and concentrated. The crude residue was purified by flash chromatography on $C_{18}$ (mobile phase: gradient aqueous $NH_4HCO_3$ (pH 8) to ACN) to give the title compound (13 mg, yield 21%).

HPLC-MS (Method F): Ret, 3.52 min; ESI+-MS m/z, 406.2 (M+1).

Example 49

2-Acetyl-1'-phenethyl-3,4-dihydro-2H-spiro[isoquinoline-1,4'-piperidine]-6-yl acetate

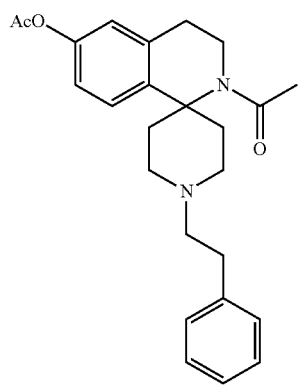 [SMILES: CC(=O)Oc1ccc2c(c1)CCN(C(C)=O)C21CCN(CCc2ccccc2)CC1]

A microwave reaction tube was charged with 1'-phenethyl-3,4-dihydro-2H-spiro[isoquinoline-1,4'-piperidin]-6-ol (intermediate 2AU, 1.27 g, 3.9 mmol) and dissolved in acetic anhydride (18 mL). The reaction mixture was subjected to microwave irradiating conditions for 10 min at 120° C. After cooling to r.t., aqueous saturated solution NaHCO3 was added and the reaction mixture was extracted three times with DCM. The combined organic layers were washed with water, dried over Na2SO4, filtered and evaporated under vacuum to yield the title compound (1.37 g, quantitative yield)

HPLC-MS (Method H): Ret, 1.77 min; ESI+-MS m/z, 407.3 (M+1).

Example 50

1-(6-Hydroxy-1'-phenethyl-3,4-dihydro-2H-spiro[isoquinoline-1,4'-piperidine]-2-yl)ethanone

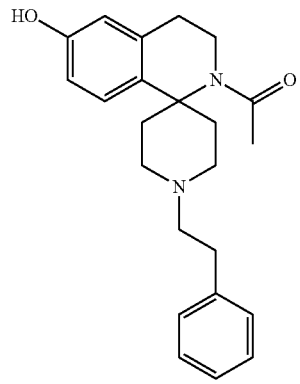 [SMILES: CC(=O)N1CCc2cc(O)ccc2C12CCN(CCc1ccccc1)CC2]

To a solution of 2-acetyl-1'-phenethyl-3,4-dihydro-2H-spiro[isoquinoline-1,4'-piperidine]-6-yl acetate (example 49, 1.6 g, 4 mmol) in methanol (25 mL), K₂CO₃ (613 mg, 4 mmol) was added and the reaction mixture was stirred at 0° C. for 2 hours. The solvent was evaporated to dryness and the residue was partioned in DCM and water twice. The combined organic layers were washed with water, dried over Na₂SO₄, filtered and evaporated under vacuum. The crude residue was purified by flash chromatography on SiO₂, gradient DCM to methanol:DCM (85:15) to give the title compound as a beige solid (967 mg, 67%)

HPLC-MS (Method H): Ret, 1.53 min; ESI⁺-MS m/z, 365.3 (M+1).

Example 51

1-(6-Chloro-1'-phenethyl-3,4-dihydro-2H-spiro[isoquinoline-1,4'-piperidine]-2-yl)ethanone

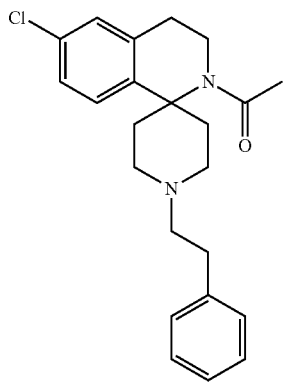 [SMILES: CC(=O)N1CCc2cc(Cl)ccc2C12CCN(CCc1ccccc1)CC2]

a) 2-Acetyl-1'-phenethyl-3,4-dihydro-2H-spiro[isoquinoline-1,4'-piperidine]-6-yl trifluoromethanesulfonate A solution of 1-(6-hydroxy-1'-phenethyl-3,4-dihydro-2H-spiro[isoquinoline-1,4'-piperidine]-2-yl)ethanone (example 50, 250 mg, 0.69 mmol) and triethylamine (134 mL, 0.96 mmol) in DCM (8 mL) was cooled to 0° C. and trifluoromethanesulfonyl chloride (160 mL, 1.5 mmol) was added dropwise. The solution was allowed to reach r.t. and was stirred overnight. The reaction mixture was poured into water and the layers separated. The aqueous layer was additionally extracted with DCM. The combined organic fractions were washed with 2N NaOH solution, followed by brine. The organic phase was dried over Na₂SO₄ and the solvent was removed to yield the title compound as a crude oil (334 mg), which was used in the next step without further purification.

b) Title Compound

A microwave reaction tube was charged under argon with the compound obtained in step a (70 mg, 0.14 mmol), Pd₂(dba)₃ (5.1 mg, 0.006 mmol), tBuBrettPhos (5.5 mg, 0.011 mol), CsF (43 mg, 0.28 mmol) and toluene (2 mL). The reaction tube was sealed and subjected to microwave irradiating conditions for 1 h at 160° C. After cooling back to r.t., the solvent was evaporated under reduced pressure and the crude directly absorbed onto silica gel with the aid of ethyl acetate. The crude residue was purified by flash chromatography on SiO₂ (gradient DCM to methanol:DCM (90:10)), followed by purification by semipreparative reverse phase HPLC (X-Bridge C18, 5 mm, MeCN/NH₄HCO₃ 10 mM, flow 20 mL/min., r.t.) to give the title compound (2.5 mg, 5%) as clear oil.

HPLC-MS (Method H): Ret, 2.04 min; ESI⁺-MS m/z, 383.1 (M+1).

Example 52

2-Hydroxy-1-(1'-phenethyl-3,4-dihydro-2H-spiro[isoquinoline-1,4'-piperidin]-2-yl)ethanone

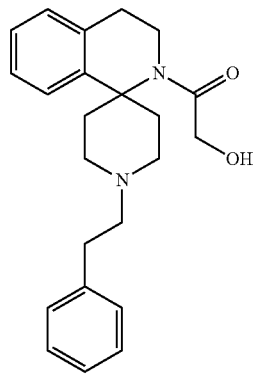 [SMILES: O=C(CO)N1CCc2ccccc2C12CCN(CCc1ccccc1)CC2]

BBr₃ solution (1.0 M in DCM, 4.1 mL, 4.1 mmol) was added to a −40° C. cooled solution of 2-methoxy-1-(1'-phenethyl-3,4-dihydro-2H-spiro[isoquinoline-1,4'-piperidine]-2-yl)ethanone (example 5, 155 mg, 0.409 mmol) in DCM (10 mL). The reaction mixture was allowed to reach r.t. and stirred at this temperature for 18 h. The reaction mixture was poured into H₂O and extracted with DCM. The combined organic layers were washed with NaHCO₃ saturated aqueous solution, dried over Na₂SO₄, filtered and concentrated. The crude residue was purified by flash chromatography on SiO₂ (DCM/MeOH/NH₄OH 97:3:1) and slurred with Et₂O, to give the title compound as a white solid (100 mg, yield 67%).

HPLC-MS (Method B): Ret, 13.98 min; ESI⁺-MS m/z: 365.2 (M+1).

Example 53

2-(Methylsulfonyl)-1'-phenethyl-3,4-dihydro-2H-spiro[isoquinoline-1,4'-piperidine]

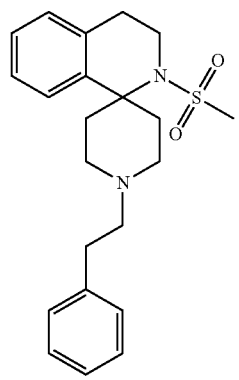 [SMILES: CS(=O)(=O)N1CCc2ccccc2C12CCN(CCc1ccccc1)CC2]

Methanesulphonyl chloride (0.380 mL, 4.89 mmol) was added to a suspension of 1'-(2-phenylethyl)-3,4-dihydro-2H-spiro[isoquinoline-1,4'-piperidine] (intermediate 2C, 150 mg, 0.489 mmol), DMAP (12 mg, 0.097 mmol) and pyridine (0.395 mL, 4.89 mmol) in DCE (15 mL). The reaction mixture was warmed up to 70° C. and stirred at this temperature for 4 days in a sealed tube. The reaction mixture was allowed to reach r.t., poured into $H_2O$ and extracted with DCM. The combined organic layers were washed with 10% aqueous solution of citric acid, dried over $Na_2SO_4$, filtered and concentrated. The crude residue was purified by flash chromatography on $SiO_2$ (AcOEt/MeOH/$NH_4OH$ 95:5:1→90:10:1) and preparative HPLC, to yield the title compound as a pale brown solid (17 mg, yield 9%).

HPLC-MS (Method B): Ret, 15.05 min; $ESI^+$-MS m/z, 385.1 (M+1).

Examples 54-62

Following a method similar to that used in the preparation of Intermediate 3C, but using suitable starting materials examples 54-62 were obtained:

| EX | Structure | Chemical name | Method | Ret (min) | MS (M + H) |
|---|---|---|---|---|---|
| 54 | 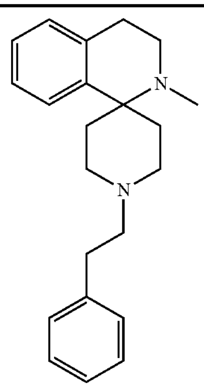 | 2-methyl-1'-phenethyl-3,4-dihydro-2H-spiro[iso-quinoline-1,4'-piperidine] | B | 16.52 | 321.3 |
| 55 | 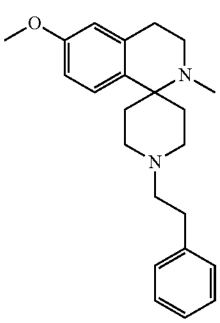 [SMILES: COc1ccc2c(c1)CCN(C)C21CCN(CCc2ccccc2)CC1] | 6-methoxy-2-methyl-1'-phenethyl-3,4-dihydro-2H-spiro[iso-quinoline-1,4'-piperidine] | H | 2.05 | 351.3 |
| 56 | 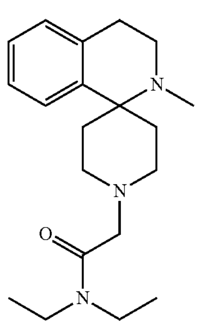 [SMILES: CCN(CC)C(=O)CN1CCC2(CC1)c1ccccc1CCN2C] | N,N-diethyl-2-(2-methyl-3,4-dihydro-2H-spiro[iso-quinoline-1,4'-piperidine]-1'-yl)acetamide | F | 3.89 | 330.2 |
| 57 | | 2-(2-methyl-3,4-dihydro-2H-spiro[iso-quinoline-1,4'-piperidine]-1'-yl)-1-(1,4-oxazepan-4-yl)ethanone | F | 3.29 | 358.2 |
| 58 | | 1-(4-fluoro-piperidin-1-yl)-2-(2-methyl-3,4-dihydro-2H-spiro[iso-quinoline-1,4'-piperidine]-1'-yl)ethanone | F | 3.79 | 360.2 |
| 59 | | 1-(4-(2-hydroxy-propan-2-yl)piperidin-1-yl)-2-(2-methyl-3,4-dihydro-2H-spiro[iso-quinoline-1,4'-piperidine]-1'-yl)ethanone | F | 3.44 | 400.3 |

-continued

| EX | Structure | Chemical name | Method | Ret (min) | MS (M + H) |
|---|---|---|---|---|---|
| 60 | 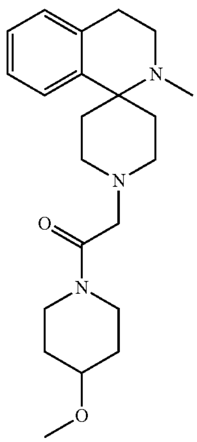 [SMILES: COC1CCN(C(=O)CN2CCC3(CC2)c2ccccc2CCN3C)CC1] | 1-(4-methoxy-piperidin-1-yl)-2-(2-methyl-3,4-dihydro-2H-spiro[iso-quinoline-1,4'-piperidine]-1'-yl)ethanone | F | 3.61 | 372.2 |
| 61 | 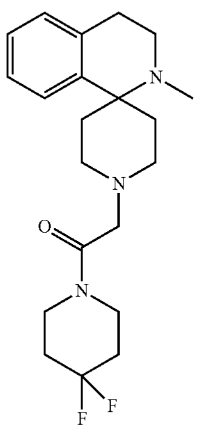 [SMILES: CN1CCc2ccccc2C12CCN(CC(=O)N1CCC(F)(F)CC1)CC2] | 1-(4,4-difluoro-piperidin-1-yl)-2-(2-methyl-3,4-dihydro-2H-spiro[iso-quinoline-1,4'-piperidine]-1'-yl)ethanone | F | 4.13 | 378.2 |
| 62 | 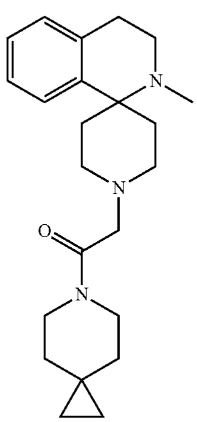 [SMILES: CN1CCc2ccccc2C12CCN(CC(=O)N1CCC3(CC1)CC3)CC2] | 2-(2-methyl-3,4-dihydro-2H-spiro[iso-quinoline-1,4'-piperidine]-1'-yl)-1-(6-azaspiro[2.5]octan-6-yl)ethanone | F | 4.42 | 368.2 |

Example 63

2-Ethyl-1'-phenethyl-3,4-dihydro-2H-spiro[isoquinoline-1,4'-piperidine]

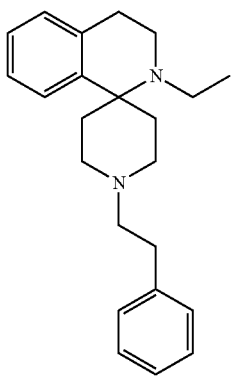 [SMILES: CCN1CCc2ccccc2C12CCN(CCc1ccccc1)CC2]

NaBH(OAc)$_3$ (329 mg, 1.55 mmol), acetaldehyde (87 mL, 1.55 mmol) and AcOH (88 mL, 1.55 mmol) were added to a solution of 1'-(2-phenylethyl)-3,4-dihydro-2H-spiro[isoquinoline-1,4'-piperidine] (intermediate 2C, 238 mg, 0.776 mmol) in DCE (3 mL). The reaction mixture was heated by microwave irradiation (120° C., 2×45 min), allowed to reach r.t., poured into NaHCO$_3$ saturated aqueous solution and extracted with DCM. The combined organic layers were dried over Na$_2$SO$_4$, filtered and concentrated. The crude residue was purified by flash chromatography on SiO$_2$ (EtOAc/MeOH/NH$_4$OH 98:2:1→95:5:1), to give the title compound as a yellow oil (180 mg, yield 69%).

HPLC-MS (Method B): Ret, 17.20 min; ESI$^+$-MS m/z, 335.2 (M+1).

This method was used for the preparation of example 64, using 2-thiazolecarboxaldehyde instead of acetaldehyde:

| EX | Structure | Chemical name | Method | Ret (min) | MS (M + H) |
|---|---|---|---|---|---|
| 64 | 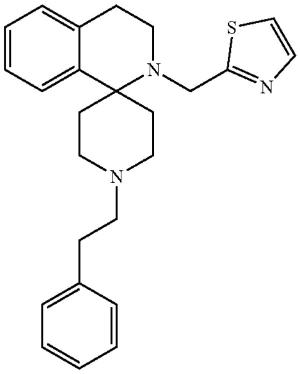 [SMILES: c1ccc(CCN2CCC3(CC2)c2ccccc2CCN3Cc2nccs2)cc1] | 2-((1'-phenethyl-3,4-dihydro-2H-spiro[isoquinoline-1,4'-piperidine]-2-yl)methyl)thiazole | F | 4.97 | 404.2 |

Example 65

4-(2-(2-Methyl-3,4-dihydro-2H-spiro[isoquinoline-1,4'-piperidine]-1'-yl)ethyl)morpholine

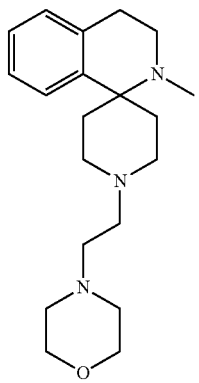 [SMILES: CN1CCc2ccccc2C12CCN(CCN1CCOCC1)CC2]

a) 2-Methyl-3,4-dihydro-2H-spiro[isoquinoline-1,4'-piperidine]

1'-Benzyl-2-methyl-3,4-dihydro-2H-spiro[isoquinoline-1,4'-piperidine] (intermediate 3C, 1.04 g, 3.39 mmol) was added to a suspension of Pd(OH)$_2$ (532 mg, 18.50% Pd, 48.40% H$_2$O w/w, 0.339 mmol) and AcOH (19 µL, 0.339 mmol) in MeOH (15 mL). The suspension was stirred under H$_2$ atmosphere (balloon) for 19 h. The reaction mixture was filtered through Celite, rinsed with MeOH and concentrated. The resulting oil was purified by flash chromatography on SiO$_2$ (DCM/MeOH/NH$_4$OH 90:10:1→80:20:1), to furnish the title compound as a white solid (705 mg, yield 96%).

HPLC-MS (Method B): Ret, 10.63 min; ESI$^+$-MS m/z, 217.0 (M+1).

b) 4-(2-(2-Methyl-3,4-dihydro-2H-spiro[isoquinoline-1,4'-piperidine]-1'-yl)ethyl)morpholine To a suspension of K$_2$CO$_3$ (449 mg, 3.25 mmol) and the compound obtained in step a (469 mg, 2.17 mmol) in ACN (25 mL), 4-(2-chloroethyl)morpholine (487 mg, 3.25 mmol) was added. The reaction was refluxed for 4.5 h and it was cooled down to r.t. The mixture was poured into H$_2$O and the aqueous layer was extracted with EtOAc. The combined organic layers were washed with H$_2$O, dried over Na$_2$SO$_4$, filtered and concentrated. The crude residue was purified by flash chromatography on SiO$_2$ (DCM/MeOH/NH$_4$OH 95:5:1→90:10:1), to give the title compound as a white solid (414 mg, yield 69%)

HPLC-MS (Method D): Ret, 16.89 min; ESI$^+$-MS m/z, 330.1 (M+1).

This method was used for the preparation of examples 66-112 using suitable

| EX | Structure | Chemical name | Method | Ret (min) | MS (M + H) |
|---|---|---|---|---|---|
| 66 | 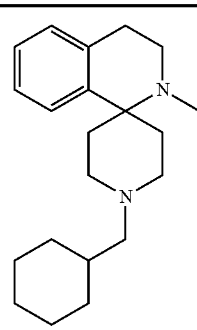 | 1'-(cyclohexylmethyl)-2-methyl-3,4-dihydro-2H-spiro[isoquinoline-1,4'-piperidine] | B | 20.32 | 313.1 |

-continued

| EX | Structure | Chemical name | Method | Ret (min) | MS (M + H) |
|---|---|---|---|---|---|
| 67 | 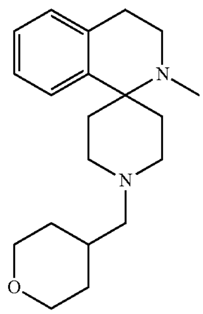 [SMILES: CN1CCc2ccccc2C12CCN(CC1CCOCC1)CC2] | 2-methyl-1'-((tetrahydro-2H-pyran-4-yl)methyl)-3,4-dihydro-2H-spiro[isoquinoline-1,4'-piperidine] | D | 16.76 | 315.4 |
| 68 | 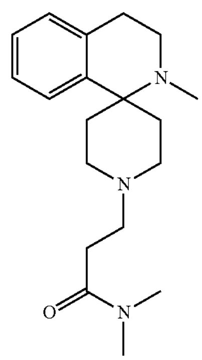 [SMILES: CN(C)C(=O)CCN1CCC2(CC1)c1ccccc1CCN2C] | N,N-dimethyl-3-(2-methyl-3,4-dihydro-2H-spiro[isoquinoline-1,4'-piperidine]-1'-yl)propanamide | D | 13.17 | 316.2 |
| 69 | 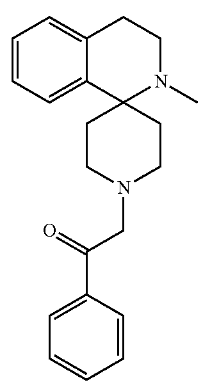 [SMILES: CN1CCc2ccccc2C12CCN(CC(=O)c1ccccc1)CC2] | 2-(2-methyl-3,4-dihydro-2H-spiro[isoquinoline-1,4'-piperidine]-1'-yl)-1-phenylethanone | C | 15.92 | 335.1 |
| 70 | 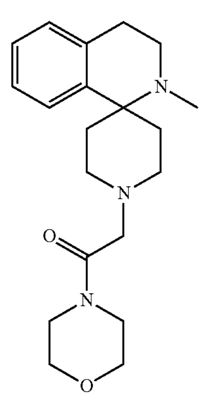 [SMILES: CN1CCc2ccccc2C12CCN(CC(=O)N1CCOCC1)CC2] | 2-(2-methyl-3,4-dihydro-2H-spiro[isoquinoline-1,4'-piperidine]-1'-yl)-1-morpholinoethanone | D | 13.8 | 344.1 |

-continued

| EX | Structure | Chemical name | Method | Ret (min) | MS (M + H) |
|---|---|---|---|---|---|
| 71 | 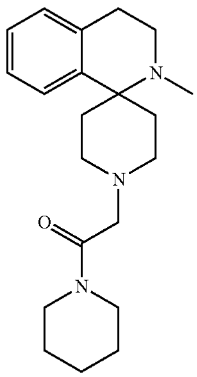 [SMILES: CN1CCc2ccccc2C12CCN(CC(=O)N1CCCCC1)CC2] | 2-(2-methyl-3,4-dihydro-2H-spiro[isoquinoline-1,4'-piperidine]-1'-yl)-1-(piperidin-1-yl)ethanone | C | 14.67 | 342.2 |
| 72 | 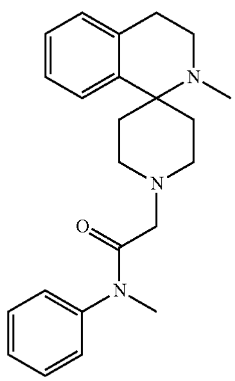 [SMILES: CN(C(=O)CN1CCC2(CC1)c1ccccc1CCN2C)c1ccccc1] | N-methyl-2-(2-methyl-3,4-dihydro-2H-spiro[isoquinoline-1,4'-piperidine]-1'-yl)-N-phenylacetamide | C | 15.42 | 364.1 |
| 73 | 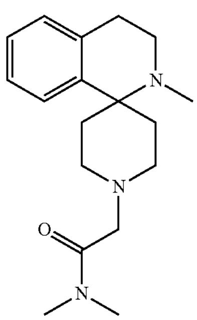 [SMILES: CN(C)C(=O)CN1CCC2(CC1)c1ccccc1CCN2C] | N,N-dimethyl-2-(2-methyl-3,4-dihydro-2H-spiro[isoquinoline-1,4'-piperidine]-1'-yl)acetamide | D | 13.51 | 302.2 |
| 74 | 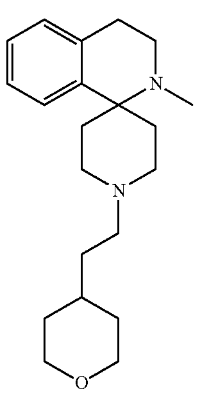 | 2-methyl-1'-(2-(tetrahydro-2H-pyran-4-yl)ethyl)-3,4-dihydro-2H-spiro[isoquinoline-1,4'-piperidine] | B | 13.05 | 329.2 |

-continued

| EX | Structure | Chemical name | Method | Ret (min) | MS (M + H) |
|---|---|---|---|---|---|
| 75 | 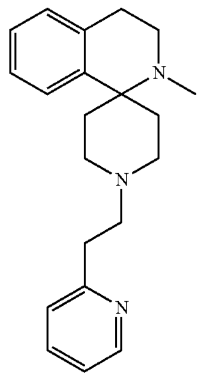 [SMILES: CN1CCc2ccccc2C12CCN(CCc1ccccn1)CC2] | 2-methyl-1'-(2-(pyridin-2-yl)ethyl)-3,4-dihydro-2H-spiro[isoquinoline-1,4'-piperidine] | D | 15.43 | 322.2 |
| 76 | 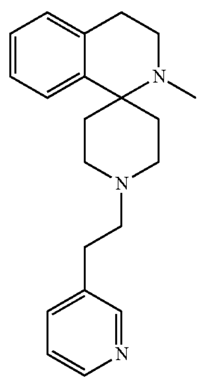 [SMILES: CN1CCc2ccccc2C12CCN(CCc1cccnc1)CC2] | 2-methyl-1'-(2-(pyridin-3-yl)ethyl)-3,4-dihydro-2H-spiro[isoquinoline-1,4'-piperidine] | B | 13.58 | 322.2 |
| 77 | 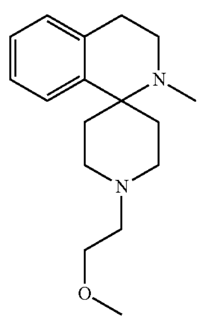 [SMILES: COCCN1CCC2(CC1)c1ccccc1CCN2C] | 1'-(2-methoxyethyl)-2-methyl-3,4-dihydro-2H-spiro[isoquinoline-1,4'-piperidine] | D | 14.02 | 275.3 |
| 78 | 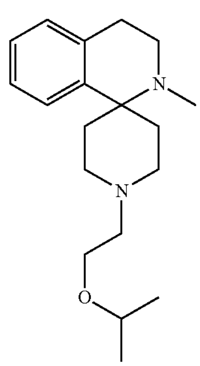 [SMILES: CC(C)OCCN1CCC2(CC1)c1ccccc1CCN2C] | 1'-(2-isopropoxyethyl)-2-methyl-3,4-dihydro-2H-spiro[isoquinoline-1,4'-piperidine] | D | 15.31 | 303.1 |

-continued

| EX | Structure | Chemical name | Method | Ret (min) | MS (M + H) |
|---|---|---|---|---|---|
| 79 | 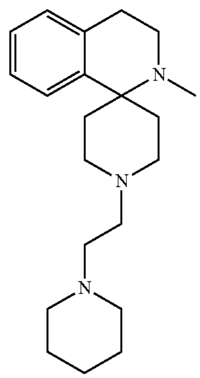 [SMILES: CN1CCc2ccccc2C12CCN(CCN1CCCCC1)CC2] | 2-methyl-1'-(2-(piperidin-1-yl)ethyl)-3,4-dihydro-2H-spiro[isoquinoline-1,4'-piperidine] | D | 15.24 | 328.1 |
| 80 | 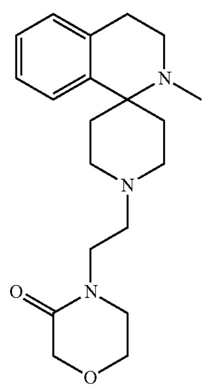 [SMILES: CN1CCc2ccccc2C12CCN(CCN1CCOCC1=O)CC2] | 4-(2-(2-methyl-3,4-dihydro-2H-spiro[isoquinoline-1,4'-piperidine]-1'-yl)ethyl)morpholin-3-one | D | 13.41 | 344.0 |
| 81 | 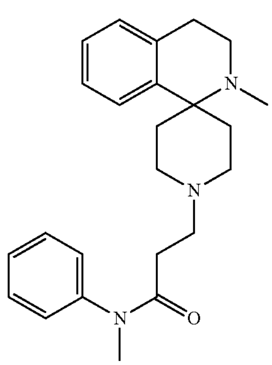 [SMILES: CN(C(=O)CCN1CCC2(CC1)c1ccccc1CCN2C)c1ccccc1] | N-methyl-3-(2-methyl-3,4-dihydro-2H-spiro[isoquinoline-1,4'-piperidine]-1'-yl)-N-phenylpropanamide | C | 14.98 | 378.2 |
| 82 | 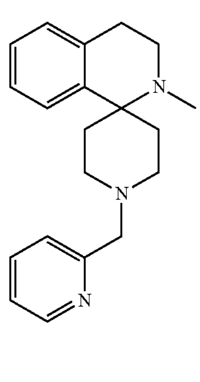 [SMILES: CN1CCc2ccccc2C12CCN(Cc1ccccn1)CC2] | 2-methyl-1'-(pyridin-2-ylmethyl)-3,4-dihydro-2H-spiro[isoquinoline-1,4'-piperidine] | D | 15.26 | 308.2 |

-continued

| EX | Structure | Chemical name | Method | Ret (min) | MS (M + H) |
|---|---|---|---|---|---|
| 83 | 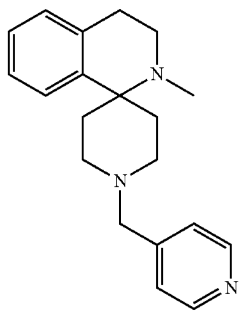 [SMILES: CN1CCc2ccccc2C12CCN(Cc1ccncc1)CC2] | 2-methyl-1'-(pyridin-4-ylmethyl)-3,4-dihydro-2H-spiro[isoquinoline-1,4'-piperidine] | D | 14.73 | 308.2 |
| 84 | 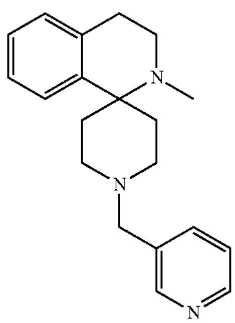 [SMILES: CN1CCc2ccccc2C12CCN(Cc1cccnc1)CC2] | 2-methyl-1'-(pyridin-3-ylmethyl)-3,4-dihydro-2H-spiro[isoquinoline-1,4'-piperidine] | D | 15.66 | 308.2 |
| 85 | 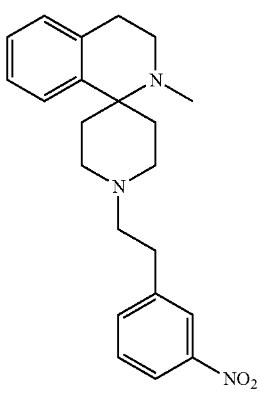 | 2-methyl-1'-(3-nitrophenethyl)-3,4-dihydro-2H-spiro[isoquinoline-1,4'-piperidine] | — | — | — |
| 86* | 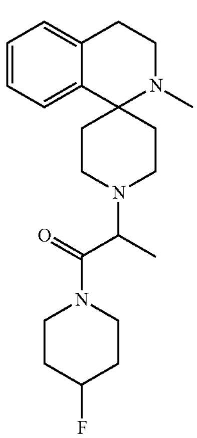 [SMILES: CC(C(=O)N1CCC(F)CC1)N1CCC2(CC1)c1ccccc1CCN2C] | 1-(4-fluoropiperidin-1-yl)-2-(2-methyl-3,4-dihydro-2H-spiro[isoquinoline-1,4'-piperidine]-1'-yl)propan-1-one | F | 3.94 | 374.2 |

-continued

| EX | Structure | Chemical name | Method | Ret (min) | MS (M + H) |
|---|---|---|---|---|---|
| 87 | 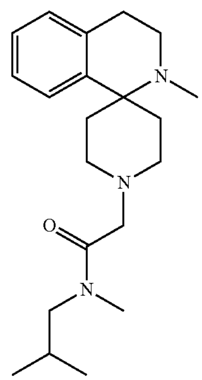 [SMILES: CC(C)CN(C)C(=O)CN1CCC2(CC1)c1ccccc1CCN2C] | N-isobutyl-N-methyl-2-(2-methyl-3,4-dihydro-2H-spiro[isoquinoline-1,4'-piperidine]-1'-yl)acetamide | F | 4.08 | 344.2 |
| 88 | 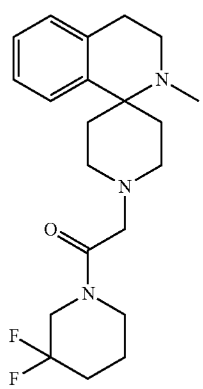 [SMILES: CN1CCc2ccccc2C12CCN(CC(=O)N1CCCC(F)(F)C1)CC2] | 1-(3,3-difluoropiperidin-1-yl)-2-(2-methyl-3,4-dihydro-2H-spiro[isoquinoline-1,4'-piperidine]-1'-yl)ethanone | F | 4.01 | 378.2 |
| 89 | 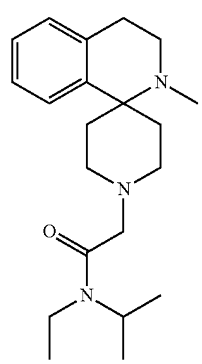 [SMILES: CCN(C(=O)CN1CCC2(CC1)c1ccccc1CCN2C)C(C)C] | N-ethyl-N-isopropyl-2-(2-methyl-3,4-dihydro-2H-spiro[isoquinoline-1,4'-piperidine]-1'-yl)acetamide | F | 4.10 | 344.2 |
| 90 | 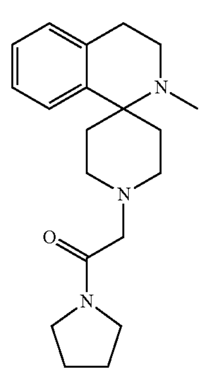 [SMILES: CN1CCc2ccccc2C12CCN(CC(=O)N1CCCC1)CC2] | 2-(2-methyl-3,4-dihydro-2H-spiro[isoquinoline-1,4'-piperidine]-1'-yl)-1-(pyrrolidin-1-yl)ethanone | F | 3.37 | 328.2 |

-continued

| EX | Structure | Chemical name | Method | Ret (min) | MS (M + H) |
|----|-----------|---------------|--------|-----------|------------|
| 91 | 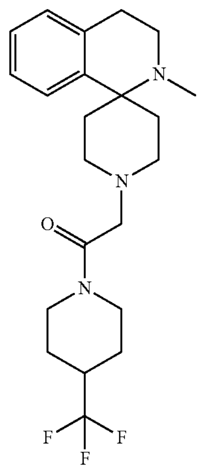 [SMILES: CN1CCc2ccccc2C12CCN(CC(=O)N1CCC(C(F)(F)F)CC1)CC2] | 2-(2-methyl-3,4-dihydro-2H-spiro[isoquinoline-1,4'-piperidine]-1'-yl)-1-(4-(trifluoromethyl)piperidin-1-yl)ethanone | F | 4.36 | 410.2 |
| 92 | 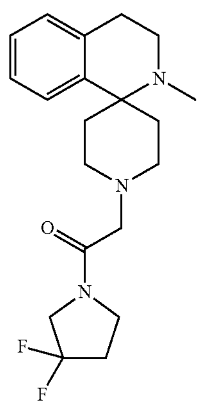 [SMILES: CN1CCc2ccccc2C12CCN(CC(=O)N1CCC(F)(F)C1)CC2] | 1-(3,3-difluoropyrrolidin-1-yl)-2-(2-methyl-3,4-dihydro-2H-spiro[isoquinoline-1,4'-piperidine]-1'-yl)ethanone | F | 3.69 | 364.2 |
| 93 | 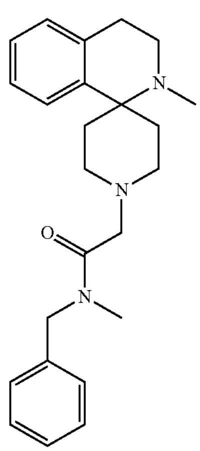 [SMILES: CN(Cc1ccccc1)C(=O)CN1CCC2(CC1)c1ccccc1CCN2C] | N-benzyl-N-methyl-2-(2-methyl-3,4-dihydro-2H-spiro[isoquinoline-1,4'-piperidine]-1'-yl)acetamide | F | 4.32 | 378.2 |

-continued

| EX | Structure | Chemical name | Method | Ret (min) | MS (M + H) |
|---|---|---|---|---|---|
| 94 | 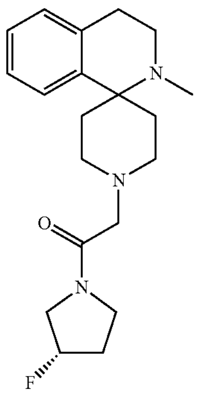 [SMILES: CN1CCc2ccccc2C12CCN(CC(=O)N1CC[C@H](F)C1)CC2] | (S)-1-(3-fluoropyrrolidin-1-yl)-2-(2-methyl-3,4-dihydro-2H-spiro[isoquinoline-1,4'-piperidine]-1'-yl)ethanone | F | 3.31 | 346.2 |
| 95 | 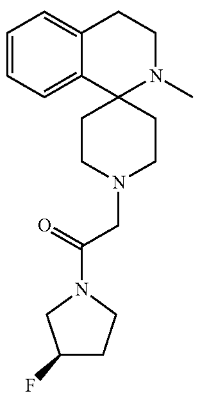 [SMILES: CN1CCc2ccccc2C12CCN(CC(=O)N1CC[C@@H](F)C1)CC2] | (R)-1-(3-fluoropyrrolidin-1-yl)-2-(2-methyl-3,4-dihydro-2H-spiro[isoquinoline-1,4'-piperidine]-1'-yl)ethanone | F | 3.31 | 346.2 |
| 96 | 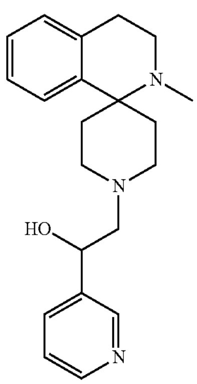 [SMILES: CN1CCc2ccccc2C12CCN(CC(O)c1cccnc1)CC2] | 2-(2-methyl-3,4-dihydro-2H-spiro[isoquinoline-1,4'-piperidine]-1'-yl)-1-(pyridin-3-yl)etanol | F | 3.20 | 338.2 |
| 97 | 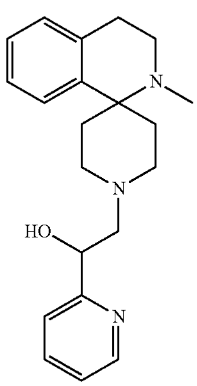 [SMILES: CN1CCc2ccccc2C12CCN(CC(O)c1ccccn1)CC2] | 2-(2-methyl-3,4-dihydro-2H-spiro[isoquinoline-1,4'-piperidine]-1'-yl)-1-(pyridin-2-yl)ethanol | F | 3.28 | 338.2 |

-continued

| EX | Structure | Chemical name | Method | Ret (min) | MS (M + H) |
|---|---|---|---|---|---|
| 98 | 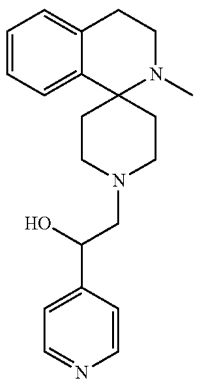 [SMILES: CN1CCc2ccccc2C12CCN(CC(O)c1ccncc1)CC2] | 2-(2-methyl-3,4-dihydro-2H-spiro[isoquinoline-1,4'-piperidine]-1'-yl)-1-(pyridin-4-yl)ethanol | F | 3.31 | 338.2 |
| 99* | 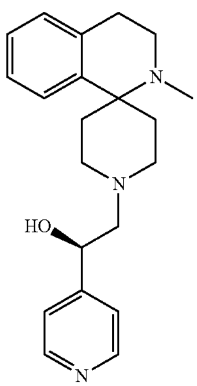 [SMILES: CN1CCc2ccccc2C12CCN(C[C@H](O)c1ccncc1)CC2] | (R)-2-(2-methyl-3,4-dihydro-2H-spiro[isoquinoline-1,4'-piperidine]-1'-yl)-1-(pyridin-4-yl)ethanol | H | 1.59 | 338.2 |
| 100* | 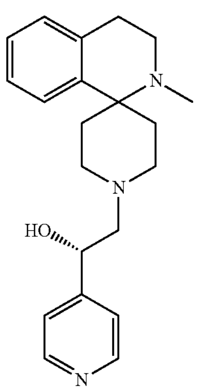 | (S)-2-(2-methyl-3,4-dihydro-2H-spiro[isoquinoline-1,4'-piperidine]-1'-yl)-1-(pyridin-4-yl)ethanol | H | 1.59 | 338.2 |
| 101 | 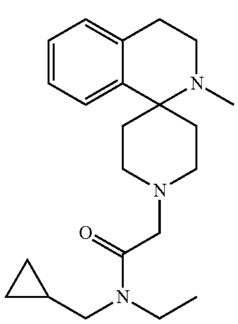 [SMILES: CCN(CC1CC1)C(=O)CN1CCC2(CC1)c1ccccc1CCN2C] | N-(cyclopropylmethyl)-N-ethyl-2-(2-methyl-3,4-dihydro-2H-spiro[isoquinoline-1,4'-piperidine]-1'-yl)acetamide | H | 1.97 | 356.2 |

-continued

| EX | Structure | Chemical name | Method | Ret (min) | MS (M + H) |
|---|---|---|---|---|---|
| 102 | 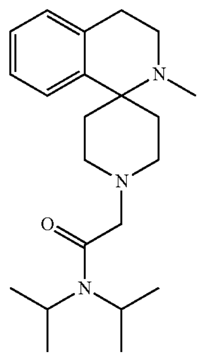 [SMILES: CC(C)N(C(=O)CN1CCC2(CC1)c1ccccc1CCN2C)C(C)C] | N,N-diisopropyl-2-(2-methyl-3,4-dihydro-2H-spiro[isoquinoline-1,4'-piperidine]-1'-yl)acetamide | H | 2.17 | 358.3 |
| 103 | 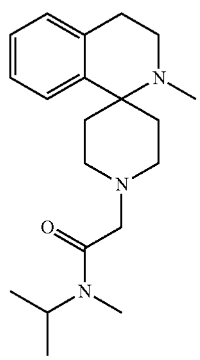 [SMILES: CC(C)N(C)C(=O)CN1CCC2(CC1)c1ccccc1CCN2C] | N-isopropyl-N-methyl-2-(2-methyl-3,4-dihydro-2H-spiro[isoquinoline-1,4'-piperidine]-1'-yl)acetamide | H | 1.77 | 330.3 |
| 104 | 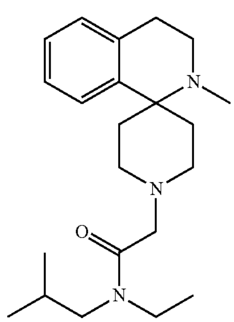 [SMILES: CCN(CC(C)C)C(=O)CN1CCC2(CC1)c1ccccc1CCN2C] | N-ethyl-N-isobutyl-2-(2-methyl-3,4-dihydro-2H-spiro[isoquinoline-1,4'-piperidine]-1'-yl)acetamide | H | 2.06 | 358.3 |
| 105 | 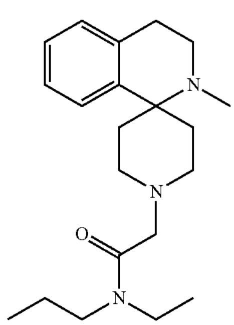 [SMILES: CCCN(CC)C(=O)CN1CCC2(CC1)c1ccccc1CCN2C] | N-ethyl-2-(2-methyl-3,4-dihydro-2H-spiro[isoquinoline-1,4'-piperidine]-1'-yl)-N-propylacetamide | H | 1.91 | 344.2. |

-continued

| EX | Structure | Chemical name | Method | Ret (min) | MS (M + H) |
|----|-----------|---------------|--------|-----------|------------|
| 106 | 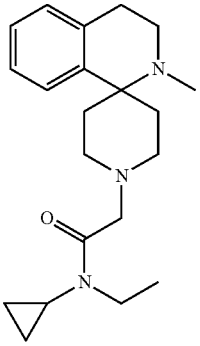 [SMILES: CCN(C(=O)CN1CCC2(CC1)c1ccccc1CCN2C)C1CC1] | N-cyclopropyl-N-ethyl-2-(2-methyl-3,4-dihydro-2H-spiro[isoquinoline-1,4'-piperidine]-1'-yl)acetamide | H | 1.73 | 342.3 |
| 107 | 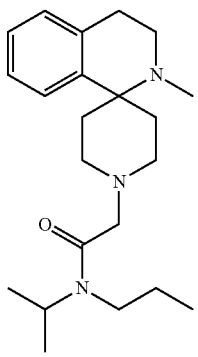 [SMILES: CCCN(C(=O)CN1CCC2(CC1)c1ccccc1CCN2C)C(C)C] | N-isopropyl-2-(2-methyl-3,4-dihydro-2H-spiro[isoquinoline-1,4'-piperidine]-1'-yl)-N-propylacetamide | H | 1.08 | 358.3 |
| 108 | 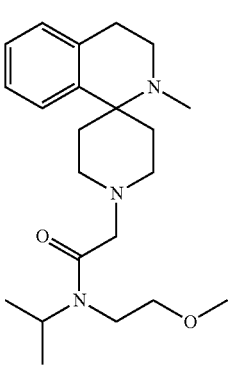 [SMILES: COCCN(C(=O)CN1CCC2(CC1)c1ccccc1CCN2C)C(C)C] | N-isopropyl-N-(2-methoxyethyl)-2-(2-methyl-3,4-dihydro-2H-spiro[isoquinoline-1,4'-piperidine]-1'-yl)acetamide | H | 1.83 | 374.3 |
| 109 | 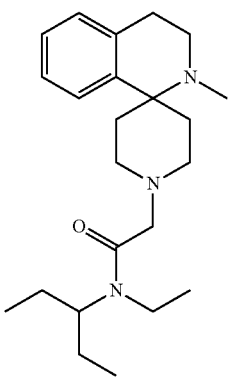 | N-ethyl-2-(2-methyl-3,4-dihydro-2H-spiro[isoquinoline-1,4'-piperidine]-1'-yl)-N-(pentan-3-yl)acetamide | H | 2.22 | 372.3 |

| EX | Structure | Chemical name | Method | Ret (min) | MS (M + H) |
|---|---|---|---|---|---|
| 110 | 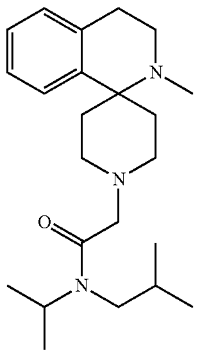 [SMILES: CC(C)CN(C(=O)CN1CCC2(CC1)c1ccccc1CCN2C)C(C)C] | N-isobutyl-N-isopropyl-2-(2-methyl-3,4-dihydro-2H-spiro[isoquinoline-1,4'-piperidine]-1'-yl)acetamide | H | 2.24 | 372.3 |
| 111 | 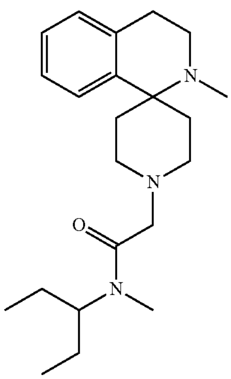 [SMILES: CCC(CC)N(C)C(=O)CN1CCC2(CC1)c1ccccc1CCN2C] | N-methyl-2-(2-methyl-3,4-dihydro-2H-spiro[isoquinoline-1,4'-piperidine]-1'-yl)-N-(pentan-3-yl)acetamide | H | 2.06 | 358.3 |
| 112 | 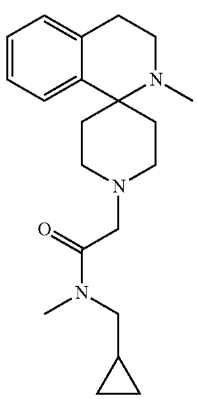 [SMILES: CN(CC1CC1)C(=O)CN1CCC2(CC1)c1ccccc1CCN2C] | N-(cyclopropylmethyl)-N-methyl-2-(2-methyl-3,4-dihydro-2H-spiro[isoquinoline-1,4'-piperidine]-1'-yl)acetamide | H | 1.80 | 342.3 |

*Example 86. RMN-$^1$H: $^1$H-NMR (CDCl$_3$, 250 MHz) δ: 8.11-8.06 (m, 2H, ArH); 7.58 (d, J = 8.0 Hz, 1H, ArH); 7.47 (t, J = 8.1 Hz, 1H, ArH); 7.34-7.05 (m, 4H, ArH); 3.19 (t, J = 6.4 Hz, 2H, CH2); 3.05-2.56 (m, 10H, CH$_2$); 2.31 (s, 3H, CH3); 2.07 (m, 4H, CH$_2$).

*Examples 99 and 100. Obtained by chiral preparative HPLC from example 98: Column: Chiralcel IC; Temperature: ambient; Flow: 10 mL/min; Mobile phase: n-Heptane/(EtOH + 0.33% DEA) 70/30 v/v.

Example 113

1-(3-fluoropyridin-4-yl)-2-(2-methyl-3,4-dihydro-2H-spiro[isoquinoline-1,4'-piperidine]-1'-yl)ethanol

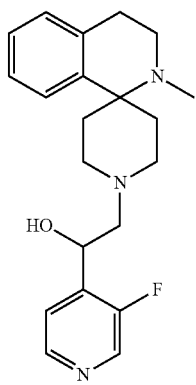 [SMILES: CN1CCc2ccccc2C12CCN(CC(O)c1ccncc1F)CC2]

To a solution of 3-fluoro-4-(oxiran-2-yl)pyridine (190 mg, 1.36 mmol) in ethanol (20 mL), 2-methyl-3,4-dihydro-2H-spiro[isoquinoline-1,4'-piperidine] (obtained in the synthesis of example 65 step a, 300 mg, 1.38 mmol) was added. The reaction mixture was refluxed overnight. Additional 3-fluoro-4-(oxiran-2-yl)pyridine (546 mg, 2.82 mmol) was then added and the reaction was refluxed overnight. Then, the mixture was concentrated to dryness and the crude residue was purified by flash chromatography on $SiO_2$ (DCM/MeOH 100:0→90:10), to give the title compound (125 mg, yield 25%)

HPLC-MS (Method H): Ret, 1.70 min; ESI$^+$-MS m/z, 356.2 (M+1).

This method was used as alternative preparation of examples 96-98.

Example 114

2-(2-Methyl-3,4-dihydro-2H-spiro[isoquinoline-1,4'-piperidine]-1'-yl)-1-(4-methylpiperidin-1-yl)ethanone

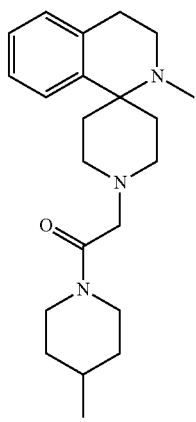 [SMILES: CC1CCN(C(=O)CN2CCC3(CC2)c2ccccc2CCN3C)CC1]

a) Ethyl 2-(3,4-dihydro-2H-spiro[isoquinoline-1,4'-piperidin]-1'-yl)acetate

A mixture of 3,4-dihydro-2H-spiro[isoquinoline-1,4'-piperidine] (obtained in the synthesis of intermediate 2W step a, 750 mg, 3.71 mmol), ethyl bromoacetate (0.35 mL, 3.16 mmol), DIPEA (1.4 mL, 7.9 mmol) and sodium iodide (241 mg, 1.58 mmol) in ACN (8 mL) was heated at 80° C. in a sealed tube for 24 h. It was diluted with water and extracted with EtOAc. The combined organic layers were washed with brine, dried over $MgSO_4$, filtered and concentrated. The crude was purified by flash chromatography on $SiO_2$ (mobile phase: MeOH/DCM mixtures of increasing polarity) to give the title compound (343 mg, yield 45%).

HPLC-MS (Method F): Ret, 3.14 min; ESI+-MS m/z, 289.1 (M+1).

b) Ethyl 2-(2-methyl-3,4-dihydro-2H-spiro[isoquinoline-1,4'-piperidin]-1'-yl)acetate Formaldehyde (37% aqueous solution, 1.6 mL, 21.0 mmol) was added to a solution of the compound obtained in step a (343 mg, 1.19 mmol) in MeOH (10 mL). The reaction mixture was stirred at r.t. for 22 h, $NaBH(OAc)_3$ (701 mg, 3.28 mmol) was added and the mixture was stirred at r.t. for 24 h. Additional formaldehyde and $NaBH(OAc)_3$ were added in a second reaction cycle to get the reaction to completion. The reaction mixture was slowly poured into $NaHCO_3$ saturated aqueous solution, the solvent was concentrated off and the residue was diluted with DCM. The organic layer was washed with $NaHCO_3$ saturated aqueous solution, brine and $H_2O$, dried over $MgSO_4$, filtered and concentrated. The residue was purified by flash chromatography on $C_{18}$ (mobile phase: gradient aqueous $NH_4HCO_3$ (pH 8) to ACN) to give the title compound (150 mg, yield 41%).

HPLC-MS (Method F): Ret, 3.94 min ESI$^+$-MS; m/z, 303.2 (M+1)

c) 2-(2-Methyl-3,4-dihydro-2H-spiro[isoquinoline-1,4'-piperidin]-1'-yl)acetic acid A solution of lithium hydroxide monohydrate (62 mg, 1.49 mmol) in water (2 mL) was added to a solution of the compound obtained in step b (150 mg, 0.50 mmol) in THF (2 mL). The mixture was stirred at room temperature for 4 h. It was diluted with water, pH was adjusted to 5 with 1 N HCl solution and it was extracted with DCM. The combined organic layers were dried over MgSO4, filtered and concentrated to dryness to give the title compound as a crude product (136 mg, quantitative yield).

HPLC-MS (Method F): Ret, 2.44 min ESI$^+$-MS; m/z, 275.1 (M+1)

d) Title Compound

HOBt (40 mg, 0.29 mmol), EDC.HCl (57 Mg, 0.29 mmol) and N-methylmorpholine (0.14 mL, 1.24 mmol) were added to a solution of compound obtained in step c (68 mg, 0.25 mmol) in DMF (2 mL). The mixture was stirred at r.t. for 30 min and then 4-methylpiperidine (0.03 mL, 0.25 mmol) was added and it was stirred at r.t. overnight. The reaction mixture was diluted with $NaHCO_3$ saturated aqueous solution and it was extracted with EtOAc. The combined organic layers were dried over $MgSO_4$, filtered and concentrated. The residue was purified by flash chromatography on $C_{18}$ (mobile phase: gradient aqueous $NH_4HCO_3$ (pH 8) to ACN) to give 2-(2-methyl-3,4-dihydro-2H-spiro[isoquinoline-1,4'-piperidine]-1'-yl)-1-(4-methylpiperidin-1-yl)ethanone (30 mg, yield 34%).

HPLC-MS (Method F): Ret, 4.36 min ESI⁺-MS; m/z, 356.2 (M+1)

This method was used for the preparation of examples 115-116 by reacting the compound obtained in example 114c with suitable amines:

| EX | Structure | Chemical name | Method | Ret (min) | MS (M + H) |
|---|---|---|---|---|---|
| 115 | 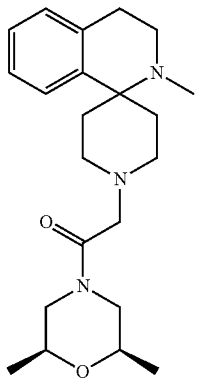 [SMILES: C[C@@H]1CN(C(=O)CN2CCC3(CC2)c2ccccc2CCN3C)C[C@H](C)O1] | 1-((2S,6R)-2,6-dimethyl-morpholino)-2-(2-methyl-3,4-dihydro-2H-spiro[isoquinoline-1,4'-piperidine]-1'-yl)ethanone | F | 3.79 | 372.2 |
| 116 | 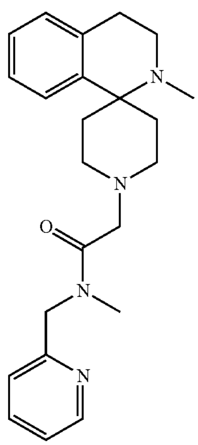 [SMILES: CN(Cc1ccccn1)C(=O)CN1CCC2(CC1)c1ccccc1CCN2C] | N-methyl-2-(2-methyl-3,4-dihydro-2H-spiro[isoquinoline-1,4'-piperidine]-1'-yl)-N-(pyridin-2-ylmethyl)acetamide | F | 3.45 | 379.2 |

Example 117

3-[2-(2-Methyl-3,4-dihydro-2H-spiro[isoquinoline-1,4'-piperidin]-1'-yl)-ethyl]-phenylamine

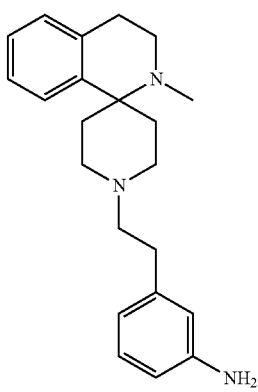 [SMILES: CN1CCc2ccccc2C12CCN(CCc1cccc(N)c1)CC2]

Following a similar procedure to that described in intermediate 2AS, but starting from the compound obtained in example 85 the title compound was obtained as an pale yellow solid (yield 62%).

HPLC-MS (Method B): Ret, 14.00 min; ESI⁺-MS m/z, 336.1 (M+1).

Example 118

N-(3-(2-(2-Methyl-3,4-dihydro-2H-spiro[isoquinoline-1,4'-piperidin]-1'-yl)ethyl)phenyl)methanesulfonamide

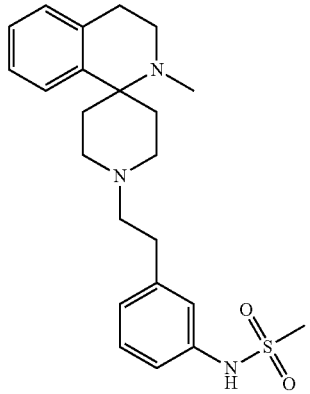 [SMILES: CN1CCc2ccccc2C12CCN(CCc1cccc(NS(C)(=O)=O)c1)CC2]

Methanesulphonyl chloride (17 mL, 0.22 mmol) was added to a 0° C. cooled solution of 3-[2-(2-methyl-3,4-dihydro-2H-spiro[isoquinoline-1,4'-piperidin]-1'-yl)-ethyl]-phenylamine (example 117, 66 mg, 0.20 mmol) in pyridine (0.70 mL). The reaction mixture was allowed to reach r.t. and stirred at this temperature for 4 h. The mixture was poured into NaHCO₃ saturated aqueous solution and extracted with DCM. The combined organic layers were dried over Na₂SO₄, filtered and concentrated. The crude residue was purified by flash chromatography on SiO₂ (1→10% MeOH/DCM) and slurred with hexanes, to yield the title compound as a yellow solid (38 mg, yield 47%).

HPLC-MS (Method C): Ret, 14.28 min; ESI⁺-MS m/z, 414.0 (M+1).

Example 119

N-{3-[2-(2-Methyl-3,4-dihydro-2H-spiro[isoquinoline-1,4'-piperidin]-1'-yl)-ethyl]-phenyl}-acetamide

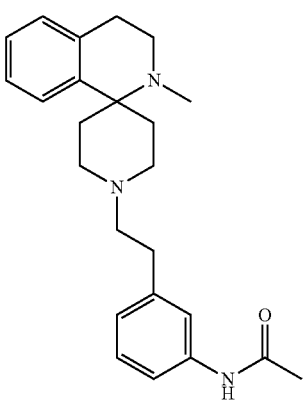 [SMILES: CC(=O)Nc1cccc(CCN2CCC3(CC2)c2ccccc2CCN3C)c1]

Following a similar procedure to that described in example 38, but starting from the compound obtained in example 117 the title compound was obtained as a white solid (yield 91%).

HPLC-MS (Method C): Ret, 14.04 min; ESI$^+$-MS m/z, 378.1 (M+1).

Example 120

2-(2-Methyl-3,4-dihydro-2H-spiro[isoquinoline-1,4'-piperidin]-1'-yl)-1-phenyl-ethanol

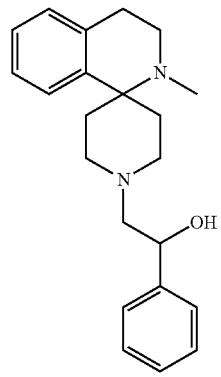 [SMILES: CN1CCc2ccccc2C12CCN(CC(O)c1ccccc1)CC2]

Styrene oxide (34 mL, 0.30 mmol) was added to a solution 2-methyl-3,4-dihydro-2H-spiro[isoquinoline-1,4'-piperidine] (obtained in the synthesis of example 65 step a, 65 mg, 0.30 mmol) in toluene (3 mL). The reaction mixture was warmed up to 115° C. and stirred at this temperature for 16 h in a sealed tube. It was cooled down to r.t., the solvent was concentrated and the residue was purified by flash chromatography on SiO$_2$ (DCM/MeOH/NH$_4$OH 98:2:1→90:10:1 and EtOAc/hexanes/NH$_4$OH 30:70:1→80:20:1) and slurred with hexanes, to give the title compound as a white solid (27 mg, yield 27%).

HPLC-MS (Method C): Ret, 14.80 min; ESI$^+$-MS m/z: 336.9 (M+1).

Example 121

2-Methyl-1'-(2-(pyridin-4-yl)ethyl)-3,4-dihydro-2H-spiro[isoquinoline-1,4'-piperidine]

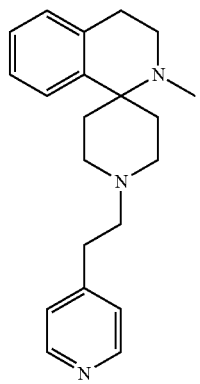 [SMILES: CN1CCc2ccccc2C12CCN(CCc1ccncc1)CC2]

a) 2-Methyl-1'-(pyridin-4-ylacetyl)-3,4-dihydro-2H-spiro[isoquinoline-1,4'-piperidine]

Following a similar procedure to that described in the synthesis of intermediate 2W step a, but starting from the compound obtained in example 65a, the title compound was obtained as a white solid (yield 63%).

HPLC-MS (Method A): Ret, 8.29 min; ESI$^+$-MS m/z, 336.2 (M+1).

b) Title Compound

Following a similar procedure to that described in the synthesis of intermediate 2W step c, but starting from the compound obtained step a, the title compound was obtained as a white solid (yield 74%).

HPLC-MS (Method D): Ret, 15.63 min; ESI$^+$-MS m/z, 322.0 (M+1).

Example 122

2-(2-Methoxyethyl)-1'-phenethyl-3,4-dihydro-2H-spiro[isoquinoline-1,4'-piperidine].

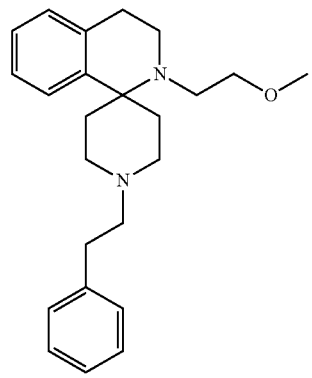 [SMILES: COCCN1CCc2ccccc2C12CCN(CCc1ccccc1)CC2]

LiAlH$_4$ solution (1.0 M in THF, 0.6 mL, 0.60 mmol) was added to a −10° C. cooled solution of 2-methoxy-1-(1'-phenethyl-3,4-dihydro-2H-spiro[isoquinoline-1,4'-piperidine]-2-yl)ethanone (example 5, 230 mg, 0.60 mmol) in THF (10 mL). The reaction mixture was stirred at this temperature for 5 h, allowed to reach r.t. and stirred at this temperature for 15 h. The reaction mixture was cooled down to 0° C., H$_2$O (33 mL), NaOH (15% aqueous solution, 23 mL) and H$_2$O (69 mL) were added and the suspension was stirred at 0° C. for 10 min. The mixture was filtered and rinsed with EtOAc. The filtrate was washed with H$_2$O and the organic layer was dried over Na$_2$SO$_4$, filtered and concentrated. The crude residue was purified by preparative HPLC and slurred with Et$_2$O/hexanes, to give the title compound as a cream solid (81 mg, yield 37%).

HPLC-MS (Method B): Ret, 16.43 min; ESI$^+$-MS m/z, 365.2 (M+1).

Example 123

2-(1'-Phenethyl-3,4-dihydro-2H-spiro[isoquinoline-1,4'-piperidin]-2-yl)ethanol

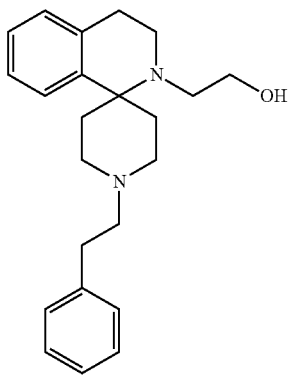 [SMILES: OCCN1CCc2ccccc2C12CCN(CCc1ccccc1)CC2]

HBr (48% aqueous solution, 35 mL, 0.315 mmol) was added to a suspension of 2-(2-methoxyethyl)-1'-phenethyl-3,4-dihydro-2H-spiro[isoquinoline-1,4'-piperidine](example 122, 23 mg, 0.063 mmol) in H$_2$O (200 mL). The reaction mixture was refluxed for 24 h, allowed to reach r.t. and concentrated. The residue was poured into H$_2$O and extracted with DCM. The combined organic layers were dried over Na$_2$SO$_4$, filtered and concentrated. The crude residue was purified by flash chromatography on SiO$_2$ (DCM/MeOH/NH$_4$OH 95:5:1) and slurred with hexanes, to give the title compound as a cream solid (12 mg, yield 50%).

HPLC-MS (Method B): Ret, 13.85 min; ESI$^+$-MS m/z, 351.4 (M+1).

Example 124

2-(2-Methoxyethyl)-1'-(2-(pyridin-3-yl)ethyl)-3,4-dihydro-2H-spiro[isoquinoline-1,4'-piperidine]

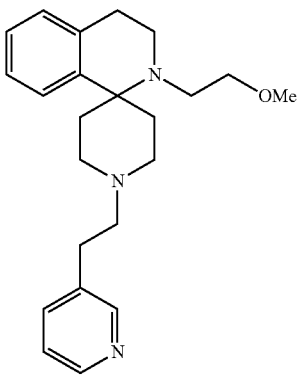 [SMILES: COCCN1CCc2ccccc2C12CCN(CCc1cccnc1)CC2]

a) 2-(2-Methoxyethyl)-3,4-dihydro-2H-spiro[isoquinoline-1,4'-piperidine]

1'-Benzyl-2-(2-methoxyethyl)-3,4-dihydro-2H-spiro[isoquinoline-1,4'-piperidine](intermediate 3D, 181 mg, 0.52 mmol) was added to a suspension of Pd(OH)$_2$ (84 mg, 18.50% Pd, 48.40% H$_2$O w/w, 0.052 mmol) and AcOH (3 µL, 0.052 mmol) in MeOH (10 mL). The suspension was stirred under H$_2$ atmosphere (balloon) for 17 h. The reaction mixture was filtered through Celite, rinsed with MeOH and concentrated to furnish the title compound as a yellow oil (248 mg, quantitative yield).

HPLC-MS (Method E): Ret, 7.88 min; ESI$^+$-MS m/z, 260.8 (M+1).

b) Title Compound

Following a similar procedure to that described in example 65b, but starting from the compound obtained in step a, the title compound was obtained as a white solid.

HPLC-MS (Method E): Ret, 8.80 min; ESI$^+$-MS m/z, 366.3 (M+1).

Example 125

2-[1'-(2-Pyridin-3-yl-ethyl)-3,4-dihydro-spiro[isoquinoline-1,4'-piperidin]-2-yl]-ethanol

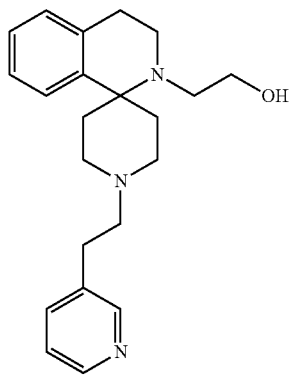 [SMILES: OCCN1CCc2ccccc2C12CCN(CCc1cccnc1)CC2]

Following a similar procedure to that described in example 123 but starting from the compound obtained in example 124 the title compound was obtained as a white solid ((yield 41%).

HPLC-MS (Method E): Ret, 13.88 min; ESI$^+$-MS m/z, 352.3 (M+1).

Example 126

2-(2-(2-Hydroxyethyl)-3,4-dihydro-2H-spiro[isoquinoline-1,4'-piperidine]-1'-yl)-1-(piperidin-1-yl)ethanone

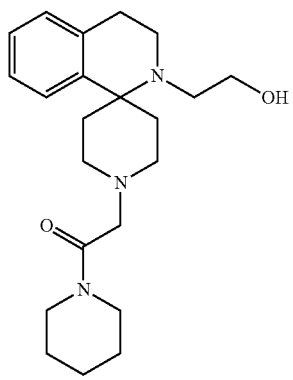 [SMILES: O=C(CN1CCC2(CC1)c1ccccc1CCN2CCO)N1CCCCC1]

a) 2-(3,4-Dihydro-2H-spiro[isoquinoline-1,4'-piperidin]-2-yl)ethanol 2-(1'-benzyl-3,4-dihydro-2H-spiro[isoquinoline-1,4'-piperidin]-2-yl)ethanol (intermediate 3E, 61 mg, 0.18 mmol) was added to a suspension of Pd(OH)$_2$ (30 mg, 20% Pd, 50% H$_2$O w/w) and 2 drops of AcOH in MeOH (2.5 mL). The suspension was stirred under 3 bars of H$_2$ for 18 h. The reaction mixture was filtered through Celite, rinsed with MeOH and concentrated to dryness to furnish the title compound (64 mg, quant yield).

HPLC-MS (Method F): Ret, 2.39 min; ESI$^+$-MS m/z, 247.2 (M+1).

b) Title Compound

2-Chloro-1-(piperidin-1-yl)ethanone (34 mg, 0.21 mmol) was added to a mixture of the compound obtained in step a (44 mg, 0.18 mmol), K$_2$CO$_3$ (74 mg, 0.54 mmol) and NaI (16 mg, 0.11 mmol) in ACN (1 mL). The reaction mixture was stirred under a N$_2$ atmosphere at 80° C. overnight. After cooling down to r.t, it was diluted with water and extracted with EtOAc. The combined organic layers were washed with brine, dried over MgSO$_4$, filtered and concentrated. The crude was purified by flash chromatography on SiO$_2$ (mobile phase: MeOH/DCM mixtures of increasing polarity) to give the title compound (31 mg, 47% yield).

HPLC-MS (Method F): Ret, 3.56 min; ESI+-MS m/z, 372.2 (M+1).

This method was used for the preparation of examples 127-129 starting from the compound obtained in example 126a, and using a suitable alkylating agent.

| EX | Structure | Chemical name | Method | Ret (min) | MS (M + H) |
|---|---|---|---|---|---|
| 127 | 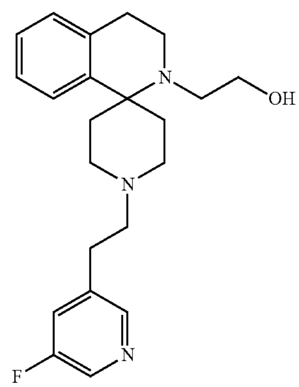 [SMILES: OCCN1CCc2ccccc2C12CCN(CCc1cncc(F)c1)CC2] | 2-(1'-(2-(5-fluoropyridin-3-yl)ethyl)-3,4-dihydro-2H-spiro[isoquinoline-1,4'-piperidin]-2-yl)etanol | F | 3.27 | 370.2 |
| 128 | 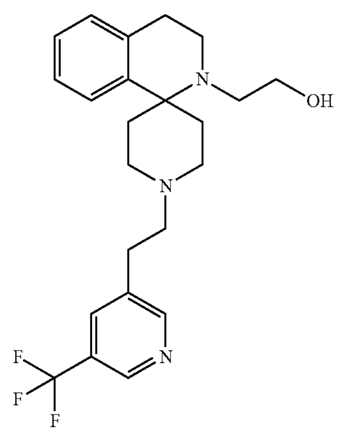 [SMILES: OCCN1CCc2ccccc2C12CCN(CCc1cncc(C(F)(F)F)c1)CC2] | 2-(1'-(2-(5-(trifluoromethyl)pyridin-3-yl)ethyl)-3,4-dihydro-2H-spiro[isoquinoline-1,4'-piperidine]-2-yl)ethanol | F | 3.86 | 420.2 |

| EX | Structure | Chemical name | Method | Ret (min) | MS (M + H) |
|---|---|---|---|---|---|
| 129 | 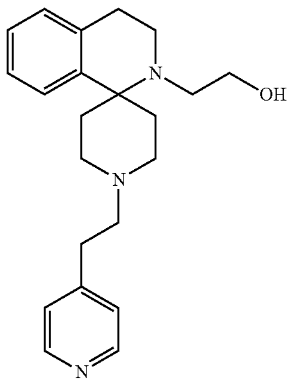 [SMILES: OCCN1CCc2ccccc2C12CCN(CCc1ccncc1)CC2] | 2-(1'-(2-(pyridin-4-yl)ethyl)-3,4-dihydro-2H-spiro[isoquinoline-1,4'-piperidine]-2-yl)ethanol | F | 3.08 | 352.2 |

Example 130

2-(1'-(2-(3-Fluoropyridin-4-yl)ethyl)-3,4-dihydro-2H-spiro[isoquinoline-1,4'-piperidine]-2-yl)ethanol

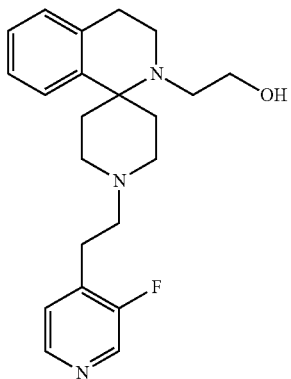 [SMILES: OCCN1CCc2ccccc2C12CCN(CCc1ccncc1F)CC2]

In a sealed tube, 2-(1'-benzyl-3,4-dihydro-2H-spiro[isoquinoline-1,4'-piperidin]-2-yl)ethanol (example 126a, 42 mg, 0.17 mmol) was dissolved in 2-methoxyethanol (1 mL). DIPEA (90 mL, 0.51 mmol) and 3-fluoro-4-vinylpyridine (47 mg, 0.38 mmol) were added and the reaction mixture was heated at 120° C. overnight. The solvent was removed and the crude was purified by flash chromatography on $C_{18}$ (mobile phase: gradient aqueous $NH_4HCO_3$ (pH 8) to ACN) and then by flash chromatography on $SiO_2$ (mobile phase: MeOH/DCM mixtures of increasing polarity) to give the title compound (2.2 mg, 3% yield).

HPLC-MS (Method F): Ret, 3.30 min; ESI$^+$-MS m/z, 370.2 (M+1).

Example 131

2-Methyl-1'-phenethyl-3,4-dihydro-2H-spiro[isoquinoline-1,4'-piperidin]-6-ol

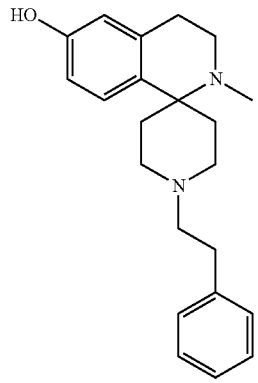 [SMILES: CN1CCc2cc(O)ccc2C12CCN(CCc1ccccc1)CC2]

HBr (1.8 mL, 33% AcOH solution, 31 mmol) was added to a solution of 6-methoxy-2-methyl-1'-phenethyl-3,4-dihydro-2H-spiro[isoquinoline-1,4'-piperidine] (example 55, 400 mg, 1.06 mmol) in AcOH (6 mL) and the reaction mixture was subjected to microwave irradiating conditions for 30 min at 150° C. After cooling the solvent was evaporated under vacuum, and the residue neutralized with $NaHCO_3$ and extracted with ethyl acetate. The combined organic layers were dried over $Na_2SO_4$, filtered and evaporated under vacuum. The crude residue was purified by flash chromatography on $SiO_2$ (Cyclohexane/AcOEt, 85:15) to give the title compound as a yellow solid (46 mg, 12% yield)

HPLC-MS (Method H): Ret, 1.68 min; ESI$^+$-MS m/z, 337.2 (M+1).

Example 132

2,2,2-Trifluoro-1-(1'-phenethyl-3,4-dihydro-2H-spiro[isoquinoline-1,4'-piperidine]-2-yl)ethanone

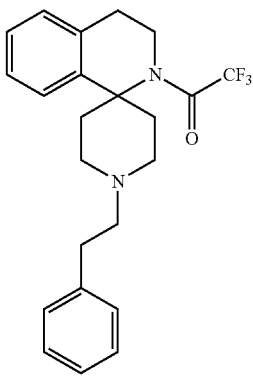 [SMILES: O=C(N1CCc2ccccc2C12CCN(CCc1ccccc1)CC2)C(F)(F)F]

To a solution of 1'-(2-phenylethyl)-3,4-dihydro-2H-spiro[isoquinoline-1,4'-piperidine (intermediate 2C, 112 mg, 0.36 mmol) in DCM (5 mL), trifluoroacetic anhydride (0.510 mL, 3.65 mmol) and pyridine (0.300 mL, 3.65 mmol) were added and the mixture refluxed for 24 h. A saturated solution of $NaHCO_3$ was added, and it was extracted with DCM. The combined organic layers were dried over $MgSO_4$, filtered and evaporated under vacuum to give the title compound (147 mg, quant yield).

HPLC-MS (Method F): Ret, 5.25 min; ESI$^+$-MS m/z, 403.1 (M+1).

Example 133

1'-Phenethyl-2-(2,2,2-trifluoroethyl)-3,4-dihydro-2H-spiro[isoquinoline-1,4'-piperidine]

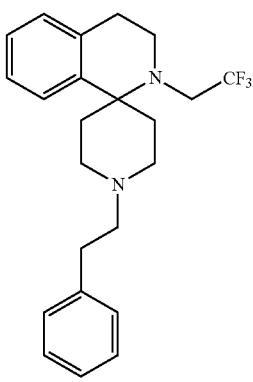 [SMILES: FC(F)(F)CN1CCc2ccccc2C12CCN(CCc1ccccc1)CC2]

Following a similar procedure to that described in example 122, but starting from the compound obtained in example 132 (147 mg, 0.36 mmol), the title compound was obtained (82 mg, 58% yield).

HPLC-MS (Method F): Ret, 5.54 min; ESI+-MS m/z, 389.2 (M+1).

Example 134

1-Morpholino-2-(2-(2,2,2-trifluoroethyl)-3,4-dihydro-2H-spiro[isoquinoline-1,4'-piperidine]-1'-yl)ethanone

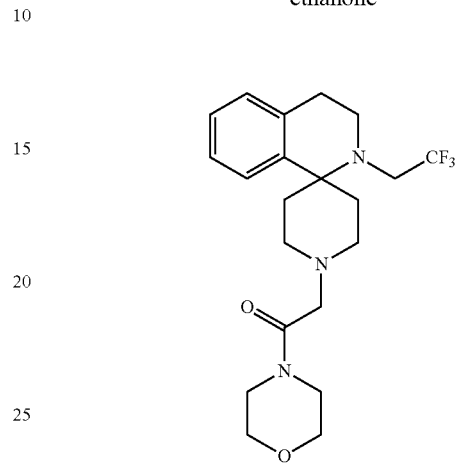

a) 2-(2,2,2-Trifluoroethyl)-3,4-dihydro-2H-spiro[isoquinoline-1,4'-piperidine]

1'-Benzyl-2-(2,2,2-trifluoroethyl)-3,4-dihydro-2H-spiro[isoquinoline-1,4'-piperidine](intermediate 3H, 242 mg, 0.65 mmol) was added to a suspension of Pd(OH)$_2$ (30 mg, 20% Pd, 50% H$_2$O w/w) and 1.25 M HCl solution in EtOH (1 mL, 1.30 mmol) in MeOH (5 mL). The suspension was stirred under 3 bar of H$_2$ for 18 h. The reaction mixture was filtered through Celite, rinsed with MeOH and concentrated to dryness to furnish the title compound (181 mg, 78% yield)

HPLC-MS (Method F): Ret, 3.31 min; ESI+-MS m/z, 285.1 (M+1).

b) Title Compound

Following a similar procedure to that described in example 126b, but starting from the compound obtained in step a (62 mg, 0.17 mmol) and 2-chloro-1-morpholinoethanone (30 mL, 0.21 mmol), 1-morpholino-2-(2-(2,2,2-trifluoroethyl)-3,4-dihydro-2H-spiro[isoquinoline-1,4'-piperidine]-1'-yl)ethanone was obtained (26 mg, 36% yield).

HPLC-MS (Method F): Ret, 4.24 min; ESI+-MS m/z, 412.2 (M+1).

This method was used for the preparation of examples 135-137, starting from the compound obtained in example 134 step a, and using a suitable alkylating agent.

| EX | Structure | Chemical name | Method | Ret (min) | MS (M + H) |
|---|---|---|---|---|---|
| 135 | 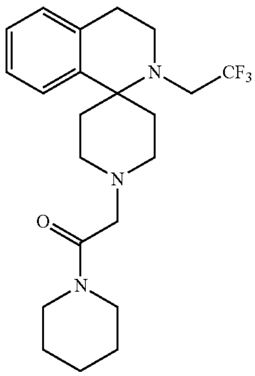 [SMILES: O=C(CN1CCC2(CC1)c1ccccc1CCN2CC(F)(F)F)N1CCCCC1] | 1-(piperidin-1-yl)-2-(2-(2,2,2-trifluoroethyl)-3,4-dihydro-2H-spiro[isoquinoline-1,4'-piperidine]-1'-yl)ethanone | F | 4.88 | 410.2 |
| 136 | 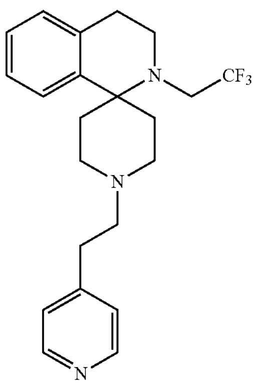 [SMILES: FC(F)(F)CN1CCc2ccccc2C12CCN(CCc1ccncc1)CC2] | 1'-(2-(pyridin-4-yl)ethyl)-2-(2,2,2-trifluoroethyl)-3,4-dihydro-2H-spiro[isoquinoline-1,4'-piperidine] | F | 4.45 | 390.2 |
| 137 | 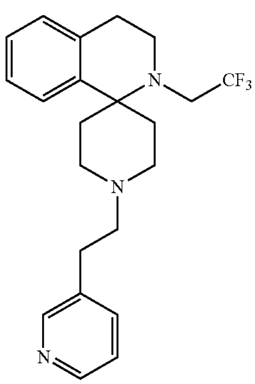 [SMILES: FC(F)(F)CN1CCc2ccccc2C12CCN(CCc1cccnc1)CC2] | 1'-(2-(pyridin-3-yl)ethyl)-2-(2,2,2-trifluoroethyl)-3,4-dihydro-2H-spiro[isoquinoline-1,4'-piperidine] | F | 4.45 | 390.2 |

Example 138

1-(Piperidin-1-yl)-2-(2,4,4-trimethyl-3,4-dihydro-2H-spiro[isoquinoline-1,4'-piperidine]-1'-yl)ethanone

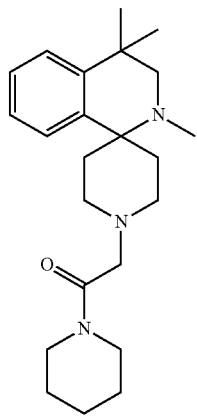 [SMILES: CN1CC(C)(C)c2ccccc2C12CCN(CC(=O)N1CCCCC1)CC2]

a) 2,4,4-Trimethyl-3,4-dihydro-2H-spiro[isoquinoline-1,4'-piperidine]

Following a similar procedure to that described in example 65 step a, but starting from intermediate 3K (147 mg, 0.44 mmol), the title compound was obtained (107 mg, quant yield).

HPLC-MS (Method F): Ret, 3.22 min; ESI$^+$-MS m/z, 254.2 (M+1).

b) Title Compound

Following a similar procedure to that described in example 65 step b, but starting from the compound obtained in step a (107 mg, 0.44 mmol), 1-(piperidin-1-yl)-2-(2,4,4-trimethyl-3,4-dihydro-2H-spiro[isoquinoline-1,4'-piperidine]-1'-yl)ethanone was obtained (109 mg, 67% yield).

HPLC-MS (Method F): Ret, 4.70 min; ESI+-MS m/z, 370.2 (M+1).

Example 139

1-(1'-Phenethylspiro[isoindoline-1,4'-piperidine]-2-yl)ethanone

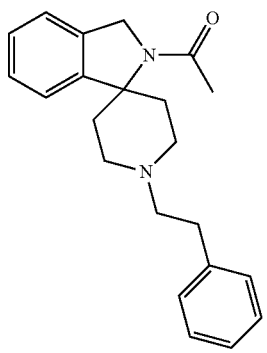 [SMILES: CC(=O)N1Cc2ccccc2C12CCN(CCc1ccccc1)CC2]

a) 1'-(2-Phenylethyl)-2,3-dihydrospiro[isoindole-1,4'-piperidine]

Following a similar procedure to that described in the synthesis of intermediate 2B, but starting from the compound obtained in the synthesis of intermediate 4C step a, the title compound was obtained as an off-white solid (yield 82%).

HPLC-MS (Method B1): Ret, 8.51 min; ESI$^+$-MS m/z, 293.1 (M+1).

b) Title Compound

Following a similar procedure to that described in example 1, but starting from the compound obtained in step a, the title compound was obtained as an off-white solid (yield 65%).

HPLC-MS (Method B): Ret, 16.56 min; ESI$^+$-MS m/z, 335.2 (M+1).

Example 140

2-Methyl-1'-phenethylspiro[isoindoline-1,4'-piperidine]

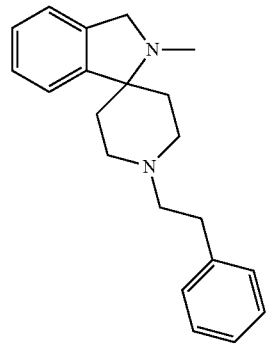 [SMILES: CN1Cc2ccccc2C12CCN(CCc1ccccc1)CC2]

Following a similar procedure to that described in the synthesis of intermediate 3C, but starting from the compound obtained in example 139a, the title compound was obtained as a yellow solid (yield 53%).

HPLC-MS (Method B): Ret, 16.57 min; ESI$^+$-MS m/z, 307.2 (M+1).

Alternatively, the compound of example 140 can be obtained by reduction of intermediate 4C under the conditions described for the preparation of intermediate 2B.

Example 141

2-Methyl-1'-((tetrahydro-2H-pyran-4-yl)methyl)spiro[isoindoline-1,4'-piperidine]

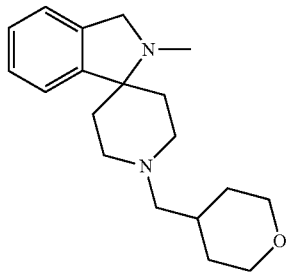 [SMILES: CN1Cc2ccccc2C12CCN(CC1CCOCC1)CC2]

a) 2-Methyl-2,3-dihydrospiro[isoindole-1,4'-piperidine]

Following a similar procedure to that described in the synthesis of intermediate 1D step a, but starting from intermediate 4B, the title compound was obtained as a yellow oil (quantitative yield).
HPLC-MS (Method B1): Ret, 13.06 min; ESI$^+$-MS m/z, 203.1 (M+1).

b) Title Compound

Following a similar procedure to that described in the synthesis of intermediate 3C, but starting from the compound obtained in step a, and using tetrahydro-2H-pyran-4-carbaldehyde instead of formaldehyde, the title compound was obtained as a yellow oil (yield 28%).
HPLC-MS (Method D): Ret, 14.77 min; ESI$^+$-MS m/z, 301.1 (M+1).

Examples 142

(R)-1-(3-fluoropyridin-4-yl)-2-(2-methyl-3,4-dihydro-2H-spiro[isoquinoline-1,4'-piperidine]-1'-yl)ethanol and 143, (S)-1-(3-fluoropyridin-4-yl)-2-(2-methyl-3,4-dihydro-2H-spiro[isoquinoline-1,4'-piperidine]-1'-yl)ethanol

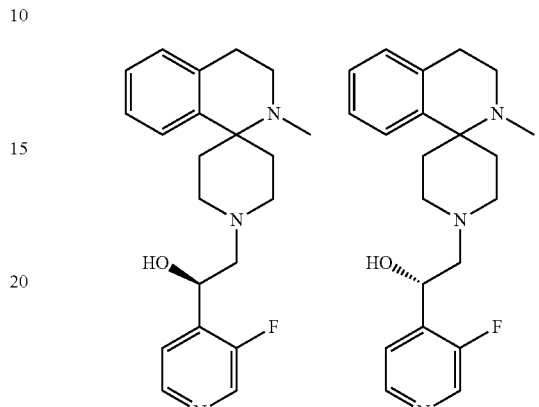

Examples 142 and 143. were obtained by chiral preparative HPLC from example 113: Column: Chiralcel IC; Temperature: ambient; Flow: 10 mL/min; Mobile phase: n-Heptane/(EtOH+0.33% DEA) 90/10 v/v.

Example 142. HPLC-MS (Method H): Ret, 1.75 min; ESI$^+$-MS m/z, 356.3 (M+1).

Example 143. HPLC-MS (Method H): Ret, 1.75 min; ESI$^+$-MS m/z, 356.3 (M+1).

Examples 144, 145 and 146 were prepared according to the procedure described in Example 63, using intermediates 2AV, 2AK and 2AW respectively, as starting materials:

| EX | Structure | Chemical name | Method | Ret (min) | MS (M + H) |
|---|---|---|---|---|---|
| 144 | 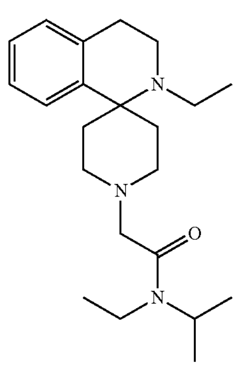 [SMILES: CCN(C(=O)CN1CCC2(CC1)c1ccccc1CCN2CC)C(C)C] | N-ethyl-2-(2-ethyl-3,4-dihydro-2H-spiro[isoquinoline-1,4'-piperidine]-1'-yl)-N-isopropylacetamide | H | 2.16 | 358.3 |

| EX | Structure | Chemical name | Method | Ret (min) | MS (M + H) |
|---|---|---|---|---|---|
| 145 | 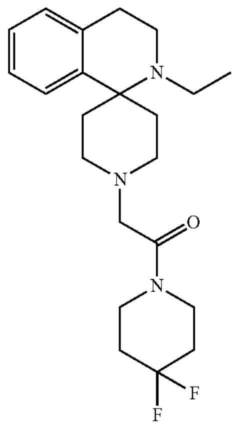 [SMILES: CCN1CCc2ccccc2C12CCN(CC(=O)N1CCC(F)(F)CC1)CC2] | 1-(4,4-difluoropiperidin-1-yl)-2-(2-ethyl-3,4-dihydro-2H-spiro[isoquinoline-1,4'-piperidine]-1'-yl)ethanone | H | 2.05 | 392.3 |
| 146 | 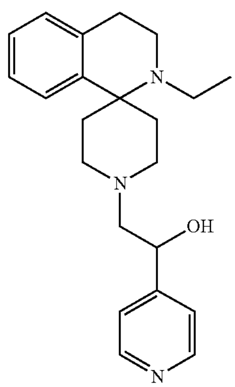 [SMILES: CCN1CCc2ccccc2C12CCN(CC(O)c1ccncc1)CC2] | 2-(2-ethyl-3,4-dihydro-2H-spiro[isoquinoline-1,4'-piperidine]-1'-yl)-1-(pyridin-4-yl)ethanol | H | 1.72 | 352.3 |

Examples 147 to 155 were prepared according to the procedure described in Example 65, using intermediate 3L as starting material in step a and suitable alkylating agents in step b.

| EX | Structure | Chemical name | Method | Ret (min) | MS (M + H) |
|---|---|---|---|---|---|
| 147 | 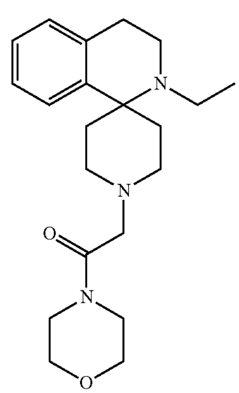 [SMILES: CCN1CCc2ccccc2C12CCN(CC(=O)N1CCOCC1)CC2] | 2-(2-ethyl-3,4-dihydro-2H-spiro[isoquinoline-1,4'-piperidine]-1'-yl)-1-morpholinoethanone | H | 1.67 | 358.2 |

| EX | Structure | Chemical name | Method | Ret (min) | MS (M + H) |
|---|---|---|---|---|---|
| 148 | 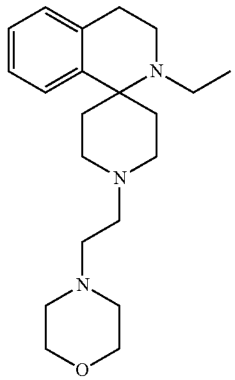 [SMILES: CCN1CCc2ccccc2C12CCN(CCN1CCOCC1)CC2] | 4-(2-(2-ethyl-3,4-dihydro-2H-spiro[isoquinoline-1,4'-piperidine]-1'-yl)ethyl)morpholine | H | 1.6 | 344.2 |
| 149 | 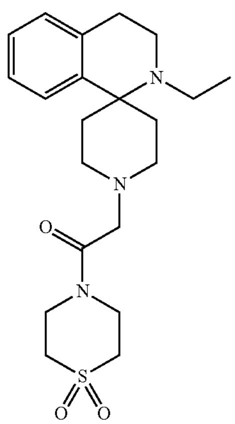 [SMILES: CCN1CCc2ccccc2C12CCN(CC(=O)N1CCS(=O)(=O)CC1)CC2] | 2-(2-ethyl-3,4-dihydro-2H-spiro[isoquinoline-1,4'-piperidine]-1'-yl)-1-(1,1-dioxo-thiomorpholin-4-yl)ethanone | H | 1.9 | 406.3 |
| 150 | 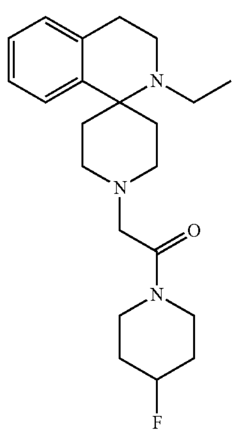 [SMILES: CCN1CCc2ccccc2C12CCN(CC(=O)N1CCC(F)CC1)CC2] | 2-(2-ethyl-3,4-dihydro-2H-spiro[isoquinoline-1,4'-piperidine]-1'-yl)-1-(4-fluoropiperidin-1-yl)ethanone | H | 2.2 | 374.3 |

-continued

| EX | Structure | Chemical name | Method | Ret (min) | MS (M + H) |
|---|---|---|---|---|---|
| 151 | 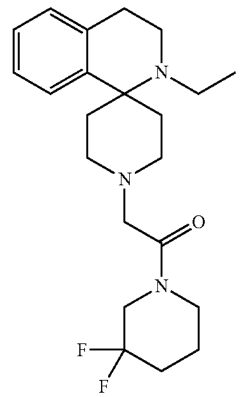 [SMILES: CCN1CCc2ccccc2C12CCN(CC(=O)N1CCCC(F)(F)C1)CC2] | 1-(3,3-difluoropiperidin-1-yl)-2-(2-ethyl-3,4-dihydro-2H-spiro[isoquinoline-1,4'-piperidine]-1'-yl)ethanone | H | 2.48 | 392.3 |
| 152 | 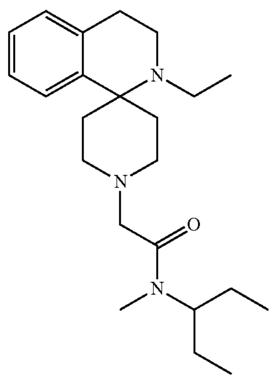 [SMILES: CCC(CC)N(C)C(=O)CN1CCC2(CC1)c1ccccc1CCN2CC] | 2-(2-ethyl-3,4-dihydro-2H-spiro[isoquinoline-1,4'-piperidine]-1'-yl)-N-methyl-N-(pentan-3-yl)acetamide | H | 2.25 | 372.2 |
| 153 | 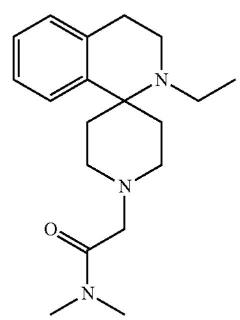 [SMILES: CCN1CCc2ccccc2C12CCN(CC(=O)N(C)C)CC2] | 2-(2-ethyl-3,4-dihydro-2H-spiro[isoquinoline-1,4'-piperidine]-1'-yl)-N,N-dimethylacetamide | H | 1.6 | 316.2 |
| 154 | 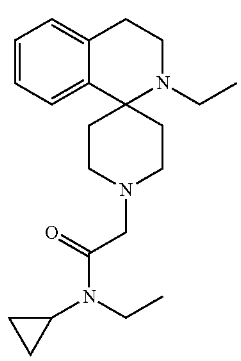 [SMILES: CCN(C(=O)CN1CCC2(CC1)c1ccccc1CCN2CC)C1CC1] | N-cyclopropyl-N-ethyl-2-(2-ethyl-3,4-dihydro-2H-spiro[isoquinoline-1,4'-piperidine]-1'-yl)acetamide | H | 1.91 | 356.3 |

| EX | Structure | Chemical name | Method | Ret (min) | MS (M + H) |
|---|---|---|---|---|---|
| 155 | 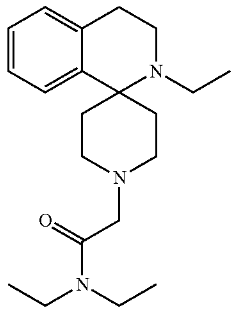 [SMILES: CCN(CC)C(=O)CN1CCC2(CC1)c1ccccc1CCN2CC] | N,N-diethyl-2-(2-ethyl-3,4-dihydro-2H-spiro[isoquinoline-1,4'-piperidine]-1'-yl)acetamide | H | 2.32 | 344.3 |

Examples 156 and 157 were prepared according to the alkylation procedure described in Example 65 step b, using the compound obtained in example 141 step a as starting material and suitable alkylating agents.

| EX | Structure | Chemical name | Method | Ret (min) | MS (M + H) |
|---|---|---|---|---|---|
| 156 | 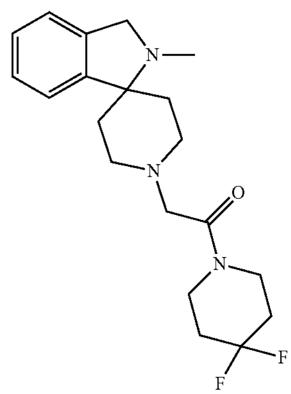 [SMILES: CN1Cc2ccccc2C12CCN(CC(=O)N1CCC(F)(F)CC1)CC2] | 1-(4,4-difluoropiperidin-1-yl)-2-(2-methylspiro[isoindoline-1,4'-piperidine]-1'-yl)ethanone | E | 15.6 | 364 |
| 157 | 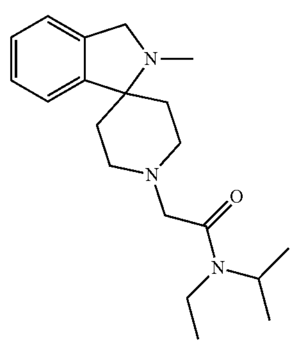 [SMILES: CCN(C(=O)CN1CCC2(CC1)c1ccccc1CN2C)C(C)C] | N-ethyl-N-isopropyl-2-(2-methylspiro[isoindoline-1,4'-piperidine]-1'-yl)acetamide | E | 16.2 | 330.3 |

Example 158

N-ethyl-1'-(2-(pyridin-4-yl)ethyl)-3,4-dihydro-2H-spiro[isoquinoline-1,4'-piperidine]-2-carboxamide

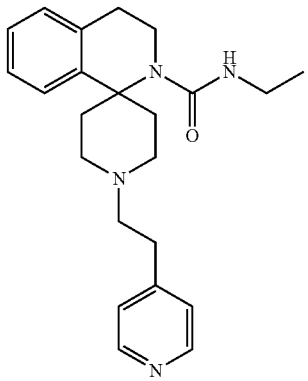 [SMILES: CCNC(=O)N1CCc2ccccc2C12CCN(CCc1ccncc1)CC2]

Triethylamine (0.095 mL, 0.68 mmol) and ethyl isocyanate (0.027 mL, 0.34 mmol) were added to a solution of 1'-(2-(pyridin-4-yl)ethyl)-3,4-dihydro-2H-spiro[isoquinoline-1,4'-piperidine] (intermediate 2W, 70 mg, 0.23 mmol) in DCM (2 mL), previously cooled at 0° C. The reaction was stirred at room temperature overnight. Additional triethylamine and ethyl isocyanate were added and the mixture stirred at room temperature overnight. This procedure was repeated until full conversion was achieved. It was then concentrated to dryness. The crude residue was purified by flash chromatography on $C_{18}$ (mobile phase: gradient aqueous $NH_4HCO_3$ (pH 8) to acetonitrile) to give the title compound as a white solid (14 mg, yield 16%).

HPLC-MS (Method I): Ret, 3.06 min; ESI+-MS m/z, 379.2 (M+1).

Example 159

1'-(2-(Pyrimidin-5-yl)ethyl)-2-(2,2,2-trifluoroethyl)-3,4-dihydro-2H-spiro[isoquinoline-1,4'-piperidine]

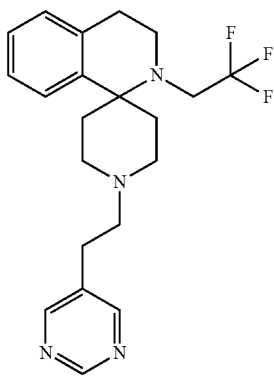 [SMILES: FC(F)(F)CN1CCc2ccccc2C12CCN(CCc1cncnc1)CC2]

The title compound was prepared according to the procedure described in Example 134.

HPLC-MS (Method F): Ret, 4.28 min; ESI⁺-MS m/z, 392.2 (M+1).

Example 160

2-(2-(2-Methyl-3,4-dihydro-2H-spiro[isoquinoline-1,4'-piperidine]-1'-yl)ethylamino)ethanol

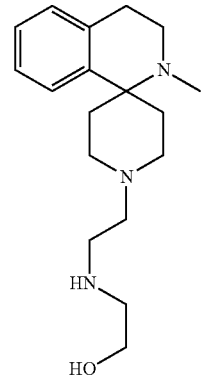 [SMILES: CN1CCc2ccccc2C12CCN(CCNCCO)CC2]

2-Methyl-3,4-dihydro-2H-spiro[isoquinoline-1,4'-piperidine] (compound obtained in example 65 step a, 268 mg, 1.23 mmol) and 2-(aziridin-1-yl)ethanol (43 µL, 0.49 mmol) were dissolved in dichloromethane in a process vial. The reaction was stirred for few minutes and then the solvent was removed with a stream of nitrogen. Amberlyst (6 mg) was added, the vial was sealed with a septum and the reaction mixture was subjected to microwave irradiation for 3 h at 100° C. After cooling back to r.t., the reaction was diluted with dichloromethane, and $NaHCO_3$ was added. The phases were separated and the aqueous phase additionally extracted with DCM. The aqueous phase was then basified with NaOH solution and again extracted twice with DCM. The combined organic fractions were dried over sodium sulphate, filtered and the solvent removed to give a crude product which was purified under preparative HPLC (Column X-Bridge C18, H2O+ 0.05% formic acid: ACN+0.05% formic acid from (98:2 to 5:95), flow 20 ml/min, rt).

HPLC-MS (Method H): Ret, 1.23 min; ESI⁺-MS m/z, 304.2 (M+1).

Table of Examples with Binding to the µ-Opioid Receptor and the □ σ1-Receptor

Biological Activity

Pharmacological Study

Human $\sigma_1$ Receptor Radioligand Assay

To investigate binding properties of test compounds to human $\sigma_1$ receptor, transfected HEK-293 membranes and [³H](+)-pentazocine (Perkin Elmer, NET-1056), as the radioligand, were used. The assay was carried out with 7 µg of membrane suspension, 5 nM of [³H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-Opioid Receptor Radioligand Assay To investigate binding properties of test compounds to human mu-opioid receptor, transfected CHO-K1 cell membranes and [³H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the μ-opiod receptor expressed as $K_i$:
+ Both $K_i$-μ and $K_i$-$\sigma_1$ >=500 nM
++ One $K_i$<500 nM while the other $K_i$ is >=500 nM
+++ Both $K_i$-μ and $K_i$-$\sigma_1$<500 nM
++++ Both $K_i$-μ and $K_i$-$\sigma_1$<100 nM All compounds prepared in the present application exhibit binding to the $\sigma_1$ receptor and the μ-opiod receptor, in particular the following binding results are shown:

| EX | μ and $\sigma_1$ dual binding |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | ++ |
| 10 | ++++ |
| 11 | +++ |
| 12 | ++ |
| 13 | +++ |
| 14 | + |
| 15 | +++ |
| 16 | +++ |
| 17 | ++ |
| 18 | ++ |
| 19 | +++ |
| 20 | ++ |
| 21 | +++ |
| 22 | + |
| 23 | ++ |
| 24 | ++ |
| 25 | +++ |
| 26 | +++ |
| 27 | +++ |
| 28 | +++ |
| 29 | +++ |
| 30 | +++ |
| 31 | +++ |
| 32 | ++ |
| 33 | + |
| 34 | + |
| 35 | ++ |
| 36 | +++ |
| 37 | + |
| 38 | +++ |
| 39 | + |
| 40 | ++ |
| 41 | + |
| 42 | ++ |
| 43 | ++ |
| 44 | ++ |
| 45 | ++ |
| 46 | + |
| 47 | + |
| 48 | ++ |
| 49 | + |
| 50 | + |
| 51 | ++++ |
| 52 | ++ |
| 53 | ++++ |
| 54 | ++++ |
| 55 | ++++ |
| 56 | +++ |
| 57 | ++ |
| 58 | +++ |
| 59 | + |
| 60 | ++ |
| 61 | +++ |
| 62 | ++++ |
| 63 | ++++ |
| 64 | +++ |
| 65 | +++ |
| 66 | +++ |
| 67 | ++ |
| 68 | +++ |
| 69 | +++ |
| 70 | +++ |
| 71 | +++ |
| 72 | ++ |
| 73 | ++ |
| 74 | +++ |
| 75 | +++ |
| 76 | +++ |
| 77 | ++ |
| 78 | +++ |
| 79 | +++ |
| 80 | + |
| 81 | ++ |
| 82 | +++ |
| 83 | ++ |
| 84 | +++ |
| 85 | + |
| 86 | ++ |
| 87 | ++ |
| 88 | ++ |
| 89 | +++ |
| 90 | ++ |
| 91 | +++ |
| 92 | ++ |
| 93 | ++++ |
| 94 | ++ |
| 95 | ++ |
| 96 | ++ |
| 97 | ++ |
| 98 | +++ |
| 99 | +++ |
| 100 | +++ |
| 101 | +++ |
| 102 | ++ |
| 103 | +++ |
| 104 | ++ |
| 105 | ++ |
| 106 | +++ |
| 107 | ++ |
| 108 | ++ |
| 109 | ++ |
| 110 | + |
| 111 | +++ |
| 112 | +++ |
| 113 | +++ |
| 114 | +++ |
| 115 | + |

-continued

| EX | μ and σ₁ dual binding |
|---|---|
| 116 | ++ |
| 117 | ++++ |
| 118 | ++++ |
| 119 | +++ |
| 120 | +++ |
| 121 | +++ |
| 122 | +++ |
| 123 | ++++ |
| 124 | + |
| 125 | +++ |
| 126 | ++ |
| 127 | +++ |
| 128 | +++ |
| 129 | ++ |
| 130 | +++ |
| 131 | ++++ |
| 132 | + |
| 133 | ++++ |
| 134 | ++ |
| 135 | ++ |
| 136 | +++ |
| 137 | +++ |
| 138 | + |
| 139 | ++ |
| 140 | +++ |
| 141 | ++ |
| 142 | +++ |
| 143 | +++ |
| 144 | +++ |
| 145 | +++ |
| 146 | ++ |
| 147 | +++ |
| 148 | ++ |
| 149 | ++ |
| 150 | +++ |
| 151 | +++ |
| 152 | ++ |
| 153 | ++ |
| 154 | +++ |
| 155 | +++ |
| 156 | + |
| 157 | + |
| 158 | ++ |
| 159 | ++ |
| 160 | + |

The invention claimed is:
1. A compound of general formula (I):

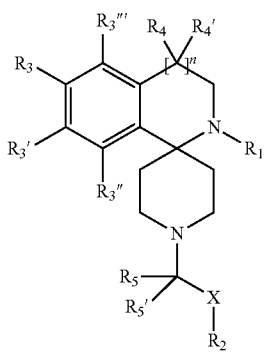

(I)

wherein
n is 0 or 1
$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, —C(O)$R_6$, —C(O)CH$_2$O$R_6$, —C(O)CH$_2$OC(O)$R_6$, —C(O)O$R_6$, —C(O)NR$_6$R$_{6'}$ or —S(O)$_2$R$_6$;
wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, substituted or unsubstituted heterocyclyl and substituted or unsubstituted alkyheterocylcyl;
$R_2$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
wherein the alkyl, alkylene or alkynyl in $R_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;
and wherein $R_{12}$ is selected from hydrogen, unsubstituted $C_{1-6}$ alkyl, and unsubstituted $C_{2-6}$ alkenyl, unsubstituted $C_{2-6}$ alkynyl;
X is selected from —CR$_x$R$_{x'}$—, —CR$_x$OR$_{14'}$, —CR$_x$R$_x$NR$_7$—, —CR$_x$R$_x$O—, —CR$_x$R$_x$NR$_7$C(O)—, —C(O)—, —CR$_x$R$_x$C(O)—, —C(O)O—, —C(O)NR$_7$—, —CR$_x$R$_x$C(O)NR$_7$— and —C(O)NR$_7$CR$_x$R$_{x'}$—;
wherein $R_7$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and Boc;
$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_{14'}$, —C(O)NR$_{14}$R$_{14'}$, —NR$_{14}$C(O)R$_{14'}$, and —NR$_{14}$R$_{14'''}$;
$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
alternatively if X is —CR$_x$R$_{x'}$—, $R_x$ and $R_{x'}$ may form, together with the carbon atom to which they are attached, a substituted or unsubstituted heterocyclyl, or a substituted or unsubstituted cycloalkyl;
$R_{14}$ and $R_{14'}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ is selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$R$_{9'''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$R$_{9'''}$, —OCOR$_9$, and C(CH$_3$)$_2$OR$_9$;
$R_{3'}$, $R_{3''}$ and $R_{3'''}$ are independently selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$,R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_9$,R$_{9''}$, —OCOR$_9$, and C(CH$_3$)$_2$OR$_9$;
    wherein R$_9$, R$_{9'}$ and R$_{9''}$ are independently selected from hydrogen, unsubstituted C$_{1-6}$ alkyl, unsubstituted C$_{2-6}$ alkenyl, unsubstituted C$_{2-6}$ alkynyl, and unsubstituted acetyl;
    and wherein R$_{9'''}$ is selected from hydrogen, unsubstituted C$_{1-6}$ alkyl, unsubstituted C$_{2-6}$ alkenyl, unsubstituted C$_{2-6}$ alkynyl and -Boc;
R$_4$ is selected from hydrogen, —OR$_{13}$, substituted or unsubstituted C$_{1-6}$ alkyl, substituted or unsubstituted C$_{2-6}$ alkenyl, substituted or unsubstituted C$_{2-6}$ alkynyl, —C(O)OR$_{13}$, —C(O)NR$_{13}$R$_{13'}$, —NR$_{13}$C(O)R$_{13'}$, —NR$_{13}$R$_{13''''}$, —NC(O)OR$_{13}$, and substituted or unsubstituted heterocyclyl;
R$_{4'}$, is selected from hydrogen, or substituted or unsubstituted C$_{1-6}$ alkyl, substituted or unsubstituted C$_{2-6}$ alkenyl, and substituted or unsubstituted C$_{2-6}$ alkynyl;
    wherein R$_{13}$, R$_{13'}$ and R$_{13''''}$ are independently selected from hydrogen, unsubstituted C$_{1-6}$ alkyl, unsubstituted C$_{2-6}$ alkenyl, and unsubstituted C$_{2-6}$ alkynyl;
    and wherein R$_{13''''}$ is selected from hydrogen, unsubstituted C$_{1-6}$ alkyl, unsubstituted C$_{2-6}$ alkenyl, unsubstituted C$_{2-6}$ alkynyl and -Boc;
R$_5$ and R$_{5'}$ are independently selected from hydrogen, or substituted or unsubstituted C$_{1-6}$ alkyl, substituted or unsubstituted C$_{2-6}$ alkenyl, and substituted or unsubstituted C$_{2-6}$ alkynyl;
optionally as a stereoisomer, a racemate, or in the form of a mixture of at least two of the stereoisomers, preferably stereoisomers, in any mixing ratio, or a corresponding salt thereof, or a corresponding solvate thereof.

2. The compound according to claim 1, wherein R$_1$ is —C(O)R$_6$ or —S(O)$_2$R$_6$.

3. The compound according to claim 1, wherein R$_1$ is substituted or unsubstituted C$_{1-6}$ alkyl.

4. The compound according to claim 1, wherein X is selected from —CR$_x$R$_x$,NR$_7$—, —CR$_x$R$_x$,NR$_7$C(O)—, —C(O)—, —C(O)O—, —C(O)NR$_7$—, —CH$_2$C(O)NR$_7$—, —CR$_x$R$_x$,O—, and —C(O)NR$_7$CRxR$_{x'}$.

5. The compound according to claim 1, wherein X is, —CR$_x$R$_{x'}$, —CR$_x$OR$_{14'}$, —CR$_x$R$_{x'}$ NR$_7$—, or CR$_x$R$_x$,O—, and
R$_1$ is —C(O)R$_6$ or —S(O)$_2$R$_6$.

6. The compound according to claim 1, wherein X is —CR$_x$R$_{x'}$, —CR$_x$OR$_{14'}$, —CR$_x$R$_x$,NR$_7$—, or CR$_x$R$_x$,O—, and
R$_1$ is substituted or unsubstituted C$_{1-6}$ alkyl, substituted or unsubstituted C$_{2-6}$ alkenyl, substituted or unsubstituted C$_{2-6}$ alkynyl.

7. The compound according to claim 1, wherein X is —CR$_x$R$_{x'}$, —CR$_x$OR$_{14'}$, —CR$_x$R$_x$,NR$_7$—, or CR$_x$R$_x$,O—, and
R$_1$ is substituted or unsubstituted alkylaryl, substituted or unsubstituted alkylheterocyclyl, substituted or unsubstituted alkylcycloalkyl.

8. The compound according to claim 1, wherein X is —C(O)NR$_7$—, and
R$_1$ is substituted or unsubstituted C$_{1-6}$ alkyl, substituted or unsubstituted C$_{2-6}$ alkenyl, substituted or unsubstituted C$_{2-6}$ alkynyl.

9. The compound according to claim 1, wherein
X is —C(O)—,
R$_1$ is substituted or unsubstituted C$_{1-6}$ alkyl, substituted or unsubstituted C$_{2-6}$ alkenyl, substituted or unsubstituted C$_{2-6}$ alkynyl, and
R$_2$ is substituted or unsubstituted heterocyclyl, wherein the heterocyclyl contains, at least, one nitrogen attached to the carbonyl group in X.

10. The compound according to claim 9, wherein R$_1$ is —C(O)R$_6$ or —S(O)$_2$R$_6$.

11. The compound according to claim 1, which is selected from:
1-(1'-phenethyl-3,4-dihydro-2H-spiro[isoquinoline-1,4'-piperidine]-2-yl)ethanone,
2-methyl-1-(1'-phenethyl-3,4-dihydro-2H-spiro[isoquinoline-1,4'-piperidine]-2-yl)propan-1-one,
furan-2-yl(1'-phenethyl-3,4-dihydro-2H-spiro[isoquinoline-1,4'-piperidine]-2-yl)methanone,
1-(1'-phenethyl-3,4-dihydro-2H-spiro[isoquinoline-1,4'-piperidine]-2-yl)propan-1-one,
2-methoxy-1-(1'-phenethyl-3,4-dihydro-2H-spiro[isoquinoline-1,4'-piperidine]-2-yl)ethanone,
2-(benzyloxy)-1-(1'-phenethyl-3,4-dihydro-2H-spiro[isoquinoline-1,4'-piperidine]-2-yl)ethanone,
1-(6-methoxy-1'-phenethyl-3,4-dihydro-2H-spiro[isoquinoline-1,4'-piperidine]-2-yl)ethanone,
1-(1'-(2-morpholinoethyl)-3,4-dihydro-2H-spiro[isoquinoline-1,4'-piperidine]-2-yl)ethanone,
1-(1'-((tetrahydro-2H-pyran-4-yl)methyl)-3,4-dihydro-2H-spiro[isoquinoline-1,4'-piperidine]-2-yl)ethanone,
1-(1'-(2-(methyl(phenyl)amino)ethyl)-3,4-dihydro-2H-spiro[isoquinoline-1,4'-piperidine]-2-yl)ethanone,
1-(1'-(2-isopropoxyethyl)-3,4-dihydro-2H-spiro[isoquinoline-1,4'-piperidine]-2-yl)ethanone,
1-(1'-isobutyl-3,4-dihydro-2H-spiro[isoquinoline-1,4'-piperidine]-2-yl)ethanone
1-(1'-(cyclohexylmethyl)-3,4-dihydro-2H-spiro[isoquinoline-1,4'-piperidine]-2-yl)ethanone,
1-(1'-(2-(piperidin-1-yl)ethyl)-3,4-dihydro-2H-spiro[isoquinoline-1, 4'-piperidine]-2-yl)ethanone,
1-(1'-isopentyl-3,4-dihydro-2H-spiro[isoquinoline-1,4'-piperidine]-2-yl)ethanone,
1-(1'-(2-(benzyl(methyl)amino)ethyl)-3,4-dihydro-2H-spiro[isoquinoline-1,4'-piperidine]-2-yl)ethanone,
1-(1'-(pyridin-2-ylmethyl)-3,4-dihydro-2H-spiro[isoquinoline-1,4'-piperidine]-2-yl)ethanone,
1-(1'-(2-(pyridin-2-yl)ethyl)-3,4-dihydro-2H-spiro[isoquinoline-1,4'-piperidine]-2-yl)ethanone,
1-(1'-(2-(pyridin-3-yl)ethyl)-3,4-dihydro-2H-spiro[isoquinoline-1,4'-piperidine]-2-yl)ethanone,
1-(1'-(2-phenoxyethyl)-3,4-dihydro-2H-spiro[isoquinoline-1,4'-piperidine]-2-yl)ethanone,
1-(1'-(2-(pyridin-4-yl)ethyl)-3,4-dihydro-2H-spiro[isoquinoline-1,4'-piperidine]-2-yl)ethanone,
3-(2-acetyl-3,4-dihydro-2H-spiro[isoquinoline-1,4'-piperidine]-1'-yl)-N,N-dimethylpropanamide,
1-(1'-(2-(6-(trifluoromethyl)pyridin-3-yl)ethyl)-3,4-dihydro-2H-spiro[isoquinoline-1,4'-piperidine]-2-yl)ethanone,
1-(1'-(2-ethoxyethyl)-3,4-dihydro-2H-spiro[isoquinoline-1,4'-piperidine]-2-yl)ethanone,
1-(1'-(2-(2-(trifluoromethyl)pyridin-4-yl)ethyl)-3,4-dihydro-2H-spiro[isoquinoline-1,4'-piperidine]-2-yl)ethanone,
1-(1'-(2-(3-fluoropyridin-4-yl)ethyl)-3,4-dihydro-2H-spiro[isoquinoline-1,4'-piperidine]-2-yl)ethanone, 1-(1'-(2-(5-chloropyridin-3-yl)ethyl)-3,4-dihydro-2H-spiro[isoquinoline-1,4'-piperidine]-2-yl)ethanone,
4-(2-(2-acetyl-3,4-dihydro-2H-spiro[isoquinoline-1,4'-piperidine]-1'-yl)ethyl)picolinonitrile,
1-(1'-(2-(5-fluoropyridin-3-yl)ethyl)-3,4-dihydro-2H-spiro[isoquinoline-1,4'-piperidine]-2-yl)ethanone,
1-(1'-(2-(cyclopropymethoxy)ethyl)-3,4-dihydro-2H-spiro[isoquinoline-1,4'-piperidine]-2-yl)ethanone,
1-(1'-(2-isobutoxyethyl)-3,4-dihydro-2H-spiro[isoquinoline-1,4'-piperidine]-2-yl)ethanone,
1-(1'-(2-(benzyloxy)ethyl)-3,4-dihydro-2H-spiro[isoquinoline-1,4'-piperidine]-2-yl)ethanone,
1-(1'-(cyclopropylmethyl)-3,4-dihydro-2H-spiro[isoquinoline-1,4'-piperidine]-2-yl)ethanone,
2-(2-acetyl-3,4-dihydro-2H-spiro[isoquinoline-1,4'-piperidine]-1'-yl)-1-morpholinoethanone,
3-(2-acetyl-3,4-dihydro-2H-spiro[isoquinoline-1,4'-piperidine]-1'-yl)-N-methyl-N-phenylpropanamide,
1-(1'-(3-(trifluoromethoxy)phenethyl)-3,4-dihydro-2H-spiro[isoquinoline-1,4'-piperidine]-2-yl)ethanone,
tert-butyl 2-(2-acetyl-3,4-dihydro-2H-spiro[isoquinoline-1,4'-piperidine]-1'-yl)ethylcarbamate,
N-(3-(2(2-acetyl-3,4-dihydro-2H-spiro[isoquinoline-1,4'-piperidine]-1'-yl)ethyl)phenyl)acetamide,
2-(2-acetyl-3,4-dihydro-2H-spiro[isoquinoline-1,4'-piperidine]-1'-yl)-1-phenylethyl acetate,
1-(1'-(2-hydroxy-2-phenylethyl)-3,4-dihydro-2H-spiro[isoquinoline-1,4'-piperidine]-2-yl)ethanone,
1-(1'-(2-hydroxyethyl)-3,4-dihydro-2H-spiro[isoquinoline-1,4'-piperidine]-2-yl)ethanone,
1-(1'-(2-(pyridin-2-yloxy)ethyl)-3,4-dihydro-2H-spiro[isoquinoline-1,4'-piperidine]-2-yl)ethanone,
1-(1'-(2-(pyridin-3-yloxy)ethyl)-3,4-dihydro-2H-spiro[isoquinoline-1,4'-piperidine]-2-yl)ethanone,
1-(1'-(2-(pyridin-4-yloxy)ethyl)-3,4-dihydro-2H-spiro[isoquinoline-1,4'-piperidine]-2-yl)ethanone,
N-(4-(2-(2-acetyl-3,4-dihydro-2H-spiro[isoquinoline-1,4'-piperidine]-1'-yl)ethyl)pyridin-2-yl)acetamide,
tert-butyl 2-(2-acetyl-3,4-dihydro-2H-spiro[isoquinoline-1,4'-piperidine]-1'-yl)ethyl(methyl)carbamate,
1-(1'-(2-(methylamino)ethyl)-3,4-dihydro-2H-spiro[isoquinoline-1,4'-piperidine]-2-yl)ethanone,
N-(2-(2-acetyl-3,4-dihydro-2H-spiro[isoquinoline-1,4'-piperidine]-1'-yl)ethyl)-N-methylbenzamide,
2-acetyl-1'-phenethyl-3,4-dihydro-2H-spiro[isoquinoline-1,4'-piperidine]-6-yl acetate,
1-(6-hydroxy-1'-phenethyl-3,4-dihydro-2H-spiro[isoquinoline-1,4'-piperidine]-2-yl)ethanone,
1-(6-chloro-1'-phenethyl-3,4-dihydro-2H-spiro[isoquinoline-1,4'-piperidine]-2-yl)ethanone,
2-hydroxy-1-(1'-phenethyl-3,4-dihydro-2H-spiro[isoquinoline-1,4'-piperidine]-2-yl)ethanone,
2-(methylsulfonyl)-1'-phenethyl-3,4-dihydro-2H-spiro[isoquinoline-1,4'-piperidine],
2-methyl-1'-phenethyl-3,4-dihydro-2H-spiro[isoquinoline-1,4'-piperidine],
6-methoxy-2-methyl-1'-phenethyl-3,4-dihydro-2H-spiro[isoquinoline-1,4'-piperidine],
N,N-diethyl-2-(2-methyl-3,4-dihydro-2H-spiro[isoquinoline-1,4'-piperidine]-1'-yl)acetamide,
2-(2-methyl-3,4-dihydro-2H-spiro[isoquinoline-1,4'-piperidine]-1-yl)-1-(1,4-oxazepan-4-yl)ethanone,
1-(4-fluoropiperidin-1-yl)-2-(2-methyl-3,4-dihydro-2H-spiro[isoquinoline-1,4'-piperidine]-1'-yl)ethanone,
1-(4-(2-hydroxypropan-2-yl)piperidin-1-yl)-2-(2-methyl-3,4-dihydro-2H-spiro[isoquinoline-1,4'-piperidine]-1'-yl)ethanone,
1-(4-methoxypiperidin-1-yl)-2-(2-methyl-3,4-dihydro-2H-spiro[isoquinoline-1,4'-piperidine]-1'-yl)ethanone,
1-(4,4-difluoropiperidin-1-yl)-2-(2-methyl-3,4-dihydro-2H-spiro[isoquinoline-1,4'-piperidine]-1'-yl)ethanone,
2-(2-methyl-3,4-dihydro-2H-spiro[isoquinoline-1,4'-piperidine]-1'-yl)-1-(6-azaspiro[2.5]octan-6-yl)ethanone,
2-ethyl-1'-phenethyl-3,4-dihydro-2H-spiro[isoquinoline-1,4'-piperidine],
2-((1'-phenethyl-3,4-dihydro-2H-spiro[isoquinoline-1,4'-piperidine]-2-yl)methyl)thiazole,
4-(2-(2-methyl-3,4-dihydro-2H-spiro[isoquinoline-1,4'-piperidine]-1'-yl)ethyl)morpholine,
1'-(cyclohexylmethyl)-2-methyl-3,4-dihydro-2H-spiro[isoquinoline-1,4'-piperidine],
2-methyl-1'-((tetrahydro-2H-pyran-4-yl)methyl)-3,4-dihydro-2H-spiro[isoquinoline-1,4'-piperidine],
N,N-dimethyl-3-(2-methyl-3,4-dihydro-2H-spiro[isoquinoline-1,4'-piperidine]-1'-yl)propanamide,
2-(2-methyl-3,4-dihydro-2H-spiro[isoquinoline-1,4'-piperidine]-1'-yl)-1-phenylethanone,
2-(2-methyl-3,4-dihydro-2H-spiro[isoquinoline-1,4'-piperidine]-1'-yl)-1-morpholinoethanone,
2-(2-methyl-3,4-dihydro-2H-spiro[isoquinoline-1,4'-piperidine]-1'-yl)-1-(piperidin-1-yl)ethanone,
N-methyl-2-(2-methyl-3,4-dihydro-2H-spiro[isoquinoline-1,4'-piperidine]-1'-yl)-N-phenylacetamide,
N,N-dimethyl-2-(2-methyl-3,4-dihydro-2H-spiro[isoquinoline-1,4'-piperidine]-1'-yl)acetamide,
2-methyl-1'-(2-(tetrahydro-2H-pyran-4-yl)ethyl)-3,4-dihydro-2H-spiro[isoquinoline-1,4'-piperidine],
2-methyl-1'-(2-(pyridin-2-yl)ethyl)-3,4-dihydro-2H-spiro[isoquinoline-1,4'-piperidine],
2-methyl-1'-(2-(pyridin-3-yl)ethyl)-3,4-dihydro-2H-spiro[isoquinoline-1,4'-piperidine],
1'-(2-methoxyethyl)-2-methy-3,4-dihydro-2H-spiro[isoquinoline-1,4'-piperidine],
1'-(2-isopropoxyethyl)-2-methyl-3,4-dihydro-2H-spiro[isoquinoline-1,4'-piperidine],
2-methyl-1'-(2-(piperidin-1-yl)ethyl)-3,4-dihydro-2H-spiro[isoquinoline-1,4'-piperidine],
4-(2-(2-methyl-3,4-dihydro-2H-spiro[isoquinoline-1,4'-piperidine]-1'-yl)ethyl)morpholin-3-one,
N-methyl-3-(2-methyl-3,4-dihydro-2H-spiro[isoquinoline-1,4'-piperidine]-1'-yl)-N-phenylpropanamide,
2-methyl-1'-(pyridin-2-ylmethyl)-3,4-dihydro-2H-spiro[isoquinoline-1,4'-piperidine],
2-methyl-1'-(pyridine-4-ylmethyl)-3,4-dihydro-2H-spiro[isoquinoline-1,4'-piperidine],
2-methyl-1'-(pyridin-3-ylmethyl)-3,4-dihydro-2H-spiro[isoquinoline-1,4'-piperidine],
2-methyl-1'-(3-nitrophenethyl)-3,4-dihydro-2H-spiro[isoquinoline-1,4'-piperidine],
1-(4-fluoropiperidin-1-yl)-2-(2-methyl-3,4-dihydro-2H-spiro[isoquinoline-1,4'-piperidine]-1'-yl)propan-1-one,
N-isobutyl-N-methyl-2-(2-methyl-3,4-dihydro-2H-spiro[isoquinoline-1,4'-piperidine]-1'-yl)acetamide,
1-(3,3-difluoropiperidin-1-yl)-2-(2-methyl-3,4-dihydro-2H-spiro[isoquinoline-1,4'-piperidine]-1'-yl)ethanone,
N-ethyl-N-isopropyl-2-(2-methyl-3,4-dihydro-2H-spiro[isoquinoline-1,4'-piperidine]-1'-yl)acetamide,
2-(2-methyl-3,4-dihydro-2H-spiro[isoquinoline-1,4'-piperidine]-1'-yl)-1-(pyrrolidin-1-yl)ethanone,
2-(2-methyl-3,4-dihydro-2H-spiro[isoquinoline-1,4'-piperidine]-1'-yl)-1-(4-(trifluoromethyl)piperidin-1-yl)ethanone,
1-(3,3-difluoropyrrolidin-1-yl)-2-(2-methyl-3,4-dihydro-2H-spiro[isoquinoline-1,4'-piperidine]-1'-yl)ethanone, N-benzyl-N-methyl-2-(2-methyl-3,4-dihydro-2H-spiro[isoquinoline-1,4'-piperidine]-1'-yl)acetamide,
(S)-1-(3-fluoropyrrolidin-1-yl)-2-(2-methyl-3,4-dihydro-2H-spiro[isoquinoline-1,4'-piperidine]-1'-yl)ethanone,
(R)-1-(3-fluoropyrrolidin-1-yl)-2-(2-methyl-3,4-dihydro-2H-spiro[isoquinoline-1,4'-piperidine]-1'-yl)ethanone,
2-(2-methyl-3,4-dihydro-2H-spiro[isoquinoline-1,4'-piperidine]-1'-yl)-1-(pyridin-3-yl)ethanol,
2-(2-methyl-3,4-dihydro-2H-spiro[isoquinoline-1,4'-piperidine]-1'-yl)-1-(pyridin-2-yl)ethanol,
2-(2-methyl-3,4-dihydro-2H-spiro[isoquinoline-1,4'-piperidine]-1'-yl)-1-(pyrindin-4-yl)ethanol,
(R)-2-(2-methyl-3,4-dihydro-2H-spiro[isoquinoline-1,4'-piperidine]-1'-yl)-1-(pyridin-4-yl)ethanol,
(S)-2-(2-methyl-3,4-dihydro-2H-spiro[isoquinoline-1,4'-piperidine]-1'-yl)-1-(pyridin-4-yl)ethanol,
N-(cyclopropylmethyl)-N-ethyl-2-(2-methy-3,4-dihydro-2H-spiro[isoquinoline-1,4'-piperidine]-1'-yl)acetamide
N,N-diisopropyl-2-(2-methyl-3,4-dihydro-2H-spiro[isoquinoline-1,4'-piperidine]-1'-yl)acetamide,
N-isopropyl-N-methyl-2-(2-methyl-3,4-dihydro-2H-spiro[isoquinoline-1,4'-piperidine]-1'-yl)acetamide,
N-ethyl-N-isobutyl-2-(2-methyl-3,4-dihydro-2H-spiro[isoquinoline-1,4'-piperidine]-1'-yl)acetamide,
N-ethyl-2-(2-methyl-3,4-dihydro-2H-spiro[isoquinoline-1,4'-piperidine]-1'-yl)-N-propylacetamide,
N-cyclopropyl-N-ethyl-2-(2-methyl-3,4-dihydro-2H-spiro[isoquinoline-1,4'-piperidine]-1'-yl)acetamide,
N-isopropyl-2-(2-methyl-3,4-dihydro-2H-spiro[isoquinoline-1,4'-piperidine]-1'-yl)-N-propylacetamide,
N-isopropyl-N-(2-methoxyethyl)-2-(2-methyl-3,4-dihydro-2H-spiro[isoquinoline-1,4'-piperidine]-1'-yl)acetamide,
N-ethyl-2-(2-methyl-3,4-dihydro-2H-spiro[isoquinoline-1,4'-piperidine]-1'-yl)-N-(pentan-3-yl)acetamide
N-isobutyl-N-isopropyl-2-(2-methyl-3,4-dihydro-2H-spiro[isoquinoline-1,4'-piperidine]-1'-yl)acetamide,
N-methyl-2-(2-methyl-3,4-dihydro-2H-spiro[isoquinoline-1,4'-piperidine]-1-yl)-N-(pentan-3-yl)acetamide,
N-(cyclopropylmethyl)-N-methyl-2-(2-methyl-3,4-dihydro-2H-spiro[isoquinoline-1,4'-piperidine]-1'-yl)acetamide,
1-(3-fluoropyridin-4-yl)-2-(2-methyl-3,4-dihydro-2H-spiro[isoquinoline-1,4'-piperidine]-1'-yl)ethanol,
2-(2-methyl-3,4-dihydro-2H-spiro[isoquinoline-1,4'-piperidine]-1'-yl)-1-(4-methylpiperidin-1-yl)ethanone,
1-((2S,6R)2,6-dimethylmorpholino)-2-(2-methyl-3,4-dihydro-2H-spiro[isoquinoline-1,4'-piperidine]-1'-yl)ethanone,
N-methyl-2-(2-methyl-3,4-dihydro-2H-spiro[isoquinoline-1,4'-piperidine]-1'-yl)-N-(pyridin-2-ylmethyl)acetamide,
3-(2-(2-methyl-3,4-dihydro-2H-spiro[isoquinoline-1,4'-piperidine]-1'-yl)ethyl)aniline,
N-(3-(2-(2-methyl-3,4-dihydro-2H-spiro[isoquinoline-1,4'-piperidine]-1'-yl)ethyl)phenyl)methanesulfonamide,
N-(3-(2-(2-methyl-3,4-dihydro-2H-spiro[isoquinoline-1,4'-piperidine]-1'-yl)ethyl)phenyl)acetamide,
2-(2-methyl-3,4-dihydro-2H-spiro[isoquinoline-1,4'-piperidine]-1'-yl)-1-phenylethanol,
2-methyl-1'-(2-(pyridin-4-yl)ethyl)-3,4-dihydro-2H-spiro[isoquinoline-1,4'-piperidine],
2-(2-methoxyethyl)-1'-phenethyl-3,4-dihydro-2H-spiro[isoquinoline-1,4'-piperidine],
2-(1'-phenethyl-3,4-dihydro-2H-spiro[isoquinoline-1,4'-piperidine]-2-yl)ethanol,
2-(2-methoxyethyl)-1'-(2-(pyridin-3-yl)ethyl)-3,4-dihydro-2H-spiro[isoquinoline-1,4'-piperidine],
2-(1'-(2-(pyridin-3-yl)ethyl)-3,4-dihydro-2H-spiro[isoquinoline-1,4'-piperidine]-2-yl)ethanol,
2-(2-(2-hydroxyethyl)-3,4-dihydro-2H-spiro[isoquinoline-1,4'-piperidine]-1'-yl)-1-(piperidin-1-yl)ethanone,
2-(1'-(2-(5-fluoropyridin-3-yl)ethyl)-3,4-dihydro-2H-spiro[isoquinoline-1,4'-piperidine]-2-yl)ethanol,
2-(1'-(2-(5-(trifluoromethyl)pyridin-3-yl)ethyl)-3,4-dihydro-2H-spiro[isoquinoline-1,4'-piperidine]-2-yl)ethanol,
2-(1'-(2-(pyridin-4-yl)ethyl)-3,4-dihydro-2H-spiro[isoquinoline-1,4'-piperidine]-2-yl)ethanol,
2-(1'-(2-(3-fluoropyridin-4-yl)ethyl)-3,4-dihydro-2H-spiro[isoquinoline-1,4'-piperidine]-2-yl)ethanol,
2-methyl-1'-phenethyl-3,4-dihydro-2H-spiro[isoquinoline-1,4'-piperidin]-6-ol,
2,2,2-trifluoro-1-(1'-phenethyl-3,4-dihydro-2H-spiro[isoquinoline-1,4'-piperidine]-2-yl)ethanone,
1'-phenethyl-2-(2,2,2-trifluoroethyl)-3,4-dihydro-2H-spiro[isoquinoline-1,4'-piperidine],
1-morpholino-2-(2-(2,2,2-trifluoroethyl)-3,4-dihydro-2H-spiro[isoquinoline-1,4'-piperidine]-1'-yl)ethanone,
1-(piperidin-1-yl)-2-(2-(2,2,2-trifluoroethyl)-3,4-dihydro-2H-spiro[isoquinoline-1,4'-piperidine]-1'-yl)ethanone,
1'-(2-(pyridin-4-yl)ethyl)2(2,2,2-trifluoroethyl)-3,4-dihydro-2H-spiro[isoquinoline-1,4'-piperidine],
1'-(2-(pyridin-3-yl)ethyl)-2-(2,2,2-trifluoroethyl)-3,4-dihydro-2H-spiro[isoquinoline-1,4'-piperidine],
1-(piperidin-1-yl)-2-(2,4,4-trimethyl-3,4-dihydro-2H-spiro[isoquinoline-1,4'-piperidine]-1'-yl)ethanone,
1-(1'-phenethylspiro[isoindoline-1,4'-piperidine]-2-yl)ethanone,
2-methyl-1'-phenethylspiro[isoindoline-1,4'-piperidine],
2-methyl-1'-((tetrahydro-2H-pyran-4-yl)methyl)spiro[isoindoline-1,4'-piperidine],
(R)-1-(3-fluoropyridin-4-yl)-2-(2-methyl-3,4-dihydro-2H-spiro[isoquinoline-1,4'-piperidine]-1'-yl)ethanol,
(S)-1-(3-fluoropyridin-4-yl)-2-(2-methyl-3,4-dihydro-2H-spiro[isoquinoline-1,4'-piperidine]-1'-yl)ethanol,
N-ethyl-2-(2-ethyl-3,4-dihydro-2H-spiro[isoquinoline-1,4'-piperidine]-1'-yl)-N-isopropylacetamide,
1-(4,4-difluoropiperidin-1-yl)-2-(2-ethyl-3,4-dihydro-2H-spiro[isoquinoline-1,4'-piperidine]-1'-yl)ethanone,
2-(2-ethyl-3,4-dihydro-2H-spiro[isoquinoline-1,4'-piperidine]-1'-yl)-1-(pyridin-4-yl)ethanol,
2-(2-ethyl-3,4-dihydro-2H-spiro[isoquinoline-1,4'-piperidine]-1'-yl)-1-morpholinoethanone,
4-(2-(2-ethyl-3,4-dihydro-2H-spiro[isoquinoline-1,4'-piperidine]-1'-yl)ethyl)morpholine,
2-(2-ethyl-3,4-dihydro-2H-spiro[isoquinoline-1,4'-piperidine]-1'-yl)-1-(1,1-dioxo-thiomorpholin-4-yl)ethanone,
2-(2-ethyl-3,4-dihydro-2H-spiro[isoquinoline-1,4'-piperidine]-1'-yl)-1-(4-fluoropiperidin-1-yl)ethanone,
1-(3,3-difluoropiperidin-1-yl)-2-(2-ethyl-3,4-dihydro-2H-spiro[isoquinoline-1,4'-piperidine]-1'-yl)ethanone,
2-(2-ethyl-3,4-dihydro-2H-spiro[isoquinoline-1,4'-piperidine]-1'-yl)-N-methyl-N-(pentan-3-yl)acetamide,
2-(2-ethyl-3,4-dihydro-2H-spiro[isoquinoline-1,4'-piperidine]-1'-yl)-N,N-dimethylacetamide,
N-cyclopropyl-N-ethyl-2-(2-ethyl-3,4-dihydro-2H-spiro[isoquinoline-1,4'-piperidine]-1'-yl)acetamide,
N,N-diethyl-2-(2-ethyl-3,4-dihydro-2H-spiro[isoquinoline-1,4'-piperidine]-1'-yl)acetamide, 1-(4,4-difluoropiperidin-1-yl)-2-(2-methylspiro[isoindo-line-1,4'-piperidine]-1'-yl)ethanone, N-ethyl-N-isopropyl-2-(2-methylspiro[isoindoline-1,4'-piperidine]-1'-yl)acetamide, N-ethyl-1'-(2-(pyridin-4-yl)ethyl)-3,4-dihydro-2H-spiro[isoquinoline-1,4'-piperidine]-2-carboxamide, 1'-(2-(Pyrimidin-5-yl)ethyl)-2-(2,2,2-trifluoroethyl)-3,4-dihydro-2H-spiro[isoquinoline-1,4'-piperidine], and 2-(2-(2-Methyl-3,4-dihydro-2H-spiro[isoquinoline-1,4'-piperidine]-1'-yl)ethylamino)ethanol.

12. A process for the preparation of a compound of Formula (I) according to claim 1,

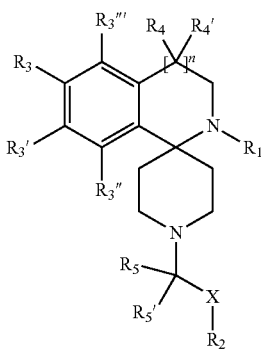

(I)

wherein the process comprises a) reacting a compound of formula IX with a suitable reagent of formula Xa-d, using different conditions depending on the reagent nature,

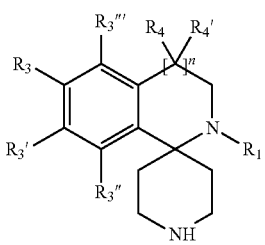

IX wherein, n, $R_1$, $R_2$, $R_3$, $R_{3'}$, $R_{3''}$, $R_{3'''}$, $R_4$ and $R_{4'}$ are as defined in claim 1 for the compound of formula (I), Xa is $WCR_5R_{5'}XR_2$, Xb is $O{=}CR_5R_{5'}XR_2$, Xc is $CR_5R_{5'}{=}CR_xR_2$, Xd is $CR_5R_{5'}OCR_xR_2$; and W is a leaving group, or b) reacting a compound of formula XII with a reducing agent, in a suitable solvent, at a suitable temperature comprised between room temperature and the reflux temperature,

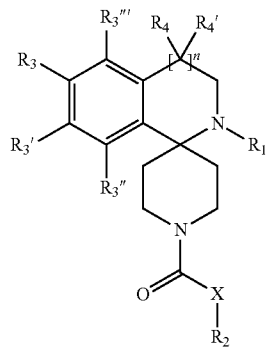

(XII)

wherein, n, X, $R_1$, $R_2$, $R_3$, $R_{3'}$, $R_{3''}$, $R_{3'''}$, $R_4$ and $R_{4'}$ are as defined in claim 1 for the compound of formula (I), or c) by reaction of intermediate XIV with Xa-d, followed by reaction with VIIa-h,

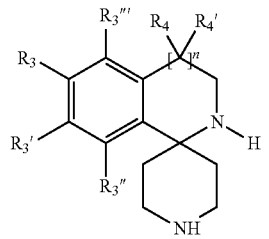

(XIV)

wherein, n, $R_1$, $R_2$, $R_3$, $R_{3'}$, $R_{3''}$, $R_{3'''}$, $R_4$ and $R_{4'}$ are as defined in claim 1 for the compound of formula (I), Xa is $WCR_5R_{5'}XR_2$, Xb is $O{=}CR_5R_{5'}XR_2$, Xc is $CR_5R_{5'}{=}CR_xR_2$, Xd is $CR_5R_{5'}OCR_xR_2$;

VIIa is $R_1{=}O$,

VIIb is $R_1W$,

VIIc is $R_6COW$,

VIId is $(R_6CO)_2$,

VIIe is $R_6SO_2W$,

VIIf is $R_6NCO$,

VIIg is $R_6NSO$,

VIIh is $R_6COOW$, and

W is a leaving group, or d) transforming intermediate XV by reduction with a reducing agent, in a suitable solvent, at a suitable temperature comprised between room temperature and the reflux temperature, followed by reaction with VIIa-h under the suitable conditions, or in the case where $R_1$ is alkyl, the step order can be inverted and compound I can be obtained by reaction of intermediate XV with VIIb under the suitable conditions, followed by reduction with a reducing agent, in a suitable solvent, at a suitable temperature comprised between room temperature and the reflux temperature,

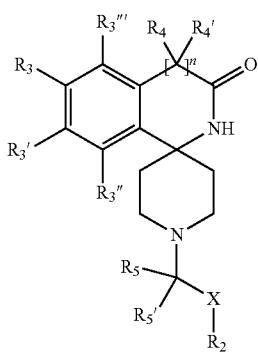

(XV)

wherein, n, X, $R_1$, $R_2$, $R_3$, $R_{3'}$, $R_{3''}$, $R_{3'''}$, $R_4$, $R_{4'}$, $R_5$ and $R_{5'}$ are as defined in claim 1 for the compound of formula (I), VIIa is $R_1$=O,
VIIb is $R_1$W,
VIIc is $R_6$COW,
VIId is $(R_6CO)_2$,
VIIe is $R_6SO_2W$,
VIIf is $R_6$NCO,
VIIg is $R_6$NSO,
VIIh is $R_6$COOW, and
W is a leaving group, or e) in the case where $R_3$, $R_{3'}$, $R_{3''}$ or $R_{3'''}$ is an electron donating group, compound I can also be prepared by reaction of a compound of formula VI with a compound of formula XVI in a suitable solvent, at a suitable temperature between 80 and 120°C. followed by reaction of with VIIa-h.

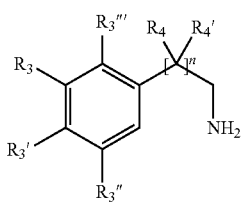

(VI)

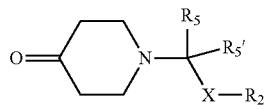

(XVI)

wherein, n, $R_1$, $R_2$, $R_3$, $R_{3'}$, $R_{3''}$, $R_{3'''}$, $R_4$, $R_{4'}$, $R_5$ and $R_{5'}$ are as defined in claim 1 for the compound of formula (I), VIIa is $R_1$=O,
VIIb is $R_1$W,
VIIc is $R_6$COW,
VIId is $(R_6CO)_2$,
VIIe is $R_6SO_2W$,
VIIf is $R_6$NCO,
VIIg is $R_6$NSO,
VIIh is $R_6$COOW, and
W is a leaving group.

13. A pharmaceutical composition which comprises the compound according to claim 1, or a pharmaceutically acceptable salt thereof, and a pharmaceutically acceptable carrier, adjuvant or vehicle.

14. A method of treating pain in a subject in need thereof, comprising administration of an effective amount of the compound to said subject according to claim 1.

15. The method according to claim 14, wherein the pain is selected from medium to severe pain, visceral pain, chronic pain, cancer pain, migraine, inflammatory pain, acute pain, neuropathic pain, allodynia, and hyperalgesia.

16. The compound according to claim 1, wherein the compound is in the form of an enantiomer or diastereomer.

17. The compound according to claim 1, wherein the compound is in the form of a mixture of enantiomers and/or diastereomers, in any mixing ratio.

\* \* \* \* \*

UNITED STATES PATENT AND TRADEMARK OFFICE
CERTIFICATE OF CORRECTION

Page 1 of 2

PATENT NO. : 10,407,428 B2
APPLICATION NO. : 15/527909
DATED : September 10, 2019
INVENTOR(S) : Carmen Almansa-Rosales, Monica Garcia-Lopez and Ana-Maria Caamaño-Moure It is certified that error appears in the above-identified patent and that said Letters Patent is hereby corrected as shown below:

In the Claims

Column 226, Line 42; "–C(O)OR$_{14'}$," should read -- –C(O)OR$_{14}$, --

Column 226, Line 61; "–S(O)$_2$R$_{9'}$," should read -- –S(O)$_2$R$_9$, --

Column 227, Line 2; "–S(O)$_2$R$_{9'}$," should read -- –S(O)$_2$R$_9$, --

Column 227, Line 22; "R$_{13'''}$" should read -- R$_{13''}$ --

Column 227, Lines 33 and 34; delete "preferably stereoisomers,"

Column 229, Line 7; "(cyclopropymethoxy)" should read -- (cyclopropylmethoxy) --

Column 229, Line 62; "eridine]-1-yl)-" should read -- eridine]-1'-yl)- --

Column 230, Line 35; "-2-methy-3,4-" should read -- -2-methyl-3,4- --

Column 230, Line 47; "-(pyridine-4-" should read -- -(pyridin-4- --

Column 231, Line 12; "-(pyrindin-4-" should read -- -(pyridin-4- --

Column 231, Line 18; "(2-methy-3,4-" should read -- (2-methyl-3,4- --

Column 231, Line 40; "-piperidine]-1-yl)-" should read -- piperidine]-1'-yl)- --

Column 232, Line 28; "ethyl)2(" should read -- ethyl)-2-( --

Signed and Sealed this
Nineteenth Day of November, 2019

Andrei Iancu
*Director of the United States Patent and Trademark Office*

CERTIFICATE OF CORRECTION (continued)
U.S. Pat. No. 10,407,428 B2

Column 232, Line 40; "]-1-yl)" should read -- "]-1'-yl) --

Column 232, Line 42; "]-1-yl)" should read -- "]-1'-yl) --